United States Patent
Sakamoto et al.

(10) Patent No.: US 9,403,802 B2
(45) Date of Patent: Aug. 2, 2016

(54) HETEROCYCLIC COMPOUND AND USE THEREFOR

(71) Applicant: Takeda Pharmaceutical Company Limited, Osaka-shi, Osaka (JP)

(72) Inventors: Hiroki Sakamoto, Kanagawa (JP); Takahiro Sugimoto, Kanagawa (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 0 days.

(21) Appl. No.: 14/382,390

(22) PCT Filed: Feb. 28, 2013

(86) PCT No.: PCT/JP2013/055566
§ 371 (c)(1),
(2) Date: Sep. 2, 2014

(87) PCT Pub. No.: WO2013/129622
PCT Pub. Date: Sep. 6, 2013

(65) Prior Publication Data
US 2015/0126487 A1    May 7, 2015

(30) Foreign Application Priority Data
Mar. 2, 2012 (JP) .................. 2012-047320

(51) Int. Cl.
| C07D 401/14 | (2006.01) |
| C07D 209/12 | (2006.01) |
| C07D 401/04 | (2006.01) |
| C07D 405/12 | (2006.01) |
| C07D 215/56 | (2006.01) |
| C07D 401/10 | (2006.01) |
| C07D 401/12 | (2006.01) |
| C07D 237/28 | (2006.01) |
| C07D 401/06 | (2006.01) |
| C07D 403/10 | (2006.01) |

(52) U.S. Cl.
CPC ............ *C07D 405/12* (2013.01); *C07D 215/56* (2013.01); *C07D 237/28* (2013.01); *C07D 401/06* (2013.01); *C07D 401/10* (2013.01); *C07D 401/12* (2013.01); *C07D 403/10* (2013.01)

(58) Field of Classification Search
None
See application file for complete search history.

(56) References Cited
U.S. PATENT DOCUMENTS
2008/0108659 A1   5/2008   Gandhi et al.

FOREIGN PATENT DOCUMENTS

| EP | 0 560 604 | 9/1993 |
| GB | 1 433 774 | 4/1976 |
| JP | 64-061461 | 3/1989 |
| JP | 2-124871 | 5/1990 |
| JP | 2008-506692 | 3/2008 |
| JP | 2008-509926 | 5/2008 |
| WO | 91/05783 | 5/1991 |
| WO | 95/30647 | 11/1995 |
| WO | 01/19830 | 3/2001 |
| WO | 2013/063549 | 5/2003 |
| WO | 2005/021532 | 3/2005 |
| WO | 2006/019768 | 2/2006 |
| WO | 2006/020879 | 2/2006 |
| WO | 2007/059108 | 5/2007 |
| WO | 2007/067489 | 6/2007 |
| WO | 2007/100366 | 9/2007 |
| WO | 2007/139464 | 12/2007 |
| WO | 2008/002621 | 1/2008 |
| WO | 2009/051715 | 4/2009 |
| WO | 2009/053799 | 4/2009 |
| WO | 2009/094279 | 7/2009 |
| WO | 2009/102574 | 8/2009 |
| WO | 2009/102588 | 8/2009 |
| WO | 2009/117283 | 9/2009 |
| WO | 2009/134668 | 11/2009 |
| WO | 2010/019391 | 2/2010 |

(Continued)

OTHER PUBLICATIONS

Reddy et al., 23(7) Asian J. Chem. 2981-2988 (2011) (CAS Abstract).*
Reddy, et al., "An Expeditious Synthesis of Some Novel N-Pyridyl-1,4-dihydro-4-oxo-3-quinoline Carboxylic Acids/Amides as Potential CB2 Cannabinoid Receptor Agonists", Asian Journal of Chemistry, vol. 23, No. 7, 2011, pp. 2981-2988.

(Continued)

*Primary Examiner* — Timothy R Rozof
(74) *Attorney, Agent, or Firm* — Hamre, Schumann, Mueller & Larson, P.C.

(57) ABSTRACT

The present invention provides a compound having a cholinergic muscarinic M1 receptor positive allosteric modulator activity, and useful as a prophylactic or therapeutic drug for Alzheimer's disease, schizophrenia, pain, a sleep disorder and the like. The present invention relates to a compound represented by the formula (I):

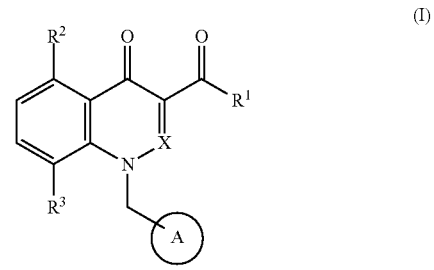

wherein $R^1$ is an optionally substituted amino group or an optionally substituted cyclic amino group, $R^2$ and $R^3$ are each independently a hydrogen atom or a substituent, X is —CH= or —N=, and ring A is an optionally substituted 5- to 10-membered ring, or a salt thereof.

14 Claims, No Drawings

(56) References Cited

FOREIGN PATENT DOCUMENTS

| WO | 2010/042347 | 4/2010 |
|---|---|---|
| WO | 2010/047990 | 4/2010 |
| WO | 2010/059773 | 5/2010 |
| WO | 2010/096338 | 8/2010 |
| WO | 2010/123716 | 10/2010 |
| WO | 2011/006794 | 1/2011 |
| WO | 2011/025851 | 3/2011 |
| WO | 2011/041143 | 4/2011 |
| WO | 2011/049731 | 4/2011 |
| WO | 2011/062853 | 5/2011 |
| WO | 2011/075371 | 6/2011 |
| WO | 2011/084368 | 7/2011 |
| WO | 2011/084371 | 7/2011 |
| WO | 2011/137049 | 11/2011 |
| WO | 2011/149801 | 12/2011 |
| WO | 2011/159553 | 12/2011 |
| WO | 2011/159554 | 12/2011 |
| WO | 2011/163280 | 12/2011 |
| WO | 2012/003147 | 1/2012 |
| WO | 2014/077401 | 5/2014 |

OTHER PUBLICATIONS

Kuduk, et al., "Identification of Amides as Carboxylic Acid Surrogates for Quinolizidinone-Based M1 Positive Allosteric Modulators", ACS Medicinal Chemistry Letters, vol. 3, Oct. 13, 2012, pp. 1070-1074.

Wess, et al., "Muscarinic acetylcholine receptors: mutant mice provide new insights for drug development", Nature Reviews Drug Discovery, vol. 6, Sep. 2007, pp. 721-733.

Chen, et al. "Design, synthesis, and biological evaluation of novel quinoline derivatives as HIV-1 Tat-TAR interaction inhibitors", Bioorganic & Madicinal Chemistry, vol. 17, No. 5, 2009, pp. 1948-1956.

Stern, et al., "Pharmacomodulations around the 4-Oxo-1,4-dihydroquinoline-3-carboxamides, a Class of Potent CB2-Selective Cannabinoid Receptor Ligands: Consequences in Receptor Affinity and Functionality", Journal of Medicinal Chemistry, vol. 50, No. 22, 2007, pp. 5471-5484.

Tuccinardi, et al., "Structure-Based Virtual Screening: Identification of Novel CB2 Receptor Ligands", Letters in Drug Design & Discovery, vol. 4, No. 1, 2007, pp. 15-19.

Stern, et al., "Novel 4-Oxo-1,4-dihydroquinoline-3-carboxamide Derivatives as New CB2 Cannabinoid Receptors Agonists: Synthesis, Pharmacological Properties and Molecular Modeling", Journal of Medicinal Chemistry, vol. 49, No. 1, 2006, pp. 70-79.

Ward, et al., "Synthesis and Structure Activity Relationships of 4-Quinolonecarboxamides with 5-HT3 Antagonist Activity", Medicinal Chemistry Research, vol. 4, No. 4, 1993, pp. 267-272.

Gundel, et al., "Synthese and Reactions of [1.4]Diazepion[6.5-c]quinolines", Zeitschrift fur Naturforschung, 43b, 1988, pp. 769-777 with an English abstract.

Bohnert, et al., "Redox Reactions with Cyclopeptide-Like Quinoline Derivatives as Lipophilic NAD Model Compounds", Zeitschrift fur Naturforschung, 42b, 1987, pp. 1159-1166 with an English abstract.

Angelino, et al., :The Oxidation of 1-Alkyl(aryl)quinolinium Chlorides with Rabbit Liver Aldehyde Oxidase, Journal of Heterocyclic Chemistry, vol. 21, No. 1, 1984, pp. 107-112.

CAS Registry Numbers: RN 1328835-66-0, RN 1329479-67-5, RN 1330047-24-9, RN 1330047-67-0, RN 1330126-62-9, RN 1329780-84-8, RN 1330126-45-8, RN 1329933-94-9, RN 1330242-66-4, RN 1401512-95-5, and RN 1401512-96-6, 3 pages.

Novelty Search Results, 163 pages.

Budzik, et al., "2' Biaryl amides as novel and subtype selective M1 agonists. Part II: Further optimization and profiling", Bioorganic & Medicinal Chemistry Letters, 2010, vol. 20, No. 12, pp. 3545-3549.

Bridges, et al., "Chemical lead optimization of a pan Gq mAChR M1, M3, M5 positive allosteric modulator (PAM) lead. Part II: Development of a potent and highly selective M1 PAM", Bioorganic & Medicinal Chemistry Letters, 2010, vol. 20, pp. 1972-1975.

Gordon, et al., "A facile, protic ionic liquid route to N-substituted 5-hydroxy-4-methyl-3-oxoisoindoline-1-carboxamides and N-substituted 3-oxoisoindoline-4-carboxylic acids", Green Chemistry, 2010, vol. 12, pp. 1000-1006.

International Search Report issued in International Application No. PCT/JP2013/055566, 4 pages, May 28, 2013.

Written Opinion of the International Searching Authority issued in International Application No. PCT/JP2013/055566, 6 pages, May 28, 2013.

International Search Report issued in International Application No. PCT/JP2013/081084, 9 pages, Apr. 8, 2014.

Extended European Search Report issued in the corresponding European Patent Application No. 13754154.6 dated Sep. 2, 2015 (9 pages).

Manera et al.: "New 1,8-naphthyridine and quinoline derivatives as CB2 selective agonists"; Bioorganic and Medicinal Chemistry Letters, vol. 17, No. 23, Nov. 2007, pp. 6505-6510 (6 pages).

Clementina Manera et al.: "Design, Synthesis and Biological Evaluation of New 1,8-Naphthyridin-4(1H)-on-3-carboxamide and Quinolin-4(1H)-on-3-carbonxamide Derivatives as CB2 Selective Agonists"; Journal of Medicinal Chemistry, vol. 49, No. 20, Oct. 2006, pp. 5947-5957 (11 pages).

Michelle Roche et al.: "Brain CB2 Receptors: Implications for Neuropsychiatric Disorders"; Pharmaceuticals, vol. 3, No. 8, Aug. 2010, pp. 2517-2553 (37 pages).

Zhao, et al., "6,7-Dihydroxy-1-oxoisoindoline-4-sulfonamide-containing HIV-1 integrase inhibitors", Bioorganic & Medicinal Chemistry Letters, vol. 22, No. 24, Oct. 27, 2012, pp. 7309-7313.

Extended European Search Report issued in counterpart European Patent Application No. 13854399.6, Mar. 16, 2016, 7 pages.

Cornelison, "Human papillomavirus genotype 16 vaccines for cervical cancer prophylaxis and treatment", Curr. Opin. Oncol. 2000, vol. 12(5), p. 466.

Karran, et al., "The amyloid cascade hypotheis for Alzheimer's disease: an appraisal for the development of therapeutics", Nature, 2011, vol. 10, p. 698.

Schmitz, et al., "Hippocampal Neuron Loss Excess Amyloid Plaque Load in a Transgenic Mouse Model of Alzheimer's Disease", American Journal of Pathology, 2004, vol. 164, p. 1495.

\* cited by examiner

HETEROCYCLIC COMPOUND AND USE THEREFOR

TECHNICAL FIELD

The present invention relates to a heterocyclic compound having a cholinergic muscarinic M1 receptor positive allosteric modulator activity and useful as a medicament such as a prophylactic or therapeutic drug for Alzheimer's disease, schizophrenia, pain (pain), sleep disorder and the like, and the like. As used herein, the positive allosteric modulator activity refers to an action to potentiate receptor function by binding to a moiety different from that of an endogenous activator (acetylcholine for this receptor).

BACKGROUND OF THE INVENTION

Acetylcholine is a neurotransmitter that transmits stimulation in the parasympathetic nerve and motor nerve. Acetylcholine receptor is classified into a ligand dependency ion channel (cholinergic nicotinic receptor) and a G-protein-conjugated receptor (cholinergic muscarinic receptor). The cholinergic muscarinic receptor is one kind of receptor for excitatory neurotransmitter acetylcholine, and was named based on the selective activation of the receptor by muscarine. The muscarinic receptor is further classified into subtypes of M1 to M5, and the M1 receptor is known to be widely distributed in the brain, and deeply involved particularly in learning, memory, sleep, neuropathic pain and the like. The importance of cholinergic muscarinic M1 receptor in brain physiology is well known, and a compound having an M1 receptor function enhancing action is expected to be useful as a prophylactic or therapeutic drug for mental diseases, neurodegenerative diseases, memory disorders, pain, sleep disorders and the like (non-patent document 1)

WO 2007/067489 (patent document 1) and WO 2007/100366 (patent document 2) disclose the following compound as an M1 receptor positive allosteric modulator.

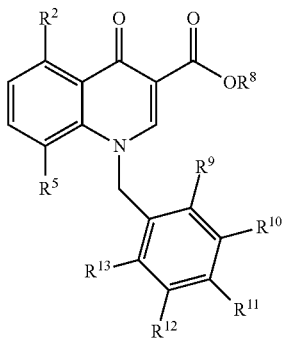

WO 2008/002621 (patent document 3) discloses the following compound as an M1 receptor positive allosteric modulator.

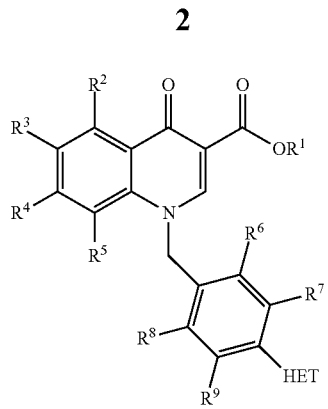

WO 2009/051715 (patent document 4) discloses the following compound as an M1 receptor positive allosteric modulator.

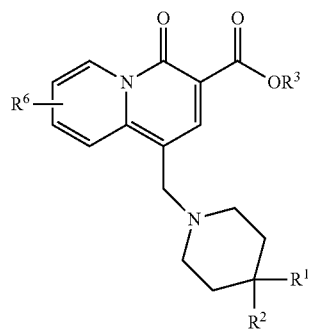

WO 2009/094279 (patent document 5) discloses the following compound as an M1 receptor positive allosteric modulator.

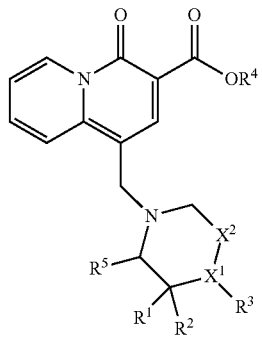

WO 2009/102574 (patent document 6) discloses the following compound as an M1 receptor positive allosteric modulator.

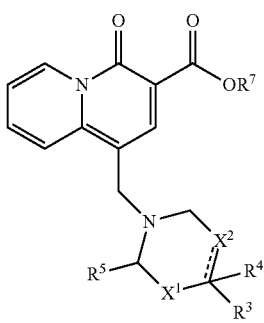

WO 2009/102588 (patent document 7) discloses the following compound as an M1 receptor positive allosteric modulator.

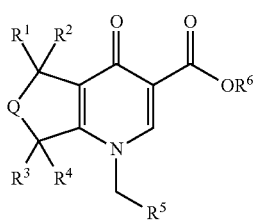

WO 2009/117283 (patent document 8) discloses the following compound as an M1 receptor positive allosteric modulator.

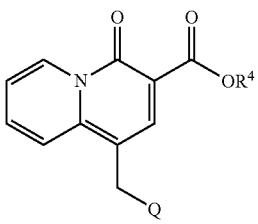

WO 2009/134668 (patent document 9) discloses the following compound as an M1 receptor positive allosteric modulator.

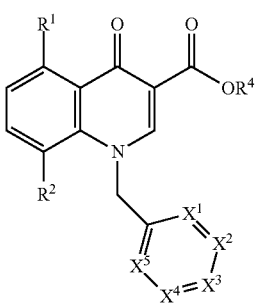

WO 2010/019391 (patent document 10) discloses the following compound as an M1 receptor positive allosteric modulator.

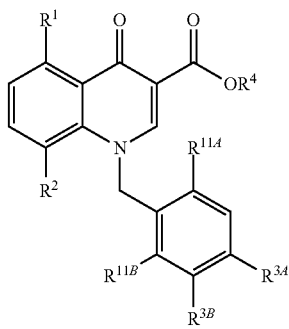

WO 2010/042347 (patent document 11) discloses the following compound as an M1 receptor positive allosteric modulator.

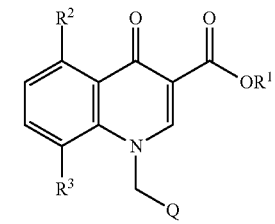

WO 2010/047990 (patent document 12) discloses the following compound as an M1 receptor positive allosteric modulator.

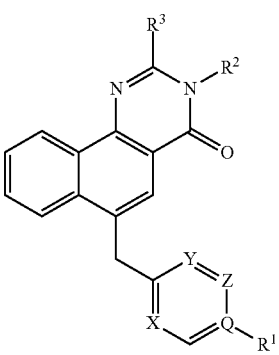

WO 2010/059773 (patent document 13) discloses the following compound as an M1 receptor positive allosteric modulator.

(I)

WO 2010/096338 (patent document 14) discloses the following compound as an M1 receptor positive allosteric modulator.

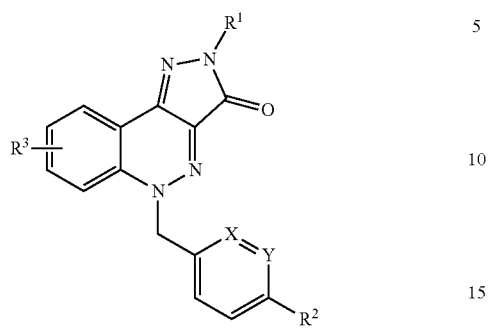

WO 2009/053799 (patent document 15) discloses the following compounds as an intermediate for a cannabinoid receptor ligand.

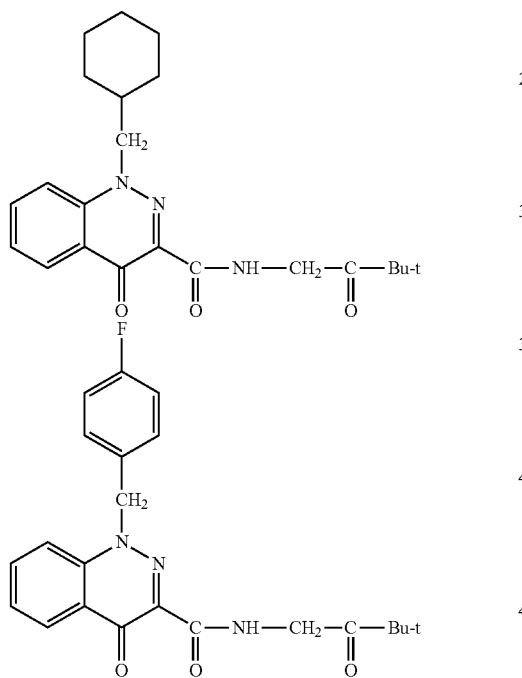

WO 2007/059108 (patent document 16) discloses the following compounds as an intermediate for a chemokine receptor CCXCKR2 antagonist.

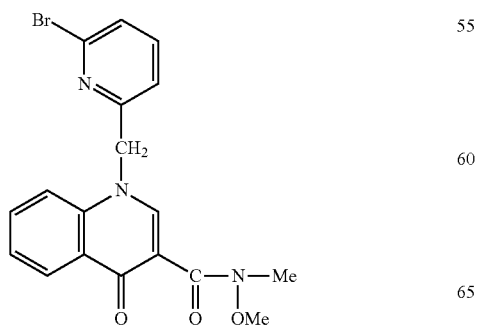

-continued

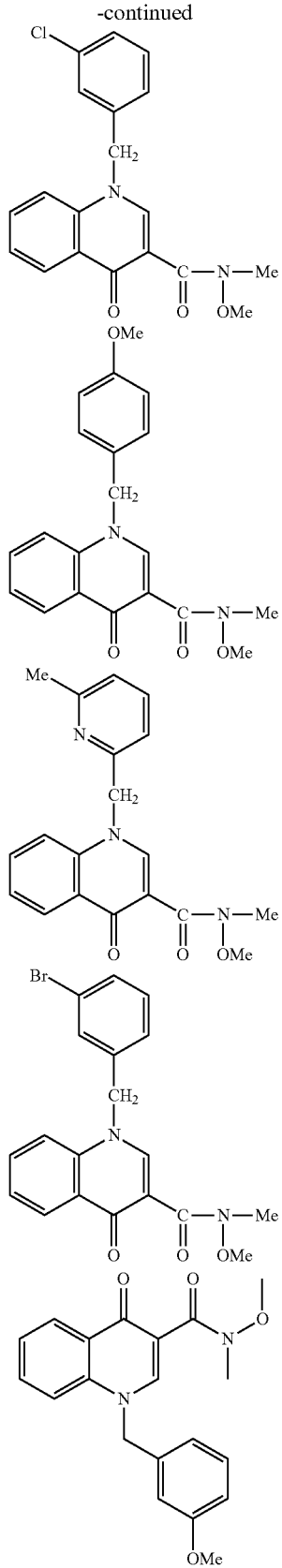

EP 0560604 (patent document 17) discloses the following compound as a 5-HT$_3$ receptor antagonist.

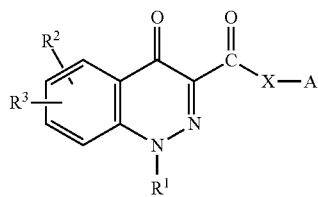

WO 91/05783 (patent document 18) discloses the following compound as a 5-HT$_3$ antagonist.

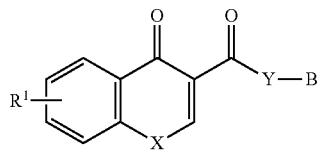

JP-A-H02-124871 (patent document 19) discloses the following compound as a compound having an antiallergic action based on a 5-lipoxygenase inhibitory action and the like.

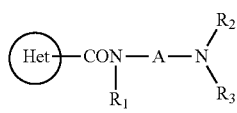

JP-A-S64-61461 (patent document 20) discloses the following compound as a compound having a myocardial contraction enhancing action, a coronary blood flow increasing action, a hypotensive action and the like.

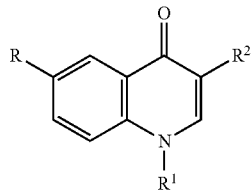

GB 1433774 (patent document 21) discloses the following compound as a compound inhibiting the release of a spasmogenic substance produced as a result of an antigen-antibody reaction.

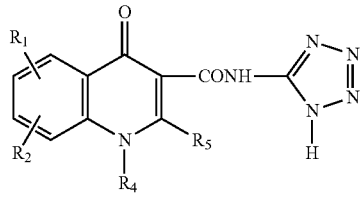

WO 2011/062853 (patent document 22) discloses the following compound as an M1 receptor positive allosteric modulator.

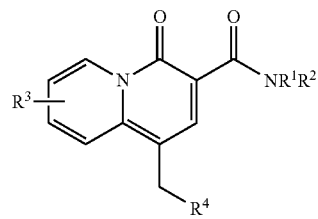

WO 2010/123716 (patent document 23) discloses the following compound as an M1 receptor positive allosteric modulator.

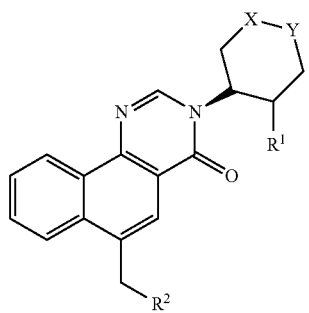

WO 2011/025851 (patent document 24) discloses the following compound as an M1 receptor positive allosteric modulator.

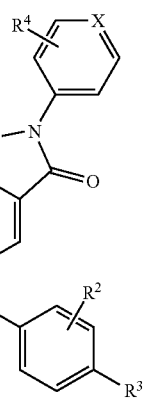

WO 2011/041143 (patent document 25) discloses the following compound as an M1 receptor positive allosteric modulator.

WO 2011/049731 (patent document 26) discloses the following compound as an M1 receptor positive allosteric modulator.

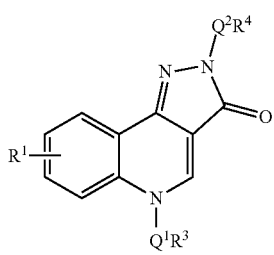

WO 2011/075371 (patent document 27) discloses the following compound as an M1 receptor positive allosteric modulator.

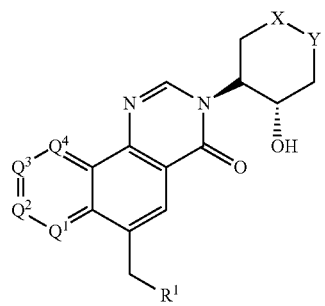

WO 2011/084368 (patent document 28) discloses the following compound as an M1 receptor positive allosteric modulator.

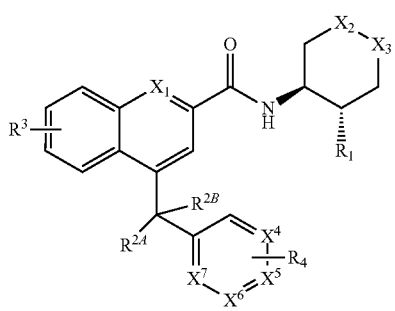

WO 2011/084371 (patent document 29) discloses the following compound as an M1 receptor positive allosteric modulator.

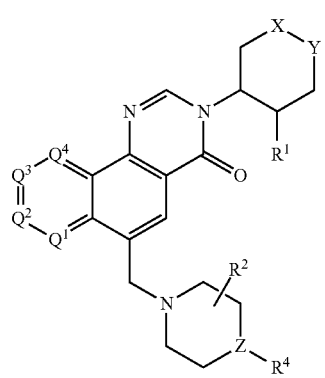

WO 2011/159554 (patent document 30) discloses the following compound as an M1 receptor positive allosteric modulator.

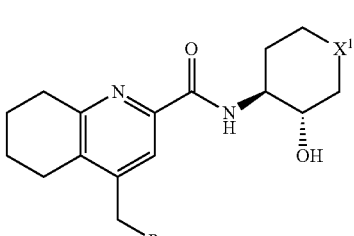

(I)

WO 2011/149801 (patent document 31) discloses the following compound as an M1 receptor positive allosteric modulator.

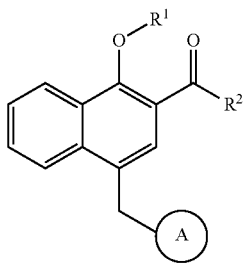

WO 2011/137049 (patent document 32) discloses the following compound as an M1 receptor positive allosteric modulator.

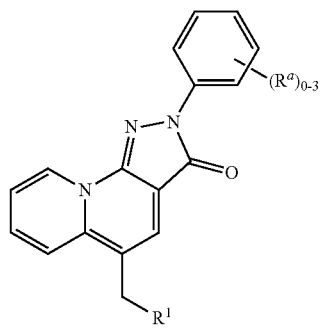

WO 2011/159553 (patent document 33) discloses the following compound as an M1 receptor positive allosteric modulator.

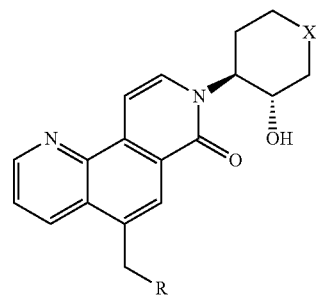

WO 2011/163280 (patent document 34) discloses the following compound as an M1 receptor positive allosteric modulator.

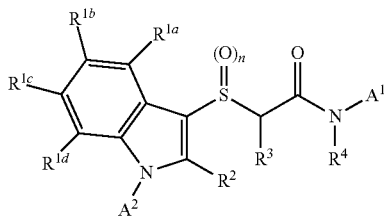
(I)

WO 2012/003147 (patent document 35) discloses the following compound as an M1 receptor positive allosteric modulator.

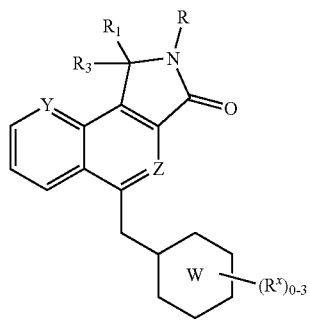
(I)

Bioorganic and Medicinal Chemistry (2009), 17(5), 1948-1956 (non-patent document 2) discloses the following compounds as an HIV-1 Tat-TAR interaction inhibitor.

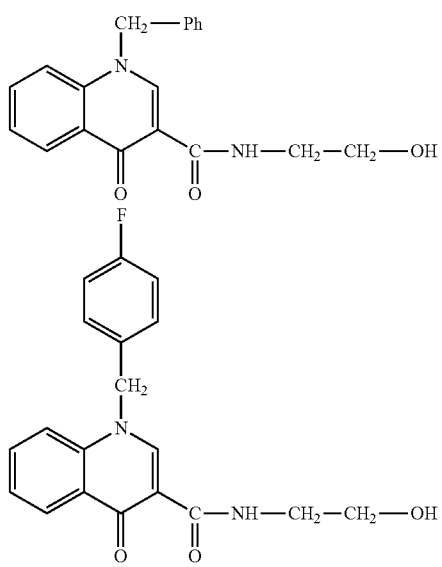

Oriental Journal of Chemistry (2007), 23(3), 935-942 (non-patent document 3) discloses the following compounds.

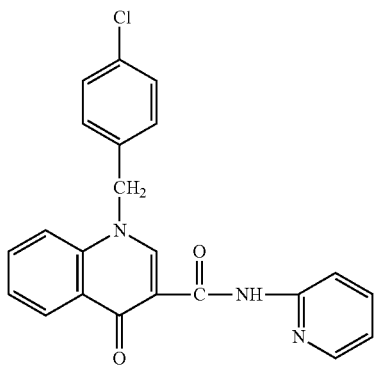

Journal of Medicinal Chemistry (2007), 50(22), 5471-5484 (non-patent document 4) discloses the following compounds as a CB2-selective cannabinoid receptor ligand.

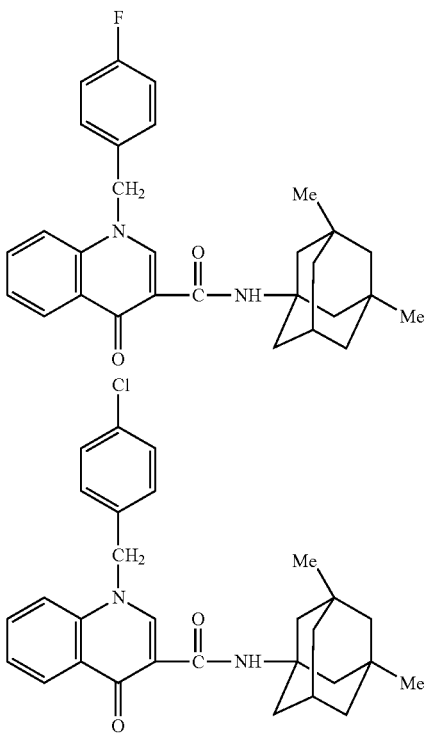

-continued

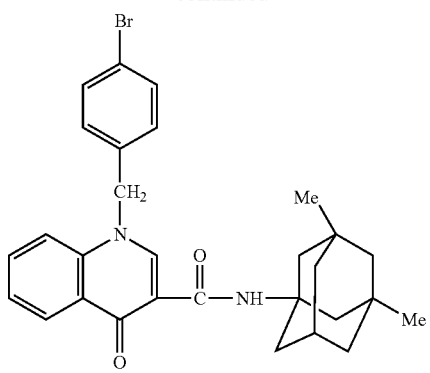

Letters in Drug Design & Discovery (2007), 4(1), 15-19 (non-patent document 5) discloses the following compound as a CB2 receptor ligand.

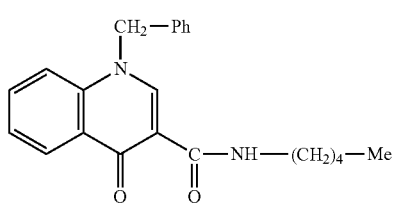

Journal of Medicinal Chemistry (2006), 49(1), 70-79 (non-patent document 6) discloses the following compound as a CB2 cannabinoid receptor agonist.

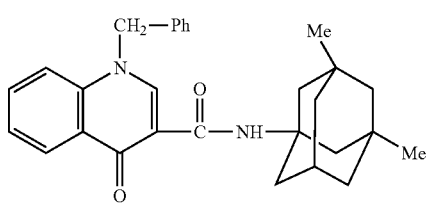 [SMILES: CC12CC3CC(C)(C1)CC(NC(=O)c1cn(Cc4ccccc4)c4ccccc4c1=O)(C3)C2]

Medicinal Chemistry Research (1994), 4(4), 267-272 (non-patent document 7) discloses the following compound as a 5-HT$_3$ antagonist.

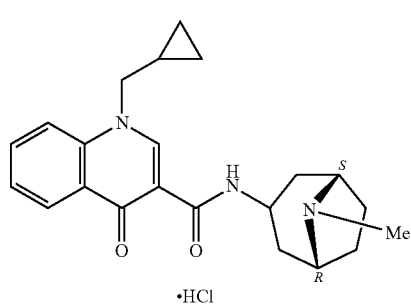

Zeitschrift fuer Naturforschung, B: Chemical Sciences (1988), 43(6), 769-777 (non-patent document 8) discloses the following compound.

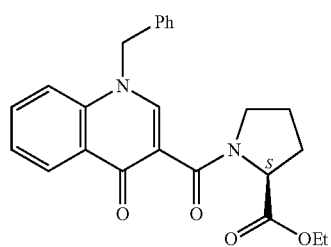

Zeitschrift fuer Naturforschung, B: Chemical Sciences (1987), 42(9), 1159-1166 (non-patent document 9) discloses the following compound.

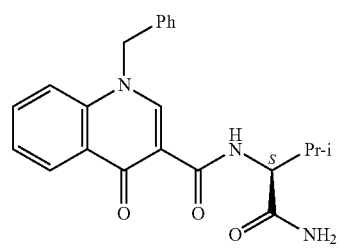

Journal of Heterocyclic Chemistry (1984), 21(1), 107-112 (non-patent document 10) discloses the following compound.

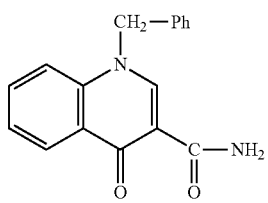 [SMILES: NC(=O)c1cn(Cc2ccccc2)c2ccccc2c1=O]

Furthermore, the following compound A (CAS Registry Number 1056677-22-5), compound B (CAS Registry Number 1056677-28-1), compound C (CAS Registry Number 1000376-79-3), compound D (CAS Registry Number 913534-04-0), compound E (CAS Registry Number 612512-36-4), compound F (CAS Registry Number 1031956-70-3), compound G (CAS Registry Number 757916-53-3) and compound H (CAS Registry Number 741223-39-2) are known.

compound A

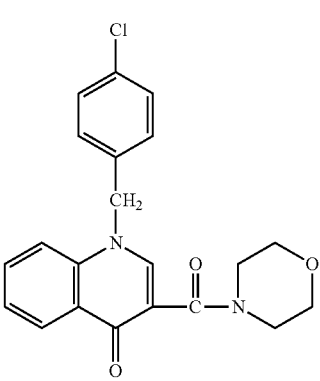

-continued compound B

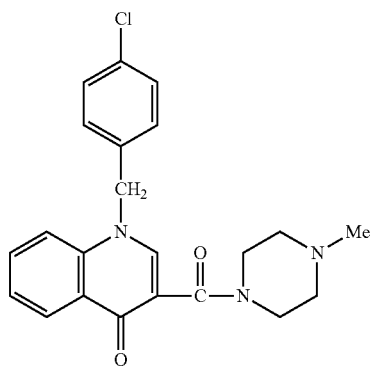

compound C

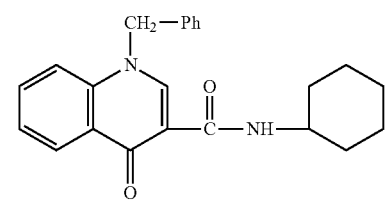

compound D

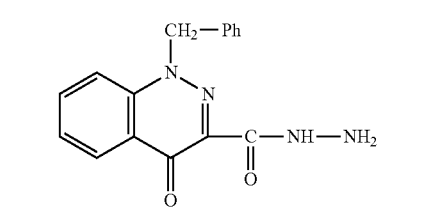

compound E

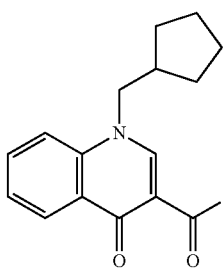

compound F

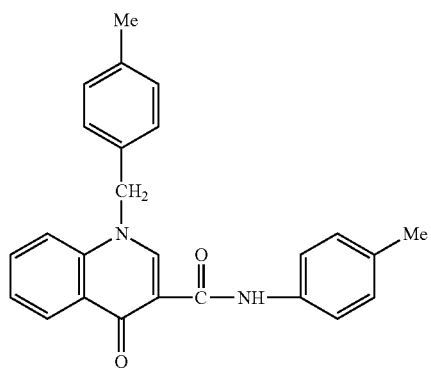

compound G

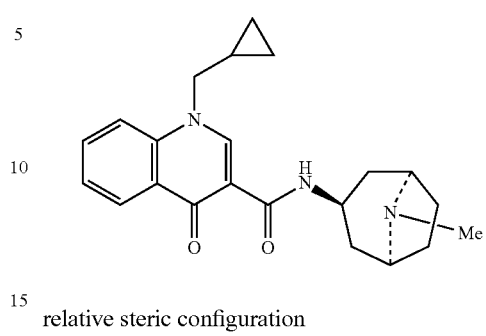

relative steric configuration compound H

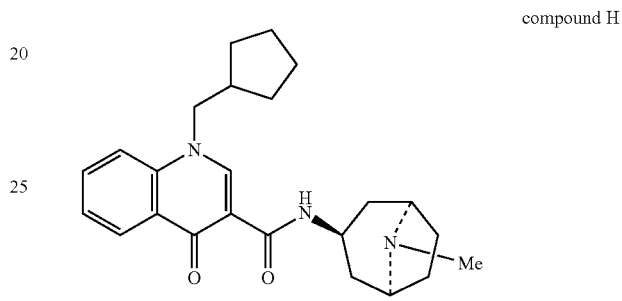

relative steric configuration

DOCUMENT LIST

Patent Documents patent document 1: WO 2007/067489
patent document 2: WO 2007/100366
patent document 3: WO 2008/002621
patent document 4: WO 2009/051715
patent document 5: WO 2009/094279
patent document 6: WO 2009/102574
patent document 7: WO 2009/102588
patent document 8: WO 2009/117283
patent document 9: WO 2009/134668
patent document 10: WO 2010/019391
patent document 11: WO 2010/042347
patent document 12: WO 2010/047990
patent document 13: WO 2010/059773
patent document 14: WO 2010/096338
patent document 15: WO 2009/053799
patent document 16: WO 2007/059108
patent document 17: EP 0560604
patent document 18: WO 91/05783
patent document 19: JP-A-H02-124871
patent document 20: JP-A-S64-61461
patent document 21: GB 1433774
patent document 22: WO 2011/062853
patent document 23: WO 2010/123716
patent document 24: WO 2011/025851
patent document 25: WO 2011/041143
patent document 26: WO 2011/049731
patent document 27: WO 2011/075371
patent document 28: WO 2011/084368
patent document 29: WO 2011/084371
patent document 30: WO 2011/159554
patent document 31: WO 2011/149801
patent document 32: WO 2011/137049
patent document 33: WO 2011/159553 patent document 34: WO 2011/163280
patent document 35: WO 2012/003147

Non-Patent Documents non-patent document 1: Nature Reviews Drug Discovery, 2007, 6, 721-733
non-patent document 2: Bioorganic and Medicinal Chemistry (2009), 17(5), 1948-1956
non-patent document 3: Oriental Journal of Chemistry (2007), 23(3), 935-942
non-patent document 4: Journal of Medicinal Chemistry (2007), 50(22), 5471-5484
non-patent document 5: Letters in Drug Design & Discovery (2007), 4(1), 15-19
non-patent document 6: Journal of Medicinal Chemistry (2006), 49(1), 70-79
non-patent document 7: Medicinal Chemistry Research (1994), 4(4), 267-272
non-patent document 8: Zeitschrift fuer Naturforschung, B: Chemical Sciences (1988), 43(6), 769-777
non-patent document 9: Zeitschrift fuer Naturforschung, B: Chemical Sciences (1987), 42(9), 1159-1166
non-patent document 10: Journal of Heterocyclic Chemistry (1984), 21(1), 107-112

SUMMARY OF THE INVENTION

Problems to be Solved by the Invention

The development of a heterocyclic compound having a cholinergic muscarinic M1 receptor (M1 receptor) positive allosteric modulator activity and useful as a prophylactic or therapeutic drug for Alzheimer's disease, schizophrenia, pain (pain), sleep disorder and the like is desired.

Means of Solving the Problems

The present inventors have conducted intensive studies in an attempt to solve the aforementioned problems and found that a compound represented by the following formula (I) has a cholinergic muscarinic M1 receptor (M1 receptor) positive allosteric modulator activity, which resulted in the completion of the present invention.

Accordingly, the present invention relates to the following.
[1] A compound represented by the formula (I)

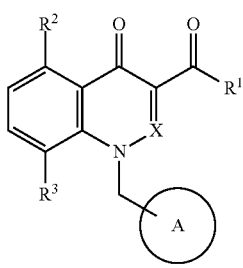

wherein
$R^1$ is an optionally substituted amino group or an optionally substituted cyclic amino group,
$R^2$ and $R^3$ are each independently a hydrogen atom or a substituent,
X is —CH= or —N=, and
ring A is an optionally substituted 5- to 10-membered ring, or a salt thereof,
provided that
(1) $R^1$ is not a methoxy(methyl)amino group;
(2) $R^1$ is not an amino group substituted by a substituent selected from an optionally substituted saturated azabicyclo ring group and a tetrazolyl group;
(3) $R^1$ is not a group represented by the formula

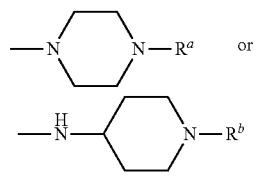

wherein $R^a$ is a phenyl lower alkyl group optionally having, as substituent(s) on the phenyl ring, 1 to 3 groups selected from the group consisting of a halogen atom, a lower alkyl group and a nitro group and optionally having, on the lower alkyl group, a hydroxyl group as a substituent, a hydrogen atom, a lower alkyl group, a benzoyl lower alkyl group, a phenyl lower alkenyl group, a benzoyl group optionally having, on the phenyl ring, a lower alkoxy group as a substituent, or a phenyl group, and
$R^b$ is a hydrogen atom or a phenyl lower alkyl group;
(4) $R^1$ is not a group represented by the formula

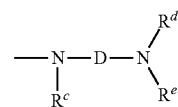

wherein D is an alkylene group or an alkylene group discontinued by at least one double bond,
$R^c$ is a hydrogen atom or a lower alkyl group,
a partial structure

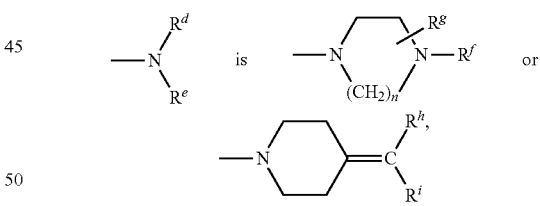

$R^f$ is a phenyl group, a nitrogen atom-containing heteroaryl group or a diphenylmethyl group,
$R^g$ is a hydrogen atom or a lower alkyl group,
n is 2 or 3,
$R^h$ and $R^i$ are each a phenyl group,
the phenyl group or phenyl moiety in the definitions of $R^f$, $R^h$ and $R^i$ is optionally substituted by 1 to 3 halogen atoms, a lower alkyl group, a trifluoromethyl group, a lower alkoxy group or a hydroxyl group;
(5) ring A is not an unsubstituted phenyl group; and
(6) when both $R^2$ and $R^3$ are hydrogen atoms, ring A is not an unsubstituted $C_{3-6}$ cycloalkyl group, or a phenyl group having a halogen atom or a methyl group at the 4-position (sometimes to be abbreviated as "compound (I)" in the present specification).

[2] A compound represented by the formula (I)

$$\text{(I)}$$

[Structure: a quinolinone/cinnolinone core with substituents R², R³ on the benzene ring, a C(=O)R¹ group at the 3-position, X (=CH– or =N–) in the ring, and an N-CH₂-(ring A) at the 1-position]

wherein
R¹ is an optionally substituted amino group or an optionally substituted cyclic amino group,
R² and R³ are each independently a hydrogen atom or a substituent,
X is —CH= or —N=, and
ring A is an optionally substituted 5- to 10-membered ring, or a salt thereof,
provided that
(1) R¹ is not a methoxy(methyl)amino group;
(2) R¹ is not an amino group substituted by a substituent selected from an optionally substituted saturated azabicyclo ring group and a tetrazolyl group;
(3) R¹ is not a group represented by the formula —N(piperazine)N—R^a   or   —NH—(piperidine)N—R^b wherein R^a is a phenyl lower alkyl group optionally having, as substituent(s) on the phenyl ring, 1 to 3 groups selected from the group consisting of a halogen atom, a lower alkyl group and a nitro group and optionally having, on the lower alkyl group, a hydroxyl group as a substituent, a hydrogen atom, a lower alkyl group, a benzoyl lower alkyl group, a phenyl lower alkenyl group, a benzoyl group optionally having, on the phenyl ring, a lower alkoxy group as a substituent, or a phenyl group, and
R^b is a hydrogen atom or a phenyl lower alkyl group;
(4) R¹ is not a group represented by the formula —N(R^c)—D—N(R^d)(R^e)

wherein D is an alkylene group or an alkylene group discontinued by at least one double bond,
R^c is a hydrogen atom or a lower alkyl group,
a partial structure —N(R^d)(R^e) is —N(piperazine with CH₂)ₙ N—R^f or —N(piperidine)=C(R^h)(R^i), R^f is a phenyl group, a nitrogen atom-containing heteroaryl group or a diphenylmethyl group,
R^g is a hydrogen atom or a lower alkyl group,
n is 2 or 3,
R^h and R^i are each a phenyl group,
the phenyl group or phenyl moiety in the definitions of R^f, R^h and R^i is optionally substituted by 1 to 3 halogen atoms, a lower alkyl group, a trifluoromethyl group, a lower alkoxy group or a hydroxyl group;
(5) ring A is not an unsubstituted phenyl group;
(6) when both R² and R³ are hydrogen atoms, ring A is not an unsubstituted $C_{3-6}$ cycloalkyl group, or a phenyl group having a halogen atom or a methyl group at the 4-position;
(7) R² is not an amino group; and
(8) the following compounds are excluded
(i) N-cyclohexyl-1,4-dihydro-1-[(4-methoxyphenyl)methyl]-4-oxo-3-quinolinecarboxamide, and
(ii) 1,4-dihydro-1-[(4-methoxyphenyl)methyl]-N-(2-methylphenyl)-4-oxo-3-quinolinecarboxamide.
[3] The compound of [1] or [2], wherein R¹ is
(a) an amino group optionally substituted by 1 or 2 substituents selected from
(1) an amino group,
(2) a $C_{1-6}$ alkyl group optionally substituted by 1 to 3 substituents selected from
(i) a hydroxyl group, (ii) a $C_{1-3}$ alkoxy group, (iii) a $C_{3-6}$ cycloalkyl group substituted by 1 to 3 hydroxyl groups, (iv) a phenyl group, (v) a furyl group, (vi) a tetrahydrofuranyl group, (vii) a piperidino group and (viii) a morpholino group,
(3) a $C_{3-6}$ cycloalkyl group optionally substituted by 1 to 3 substituents selected from a halogen atom, a hydroxyl group and a hydroxymethyl group,
(4) a 4- to 10-membered cyclic amino group,
(5) a phenyl group optionally substituted by 1 to 3 substituents selected from a halogen atom, a $C_{1-6}$ alkyl group optionally substituted by 1 to 3 halogen atoms and a hydroxymethyl group,
(6) a dihydroindenyl group substituted by 1 to 3 hydroxyl groups,
(7) a pyrazolyl group,
(8) a tetrahydrofuranyl group, and
(9) a tetrahydropyranyl group substituted by 1 to 3 hydroxyl groups, or
(b) a 4- to 10-membered cyclic amino group optionally substituted by 1 to 3 substituents selected from a hydroxyl group and a hydroxymethyl group,
R² and R³ are the same and each is a hydrogen atom or a halogen atom, or
R² is a hydrogen atom, and R³ is a halogen atom, or a $C_{1-3}$ alkoxy group substituted by 1 to 3 halogen atoms,
X is —CH= or —N=, and
ring A is a phenyl group wherein the 4-position is substituted by a substituent selected from
(i) a $C_{1-3}$ alkyl group substituted by 1 to 3 halogen atoms, (ii) a $C_{1-3}$ alkoxy group, (iii) a carbamoyl group, (iv) a pyrazolyl group optionally substituted by 1 to 3 $C_{1-3}$ alkyl groups and (v) a pyridyl group substituted by 1 to 3 $C_{1-3}$ alkyl groups,
or a salt thereof.

[3A] The compound of [3] or a salt thereof, excluding the following compounds:
(i) N-cyclohexyl-1,4-dihydro-1-[(4-methoxyphenyl)methyl]-4-oxo-3-quinolinecarboxamide, and
(ii) 1,4-dihydro-1-[(4-methoxyphenyl)methyl]-N-(2-methylphenyl)-4-oxo-3-quinolinecarboxamide.

[3B] The compound of [3] wherein the 4- to 10-membered cyclic amino group is a 4- to 7-membered cyclic amino group, or a salt thereof.

[3C] The compound of [3B] or a salt thereof, excluding the following compounds:
(i) N-cyclohexyl-1,4-dihydro-1-[(4-methoxyphenyl)methyl]-4-oxo-3-quinolinecarboxamide, and
(ii) 1,4-dihydro-1-[(4-methoxyphenyl)methyl]-N-(2-methylphenyl)-4-oxo-3-quinolinecarboxamide.

[3D] The compound of [1] or [2], wherein $R^1$ is
(a) an amino group optionally substituted by 1 or 2 substituents selected from
(1) an amino group,
(2) a $C_{1-6}$ alkyl group optionally substituted by 1 to 3 substituents selected from
(i) a hydroxyl group, (ii) a $C_{1-3}$ alkoxy group, (iii) a $C_{3-6}$ cycloalkyl group substituted by 1 to 3 hydroxyl groups, (iv) a phenyl group, (v) a furyl group, (vi) a tetrahydrofuranyl group, (vii) a piperidino group and (viii) a morpholino group,
(3) a $C_{3-6}$ cycloalkyl group optionally substituted by 1 to 3 substituents selected from a halogen atom, a hydroxyl group and a hydroxymethyl group,
(4) a piperidino group,
(5) a phenyl group optionally substituted by 1 to 3 substituents selected from a halogen atom, a $C_{1-6}$ alkyl group optionally substituted by 1 to 3 halogen atoms and a hydroxymethyl group,
(6) a dihydroindenyl group substituted by 1 to 3 hydroxyl groups,
(7) a pyrazolyl group,
(8) a tetrahydrofuranyl group, and
(9) a tetrahydropyranyl group substituted by 1 to 3 hydroxyl groups, or
(b)
(1) an azetidin-1-yl group substituted by 1 to 3 hydroxyl groups,
(2) a pyrrolidin-1-yl group substituted by 1 to 3 hydroxymethyl groups,
(3) a piperidino group optionally substituted by 1 to 3 hydroxyl groups, or
(4) a 1,3-dihydro-2H-isoindol-2-yl group,
$R^2$ and $R^3$ are the same and each is a hydrogen atom or a halogen atom, or
$R^2$ is a hydrogen atom, and $R^3$ is a halogen atom, or a $C_{1-3}$ alkoxy group substituted by 1 to 3 halogen atoms,
X is —CH= or —N=, and
ring A is a phenyl group wherein the 4-position is substituted by a substituent selected from
(i) a $C_{1-3}$ alkyl group substituted by 1 to 3 halogen atoms, (ii) a $C_{1-3}$ alkoxy group, (iii) a carbamoyl group, (iv) a pyrazolyl group optionally substituted by 1 to 3 $C_{1-3}$ alkyl groups and (v) a pyridyl group substituted by 1 to 3 $C_{1-3}$ alkyl groups, or a salt thereof.

[3E] The compound of [3D] or a salt thereof, excluding the following compounds:
(i) N-cyclohexyl-1,4-dihydro-1-[(4-methoxyphenyl)methyl]-4-oxo-3-quinolinecarboxamide, and
(ii) 1,4-dihydro-1-[(4-methoxyphenyl)methyl]-N-(2-methylphenyl)-4-oxo-3-quinolinecarboxamide.

[3F] The compound of [1] or [2], wherein $R^1$ is
(a) an amino group optionally substituted by 1 or 2 substituents selected from
(1) an amino group,
(2) a $C_{1-6}$ alkyl group optionally substituted by 1 to 3 substituents selected from
(i) a hydroxyl group, (ii) a $C_{1-3}$ alkoxy group, (iii) a $C_{3-6}$ cycloalkyl group substituted by 1 to 3 hydroxyl groups, (iv) a phenyl group, (v) a furyl group, (vi) a piperidino group and (vii) a morpholino group,
(3) a $C_{3-6}$ cycloalkyl group optionally substituted by 1 to 3 substituents selected from a halogen atom, a hydroxyl group and a hydroxymethyl group,
(4) a 4- to 10-membered cyclic amino group,
(5) a phenyl group optionally substituted by 1 to 3 substituents selected from a halogen atom, a $C_{1-6}$ alkyl group optionally substituted by 1 to 3 halogen atoms and a hydroxymethyl group,
(6) a dihydroindenyl group substituted by 1 to 3 hydroxyl groups,
(7) a tetrahydrofuranyl group, and
(8) a tetrahydropyranyl group substituted by 1 to 3 hydroxyl groups, or
(b) a 4- to 10-membered cyclic amino group optionally substituted by 1 to 3 substituents selected from a hydroxyl group and a hydroxymethyl group,
$R^2$ and $R^3$ are the same and each is a hydrogen atom or a halogen atom, or
$R^2$ is a hydrogen atom, and $R^3$ is a halogen atom, or a $C_{1-3}$ alkoxy group substituted by 1 to 3 halogen atoms,
X is —CH=, and
ring A is a phenyl group wherein the 4-position is substituted by a substituent selected from
(i) a $C_{1-3}$ alkyl group substituted by 1 to 3 halogen atoms, (ii) a $C_{1-3}$ alkoxy group, (iii) a carbamoyl group, (iv) a pyrazolyl group optionally substituted by 1 to 3 $C_{1-3}$ alkyl groups and (v) a pyridyl group substituted by 1 to 3 $C_{1-3}$ alkyl groups, or a salt thereof.

[3G] The compound of [3F] or a salt thereof, excluding the following compounds:
(i) N-cyclohexyl-1,4-dihydro-1-[(4-methoxyphenyl)methyl]-4-oxo-3-quinolinecarboxamide, and
(ii) 1,4-dihydro-1-[(4-methoxyphenyl)methyl]-N-(2-methylphenyl)-4-oxo-3-quinolinecarboxamide.

[3H] The compound of [3F], wherein the 4- to 10-membered cyclic amino group is a 4- to 7-membered cyclic amino group, or a salt thereof.

[3I] The compound of [3H] or a salt thereof, excluding the following compounds:
(i) N-cyclohexyl-1,4-dihydro-1-[(4-methoxyphenyl)methyl]-4-oxo-3-quinolinecarboxamide, and
(ii) 1,4-dihydro-1-[(4-methoxyphenyl)methyl]-N-(2-methylphenyl)-4-oxo-3-quinolinecarboxamide.

[3J] The compound of [3F], wherein, in the definition of $R^1$,
(a) (4) the 4- to 10-membered cyclic amino group is a piperidino group, and
(b) the 4- to 10-membered cyclic amino group optionally substituted by 1 to 3 substituents selected from a hydroxyl group and a hydroxymethyl group is
(1) an azetidin-1-yl group substituted by 1 to 3 hydroxyl groups,
(2) a pyrrolidin-1-yl group substituted by 1 to 3 hydroxymethyl groups,
(3) a piperidino group optionally substituted by 1 to 3 hydroxyl groups, or
(4) a 1,3-dihydro-2H-isoindol-2-yl group,
or a salt thereof.

[3K] The compound of [3J] or a salt thereof, excluding the following compounds:
(i) N-cyclohexyl-1,4-dihydro-1-[(4-methoxyphenyl)methyl]-4-oxo-3-quinolinecarboxamide, and
(ii) 1,4-dihydro-1-[(4-methoxyphenyl)methyl]-N-(2-methylphenyl)-4-oxo-3-quinolinecarboxamide.

[3L] The compound of [1] or [2], wherein $R^1$ is
(a) an amino group optionally substituted by 1 or 2 substituents selected from
(1) an amino group,
(2) a $C_{1-6}$ alkyl group optionally substituted by 1 to 3 substituents selected from
(i) a hydroxyl group, (ii) a $C_{1-3}$ alkoxy group, (iii) a $C_{3-6}$ cycloalkyl group substituted by 1 to 3 hydroxyl groups, (iv) a phenyl group and (v) a tetrahydrofuranyl group,
(3) a $C_{3-6}$ cycloalkyl group optionally substituted by 1 to 3 substituents selected from a hydroxyl group and a hydroxymethyl group,
(4) a 4- to 10-membered cyclic amino group,
(5) a phenyl group optionally substituted by 1 to 3 substituents selected from a $C_{1-6}$ alkyl group and a hydroxymethyl group,
(6) a dihydroindenyl group substituted by 1 to 3 hydroxyl groups,
(7) a pyrazolyl group, and
(8) a tetrahydropyranyl group substituted by 1 to 3 hydroxyl groups, or
(b) a 4- to 10-membered cyclic amino group optionally substituted by 1 to 3 substituents selected from a hydroxyl group and a hydroxymethyl group,
$R^2$ and $R^3$ are the same and each is a hydrogen atom,
X is —N═, and
ring A is a phenyl group wherein the 4-position is substituted by a substituent selected from (i) a $C_{1-3}$ alkoxy group and (ii) a carbamoyl group,
or a salt thereof.

[3M] The compound of [3L], wherein the 4- to 10-membered cyclic amino group is a 4- to 7-membered cyclic amino group, or a salt thereof.

[3N] The compound of [3M], wherein, in the definition of $R^1$,
(a) (4) the 4- to 7-membered cyclic amino group is a piperidino group, and
(b) the 4- to 7-membered cyclic amino group optionally substituted by 1 to 3 substituents selected from a hydroxyl group and a hydroxymethyl group is
(1) an azetidin-1-yl group substituted by 1 to 3 hydroxyl groups,
(2) a pyrrolidin-1-yl group substituted by 1 to 3 hydroxymethyl groups, or
(3) a piperidino group,
or a salt thereof.

[4] The compound of [1] or [2], wherein $R^1$ is an amino group optionally substituted by one substituent selected from
(1) an amino group,
(2) a $C_{1-6}$ alkyl group optionally substituted by 1 to 3 substituents selected from
(i) a hydroxyl group, (ii) a $C_{1-3}$ alkoxy group and (iii) a $C_{3-6}$ cycloalkyl group substituted by 1 to 3 hydroxyl groups,
(3) a $C_{3-6}$ cycloalkyl group optionally substituted by 1 to 3 substituents selected from a halogen atom, a hydroxyl group and a hydroxymethyl group,
(4) a piperidino group,
(5) a phenyl group optionally substituted by 1 to 3 substituents selected from a $C_{1-6}$ alkyl group optionally substituted by 1 to 3 halogen atoms, and
(6) a tetrahydropyranyl group substituted by 1 to 3 hydroxyl groups,
$R^2$ and $R^3$ are the same and each is a hydrogen atom or a halogen atom, or
$R^2$ is a hydrogen atom, and $R^3$ is a halogen atom,
X is —CH═ or —N═, and
ring A is a phenyl group wherein the 4-position is substituted by a substituent selected from
(i) a $C_{1-3}$ alkyl group substituted by 1 to 3 halogen atoms, (ii) a $C_{1-3}$ alkoxy group, (iii) a carbamoyl group, (iv) a pyrazolyl group optionally substituted by 1 to 3 $C_{1-3}$ alkyl groups and (v) a pyridyl group substituted by 1 to 3 $C_{1-3}$ alkyl groups,
or a salt thereof.

[4A] The compound of [4], wherein X is —CH═, or a salt thereof.

[4B] The compound of [4A] or a salt thereof, excluding the following compounds:
(i) N-cyclohexyl-1,4-dihydro-1-[(4-methoxyphenyl)methyl]-4-oxo-3-quinolinecarboxamide, and
(ii) 1,4-dihydro-1-[(4-methoxyphenyl)methyl]-N-(2-methylphenyl)-4-oxo-3-quinolinecarboxamide.

[4C] The compound of [4], wherein X is —N═, or a salt thereof.

[5] The compound of [1] or [2], wherein $R^1$ is an amino group substituted by one substituent selected from
(1) an amino group,
(2) a $C_{3-6}$ cycloalkyl group substituted by 1 to 3 substituents selected from a halogen atom and a hydroxyl group, and
(3) a tetrahydropyranyl group substituted by 1 to 3 hydroxyl groups,
$R^2$ and $R^3$ are the same and each is a hydrogen atom or a halogen atom, or
$R^2$ is a hydrogen atom, and $R^3$ is a halogen atom,
X is —CH═ or —N═, and
ring A is a phenyl group wherein the 4-position is substituted by a substituent selected from
(i) a $C_{1-3}$ alkoxy group, (ii) a carbamoyl group, (iii) a pyrazolyl group optionally substituted by 1 to 3 $C_{1-3}$ alkyl groups and (iv) a pyridyl group substituted by 1 to 3 $C_{1-3}$ alkyl groups,
or a salt thereof.

[5A] The compound of [5], wherein X is —CH═, or a salt thereof.

[5B] The compound of [5], wherein X is —N═, or a salt thereof.

[5C] The compound of [5], wherein $R^1$ is an amino group substituted by one substituent selected from a $C_{3-6}$ cycloalkyl group substituted by 1 to 3 hydroxyl groups and a tetrahydropyranyl group substituted by 1 to 3 hydroxyl groups,
or a salt thereof.

[5D] The compound of [5C], wherein X is —CH═, or a salt thereof.

[5E] The compound of [5C], wherein X is —N═, or a salt thereof.

[5F] The compound of [5], wherein $R^1$ is an amino group substituted by one $C_{3-6}$ cycloalkyl group substituted by 1 to 3 hydroxyl groups, or a salt thereof.

[5G] The compound of [5F], wherein X is —CH═, or a salt thereof.

[5H] The compound of [5F], wherein X is —N═, or a salt thereof.

[5I] The compound of [1] or [2], wherein $R^1$ is an amino group substituted by one substituent selected from a $C_{3-6}$ cycloalkyl group substituted by 1 to 3 hydroxyl groups and a tetrahydropyranyl group substituted by 1 to 3 hydroxyl groups,
$R^2$ and $R^3$ are the same and each is a hydrogen atom or a halogen atom, or
$R^2$ is a hydrogen atom, and $R^3$ is a halogen atom,
X is —CH═ or —N═, and ring A is a phenyl group wherein the 4-position is substituted by a substituent selected from
(i) a $C_{1-3}$ alkoxy group, (ii) a carbamoyl group and (iii) a pyrazolyl group optionally substituted by 1 to 3 $C_{1-3}$ alkyl groups,
or a salt thereof.

[5J] The compound of [1] or [2], wherein $R^1$ is an amino group substituted by one substituent selected from a $C_{3-6}$ cycloalkyl group substituted by 1 to 3 hydroxyl groups and a tetrahydropyranyl group substituted by 1 to 3 hydroxyl groups,
$R^2$ and $R^3$ are the same and each is a hydrogen atom or a halogen atom, or
$R^2$ is a hydrogen atom, and $R^3$ is a halogen atom,
X is —CH=, and
ring A is a phenyl group wherein the 4-position is substituted by a substituent selected from
(i) a $C_{1-3}$ alkoxy group and (ii) a pyrazolyl group optionally substituted by 1 to 3 $C_{1-3}$ alkyl groups,
or a salt thereof.

[5K] A compound selected from
5,8-difluoro-N-[(1,2-trans)-2-hydroxycyclohexyl]-4-oxo-1-[4-(1H-pyrazol-1-yl)benzyl]-1,4-dihydroquinoline-3-carboxamide,
N-[(1,2-trans)-2-hydroxycyclohexyl]-4-oxo-1-[4-(1H-pyrazol-1-yl)benzyl]-1,4-dihydrocinnoline-3-carboxamide,
1-(4-carbamoylbenzyl)-N-((1S,2S)-2-hydroxycyclohexyl)-4-oxo-1,4-dihydroquinoline-3-carboxamide,
1,5-anhydro-2,3-dideoxy-3-({[5,8-difluoro-1-(4-methoxybenzyl)-4-oxo-1,4-dihydroquinolin-3-yl]carbonyl}amino)-DL-threo-pentitol,
5,8-difluoro-N-[(1,2-trans)-2-hydroxycyclohexyl]-1-(4-methoxybenzyl)-4-oxo-1,4-dihydroquinoline-3-carboxamide,
5,8-difluoro-N-[(1S,2S)-2-hydroxycyclohexyl]-1-(4-methoxybenzyl)-4-oxo-1,4-dihydroquinoline-3-carboxamide,
1,5-anhydro-2,3-dideoxy-3-({[1-(4-methoxybenzyl)-4-oxo-1,4-dihydrocinnolin-3-yl]carbonyl}amino)-DL-threo-pentitol,
1-(4-carbamoylbenzyl)-N-[(1,2-trans)-2-hydroxycyclohexyl]-4-oxo-1,4-dihydroquinoline-3-carboxamide,
1-(4-carbamoylbenzyl)-N-[(1,2-trans)-2-hydroxycyclohexyl]-4-oxo-1,4-dihydrocinnoline-3-carboxamide,
1-(4-carbamoylbenzyl)-N-[(1S,2S)-2-hydroxycyclohexyl]-4-oxo-1,4-dihydroquinoline-3-carboxamide,
8-fluoro-N-[(1,2-trans)-2-hydroxycyclohexyl]-4-oxo-1-[4-(1H-pyrazol-1-yl)benzyl]-1,4-dihydroquinoline-3-carboxamide,
N-[(1,2-trans)-5,5-difluoro-2-hydroxycyclohexyl]-5,8-difluoro-1-(4-methoxybenzyl)-4-oxo-1,4-dihydroquinoline-3-carboxamide,
N-[(1,2-trans)-2-hydroxycyclohexyl]-4-oxo-1-[4-(1H-pyrazol-5-yl)benzyl]-1,4-dihydroquinoline-3-carboxamide,
1-(4-carbamoylbenzyl)-N-[(1,2-trans)-2-fluorocyclohexyl]-4-oxo-1,4-dihydroquinoline-3-carboxamide,
8-fluoro-N-[(1,2-trans)-2-hydroxycyclopentyl]-4-oxo-1-[4-(1H-pyrazol-1-yl)benzyl]-1,4-dihydroquinoline-3-carboxamide,
N-[(1,2-trans)-2-hydroxycyclopentyl]-1-[4-(2-methylpyridin-4-yl)benzyl]-4-oxo-1,4-dihydroquinoline-3-carboxamide, and
1-[4-(1,3-dimethyl-1H-pyrazol-4-yl)benzyl]-N-[(1,2-trans)-2-hydroxycyclopentyl]-4-oxo-1,4-dihydroquinoline-3-carboxamide,
or a salt thereof.

[5L] A compound selected from
1-(4-carbamoylbenzyl)-N-[(1S,2S)-2-hydroxycyclohexyl]-4-oxo-1,4-dihydroquinoline-3-carboxamide,
1,5-anhydro-2,3-dideoxy-3-({[5,8-difluoro-1-(4-methoxybenzyl)-4-oxo-1,4-dihydroquinolin-3-yl]carbonyl}amino)-DL-threo-pentitol,
5,8-difluoro-N-[(1,2-trans)-2-hydroxycyclohexyl]-1-(4-methoxybenzyl)-4-oxo-1,4-dihydroquinoline-3-carboxamide,
1-(4-carbamoylbenzyl)-N-[(1S,2S)-2-hydroxycyclohexyl]-4-oxo-1,4-dihydroquinoline-3-carboxamide,
8-fluoro-N-[(1,2-trans)-2-hydroxycyclopentyl]-4-oxo-1-[4-(1H-pyrazol-1-yl)benzyl]-1,4-dihydroquinoline-3-carboxamide, and
1-[4-(1,3-dimethyl-1H-pyrazol-4-yl)benzyl]-N-[(1,2-trans)-2-hydroxycyclopentyl]-4-oxo-1,4-dihydroquinoline-3-carboxamide,
or a salt thereof.

[5M] A compound selected from
1,5-anhydro-2,3-dideoxy-3-({[5,8-difluoro-1-(4-methoxybenzyl)-4-oxo-1,4-dihydroquinolin-3-yl]carbonyl}amino)-DL-threo-pentitol,
5,8-difluoro-N-[(1,2-trans)-2-hydroxycyclohexyl]-1-(4-methoxybenzyl)-4-oxo-1,4-dihydroquinoline-3-carboxamide,
8-fluoro-N-[(1,2-trans)-2-hydroxycyclopentyl]-4-oxo-1-[4-(1H-pyrazol-1-yl)benzyl]-1,4-dihydroquinoline-3-carboxamide, and
1-[4-(1,3-dimethyl-1H-pyrazol-4-yl)benzyl]-N-[(1,2-trans)-2-hydroxycyclopentyl]-4-oxo-1,4-dihydroquinoline-3-carboxamide,
or a salt thereof.

[6] 1,5-Anhydro-2,3-dideoxy-3-({[5,8-difluoro-1-(4-methoxybenzyl)-4-oxo-1,4-dihydroquinolin-3-yl]carbonyl}amino)-DL-threo-pentitol, or a salt thereof.

[7] 5,8-Difluoro-N-[(1,2-trans)-2-hydroxycyclohexyl]-1-(4-methoxybenzyl)-4-oxo-4-dihydroquinoline-3-carboxamide, or a salt thereof.

[8] 8-Fluoro-N-[(1,2-trans)-2-hydroxycyclopentyl]-4-oxo-1-[4-(1H-pyrazol-1-yl)benzyl]-1,4-dihydroquinoline-3-carboxamide, or a salt thereof.

[9] 1-[4-(1,3-Dimethyl-1H-pyrazol-4-yl)benzyl]-N-[(1,2-trans)-2-hydroxycyclopentyl]-4-oxo-1,4-dihydroquinoline-3-carboxamide,
or a salt thereof.

[10] A medicament comprising the compound of any one of [1] to [9], or a salt thereof.

[11] The medicament of [10], which is a cholinergic muscarinic M1 receptor positive allosteric modulator.

[11A] The medicament of [10], which is an M1 receptor function enhancer.

[12] The medicament of [10], which is a prophylactic or therapeutic drug for Alzheimer's disease, schizophrenia, pain or a sleep disorder.

[12A] The medicament of [10], which is a prophylactic or therapeutic drug for Alzheimer's disease, schizophrenia, pain or a sleep disorder.

[13] A method for the prophylaxis or treatment of Alzheimer's disease, schizophrenia, pain or a sleep disorder, comprising administering an effective amount of the compound of any one of [1] to [9] or a salt thereof to a mammal.

[13A] A method for the prophylaxis or treatment of Alzheimer's disease, schizophrenia, pain or a sleep disorder, comprising administering an effective amount of the compound of any one of [1] to [9] or a salt thereof to a mammal.

[14] Use of the compound of any one of [1] to [9] or a salt thereof for the production of a cholinergic muscarinic M1 receptor positive allosteric modulator.
[14A] Use of the compound of any one of [1] to [9] or a salt thereof for the production of an M1 receptor function enhancer.
[15] Use of the compound of any one of [1] to [9] or a salt thereof for the production of a prophylactic or therapeutic drug for Alzheimer's disease, schizophrenia, pain or a sleep disorder.
[15A] Use of the compound of any one of [1] to [9] or a salt thereof for the production of a prophylactic or therapeutic drug for Alzheimer's disease, schizophrenia, pain or a sleep disorder.
[16] The compound of any one of [1] to [9] or a salt thereof for use in cholinergic muscarinic M1 receptor positive allosteric modulation.
[16A] The compound of any one of [1] to [9] or a salt thereof for use in a cholinergic muscarinic M1 receptor positive allosteric modulate.
[16B] The compound of any one of [1] to [9] or a salt thereof for use in enhancing an M1 receptor function.
[17] The compound of any one of [1] to [9] or a salt thereof for use in the prophylaxis or treatment of Alzheimer's disease, schizophrenia, pain or a sleep disorder.
[17A] The compound of any one of [1] to [9] or a salt thereof for use in the prophylaxis or treatment of Alzheimer's disease, schizophrenia, pain or a sleep disorder.
[18] A method of cholinergic muscarinic M1 receptor positive allosteric modulation, comprising administering an effective amount of the compound of any one of [1] to [9] or a salt thereof to a mammal.
[18A] A method of enhancing an M1 receptor function, comprising administering an effective amount of the compound of any one of [1] to [9] or a salt thereof to a mammal.

Effect of the Invention

The compound of the present invention has a cholinergic muscarinic M1 receptor positive allosteric modulator activity, and is useful as a prophylactic or therapeutic drug for, for example, Alzheimer's disease, schizophrenia, pain (pain), sleep disorder and the like.

DETAILED DESCRIPTION OF THE INVENTION

The present invention is explained in detail in the following.

In the present specification, the "lower" means 1 to 6 carbon atoms.

Examples of the "halogen atom" include a fluorine atom, a chlorine atom, a bromine atom and an iodine atom.

The "$C_{1-3}$ alkyl group" means a straight chain or branched chain $C_{1-3}$ alkyl group, and examples thereof include methyl, ethyl, propyl and isopropyl.

The "$C_{1-6}$ alkyl group" means a straight chain or branched chain $C_{1-6}$ alkyl group, and examples thereof include methyl, ethyl, propyl, isopropyl, butyl, isobutyl, sec-butyl, tert-butyl, pentyl, isopentyl, neopentyl, tert-pentyl, 1,2-dimethylpropyl, hexyl, 2-methylpentyl, 3-methylpentyl, 1,2-dimethylbutyl, 1,2,2-trimethylpropyl and the like.

The "$C_{1-10}$ alkyl group" means a straight chain or branched chain $C_{1-10}$ alkyl group, and examples thereof include ethyl, propyl, isopropyl, butyl, isobutyl, sec-butyl, tert-butyl, pentyl, isopentyl, neopentyl, tert-pentyl, 1,2-dimethylpropyl, hexyl, 2-methylpentyl, 3-methylpentyl, 1,2-dimethylbutyl, 1,2,2-trimethylpropyl, heptyl, octyl, nonyl, decyl and the like.

The "$C_{2-10}$ alkyl group" means a straight chain or branched chain $C_{2-10}$ alkyl group, and examples thereof include ethyl, propyl, isopropyl, butyl, isobutyl, sec-butyl, tert-butyl, pentyl, isopentyl, neopentyl, tert-pentyl, 1,2-dimethylpropyl, hexyl, 2-methylpentyl, 3-methylpentyl, 1,2-dimethylbutyl, 1,2,2-trimethylpropyl, heptyl, octyl, nonyl, decyl and the like.

The "$C_{1-3}$ alkyl group substituted by 1 to 3 halogen atoms" means a straight chain or branched chain $C_{1-3}$ alkyl group substituted by 1 to 3 halogen atoms (e.g., a fluorine atom, a chlorine atom, a bromine atom, an iodine atom), and examples thereof include fluoromethyl, difluoromethyl, trifluoromethyl, 1,1-difluoroethyl, 2,2-difluoroethyl, chloromethyl, 2-chloroethyl, bromomethyl, 2-bromoethyl and the like.

The "$C_{2-6}$ alkenyl group" means a straight chain or branched chain $C_{2-6}$ alkenyl group, and examples thereof include vinyl, allyl, 1-propenyl, 2-propenyl, 1-butenyl, 2-butenyl, 3-butenyl and the like.

The "$C_{1-6}$ alkoxy group" means a straight chain or branched chain $C_{1-6}$ alkoxy group, and examples thereof include methoxy, ethoxy, propoxy, isopropoxy, butoxy, isobutoxy, sec-butoxy, tert-butoxy, pentyloxy, isopentyloxy, neopentyloxy, tert-pentyloxy, 1,2-dimethylpropyloxy, hexyloxy, 2-methylpentyloxy, 3-methylpentyloxy, 1,2-dimethylbutyloxy, 1,2,2-trimethylpropyloxy and the like.

The "$C_{1-3}$ alkoxy group" means a straight chain or branched chain $C_{1-3}$ alkoxy group, and examples thereof include methoxy, ethoxy, propoxy and isopropoxy.

The "$C_{1-3}$ alkoxy group substituted by 1 to 3 halogen atoms" means a straight chain or branched chain $C_{1-3}$ alkoxy group substituted by 1 to 3 halogen atoms (e.g., a fluorine atom, a chlorine atom, a bromine atom, an iodine atom), and examples thereof include fluoromethoxy, difluoromethoxy, trifluoromethoxy, 1,1-difluoroethoxy, 2,2-difluoroethoxy, chloromethoxy, 2-chloroethoxy, bromomethoxy, 2-bromoethoxy and the like.

Examples of the "$C_{3-10}$ cycloalkyl group" include cyclopropyl, cyclobutyl, cyclopentyl, cyclohexyl, cycloheptyl and the like.

Examples of the "$C_{3-6}$ cycloalkyl group" include cyclopropyl, cyclobutyl, cyclopentyl and cyclohexyl.

Examples of the "$C_{3-6}$ cycloalkenyl group" include cyclopropenyl, cyclobutenyl, cyclopentenyl and cyclohexenyl.

Examples of the "$C_{6-14}$ aryl group" include phenyl, naphthyl (e.g., 1-naphthyl, 2-naphthyl), anthryl, phenanthryl and the like. Preferred is a $C_{6-10}$ aryl group such as phenyl, naphthyl and the like.

The "aromatic group" means an aromatic hydrocarbon group or an aromatic heterocyclic group.

Examples of the "aromatic hydrocarbon group" include $C_{6-14}$ aromatic hydrocarbon groups such as phenyl, naphthyl (e.g., 1-naphthyl, 2-naphthyl), anthryl, phenanthryl and the like.

Examples of the "aromatic heterocyclic group" include a 5- to 14-membered (preferably 5- to 10-membered) aromatic heterocyclic group containing 1 to 4 (preferably 1 to 3, more preferably 1 or 2) hetero atoms selected from a nitrogen atom, a sulfur atom and an oxygen atom. Examples thereof include monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, furazanyl, pyranyl and the like; fused polycyclic (preferably bicyclic or tricyclic) aromatic heterocyclic groups such as benzothienyl, benzofuranyl, benzimidazolyl, benzoxazolyl, benzothiazolyl, benzisothiazolyl, phenoxathiinyl, indolyl, isoindolyl, 1H-indazolyl, purinyl, 4H-quinolizinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like, and the like.

Preferable examples of the "aromatic group" include a phenyl group and a pyridyl group (e.g., 2-pyridyl, 3-pyridyl, 4-pyridyl).

Examples of the "heterocyclic group" include a 5- to 14-membered (preferably 5- to 10-membered) (monocyclic, bicyclic or tricyclic, preferably monocyclic or bicyclic) heterocyclic group containing 1 to 4 (preferably 1 to 3, more preferably 1 or 2) hetero atoms selected from a nitrogen atom, a sulfur atom and an oxygen atom. Examples thereof include monocyclic aromatic heterocyclic groups such as thienyl, furyl, pyrrolyl, imidazolyl, pyrazolyl, thiazolyl, isothiazolyl, oxazolyl, isoxazolyl, pyridyl, pyrazinyl, pyrimidinyl, pyridazinyl, 1,2,4-oxadiazolyl, 1,3,4-oxadiazolyl, 1,2,4-thiadiazolyl, 1,3,4-thiadiazolyl, triazolyl, tetrazolyl, furazanyl, pyranyl and the like; fused polycyclic (preferably bicyclic or tricyclic) aromatic heterocyclic groups such as benzothienyl, benzofuranyl, benzimidazolyl, benzoxazolyl, benzothiazolyl, benzoisothiazolyl, phenoxathiinyl, indolyl, isoindolyl, 1H-indazolyl, purinyl, 4H-quinolizinyl, isoquinolyl, quinolyl, phthalazinyl, naphthyridinyl, quinoxalinyl, quinazolinyl, cinnolinyl, carbazolyl, β-carbolinyl, phenanthridinyl, acridinyl, phenazinyl, phenothiazinyl, phenoxazinyl and the like; nonaromatic heterocyclic groups such as azetidinyl, pyrrolidinyl, tetrahydrofuryl, tetrahydrothienyl, piperidinyl, tetrahydropyranyl, morpholinyl, thiomorpholinyl, piperazinyl, azepanyl, diazepanyl (e.g., 1,4-diazepanyl), oxazepanyl (e.g., 1,4-oxazepanyl), oxazolidinyl, isoxazolidinyl, thiazolidinyl, isothiazolidinyl, imidazolidinyl, pyrazolidinyl, oxadiazolidinyl (e.g., 1,2,4-oxadiazolidinyl, 1,3,4-oxadiazolidinyl), thiadiazolidinyl (e.g., 1,2,4-thiadiazolidinyl, 1,3,4-thiadiazolidinyl), pyrrolinyl, oxazolinyl, isoxazolinyl, thiazolinyl, isothiazolinyl, imidazolinyl, pyrazolinyl, oxadiazolinyl (e.g., 1,2,4-oxadiazolinyl, 1,3,4-oxadiazolinyl), thiadiazolinyl (e.g., 1,2,4-thiadiazolinyl, 1,3,4-thiadiazolinyl), and the like, and the like.

Examples of the "cyclic amino group" include a 4- to 10-membered cyclic amino group, preferably a 4- to 7-membered cyclic amino group.

Examples of the "4- to 10-membered cyclic amino group" include a 4- to 10-membered cyclic amino group optionally containing, besides one nitrogen atom, 1 to 3 (preferably 1) hetero atoms selected from a nitrogen atom, a sulfur atom and an oxygen atom. Specific examples thereof include azetidin-1-yl, pyrrolidin-1-yl, piperidino, piperazin-1-yl, morpholino, thiomorpholino, hexahydroazepin-1-yl, 1,3-dihydro-2H-isoindol-2-yl and the like.

Examples of the "4- to 7-membered cyclic amino group" include a 4- to 7-membered cyclic amino group optionally containing, besides one nitrogen atom, 1 to 3 (preferably 1) hetero atoms selected from a nitrogen atom, a sulfur atom and an oxygen atom. Specific examples thereof include azetidin-1-yl, pyrrolidin-1-yl, piperidino, piperazin-1-yl, morpholino, thiomorpholino, hexahydroazepin-1-yl and the like.

Examples of the "nonaromatic heterocyclic group" include a 4- to 7-membered saturated or unsaturated (preferably saturated) nonaromatic heterocyclic group containing, 1 to 4 (preferably 1 to 3, more preferably 1 or 2) hetero atoms selected from a nitrogen atom, a sulfur atom and an oxygen atom, for example, azetidinyl, pyrrolidinyl, tetrahydrofuryl, tetrahydrothienyl, piperidinyl, tetrahydropyranyl, morpholinyl, thiomorpholinyl, piperazinyl, azepanyl, diazepanyl (e.g., 1,4-diazepanyl), oxazepanyl (e.g., 1,4-oxazepanyl), oxazolidinyl, isoxazolidinyl, thiazolidinyl, isothiazolidinyl, imidazolidinyl, pyrazolidinyl, oxadiazolidinyl (e.g., 1,2,4-oxadiazolidinyl, 1,3,4-oxadiazolidinyl), thiadiazolidinyl (e.g., 1,2,4-thiadiazolidinyl, 1,3,4-thiadiazolidinyl), pyrrolinyl, oxazolinyl, isoxazolinyl, thiazolinyl, isothiazolinyl, imidazolinyl, pyrazolinyl, oxadiazolinyl (e.g., 1,2,4-oxadiazolinyl, 1,3,4-oxadiazolinyl), thiadiazolinyl (e.g., 1,2,4-thiadiazolinyl, 1,3,4-thiadiazolinyl) and the like.

$R^1$ is an optionally substituted amino group or an optionally substituted cyclic amino group.

The "optionally substituted amino group" for $R^1$ is a group represented by the formula —$N(R^4)(R^5)$ wherein $R^4$ and $R^5$ are each independently a hydrogen atom or a substituent.

Examples of the substituent for $R^4$ or $R^5$ include
(1) an amino group,
(2) an optionally substituted $C_{1-10}$ alkyl group,
(3) an optionally substituted $C_{2-6}$ alkenyl group,
(4) an optionally substituted $C_{1-6}$ alkoxy group,
(5) an optionally substituted $C_{3-10}$ cycloalkyl group,
(6) an optionally substituted $C_{3-6}$ cycloalkenyl group,
(7) an optionally substituted cyclic amino group (e.g., a piperidino group),
(8) an optionally substituted aromatic group (e.g., a phenyl group, a pyrazolyl group),
(9) an optionally substituted dihydroindenyl group,
(10) an optionally substituted nonaromatic heterocyclic group (e.g., a tetrahydrofuryl group, a tetrahydropyranyl group) and the like.

The aforementioned "$C_{1-10}$ alkyl group", "$C_{2-6}$ alkenyl group" and "$C_{1-6}$ alkoxy group" are optionally substituted by 1 to 3 substituents selected from, for example, the following substituent group A.

[Substituent Group A]
(a) a halogen atom,
(b) a cyano group,
(c) a hydroxyl group,
(d) a nitro group,
(e) a formyl group,
(f) a $C_{1-6}$ alkoxy group (preferably, a $C_{1-3}$ alkoxy group),
(g) a $C_{3-6}$ cycloalkyl group optionally substituted by 1 to 3 hydroxyl groups,
(h) a $C_{6-14}$ aryl group,
(i) a cyclic amino group (e.g., a piperidino group, a morpholino group),
(j) a heterocyclic group (e.g., a furyl group, a tetrahydrofuranyl group),
(k) a $C_{1-6}$ alkyl-carbonyl group,
(l) an amino group, and
(m) a mono- or di-$C_{1-6}$ alkylamino group (preferably, a mono- or di-$C_{1-3}$ alkylamino group).

The aforementioned "$C_{3-10}$ cycloalkyl group", "$C_{3-6}$ cycloalkenyl group", "cyclic amino group", "aromatic group", "dihydroindenyl group" and "nonaromatic heterocyclic group" are optionally substituted by 1 to 3 substituents selected from, for example, the following substituent group B.

[Substituent Group B]
(a) a halogen atom,
(b) a cyano group,
(c) a hydroxyl group,
(d) a nitro group,
(e) a formyl group,
(f) a $C_{1-6}$ alkoxy group (preferably, a $C_{1-3}$ alkoxy group),
(g) a $C_{3-6}$ cycloalkyl group optionally substituted by 1 to 3 hydroxyl groups,
(h) a $C_{6-14}$ aryl group, (i) a cyclic amino group (e.g., a piperidino group, a morpholino group),
(j) a heterocyclic group (e.g., a furyl group, a tetrahydrofuranyl group),
(k) a $C_{1-6}$ alkyl-carbonyl group,
(l) an amino group,
(m) a mono- or di-$C_{1-6}$ alkylamino group (preferably, a mono- or di-$C_{1-3}$ alkylamino group), and
(n) a $C_{1-6}$ alkyl group (preferably, a $C_{1-3}$ alkyl group) optionally substituted by 1 to 3 substituents selected from a halogen atom and a hydroxyl group.

Examples of the same or different preferable $R^4$ and $R^5$ include
a hydrogen atom,
a $C_{1-6}$ alkyl group,
a $C_{2-10}$ alkyl group optionally substituted by a hydroxyl group optionally substituted by a $C_{1-3}$ alkyl group or an amino group optionally substituted by a $C_{1-3}$ alkyl group,
a $C_{3-10}$ cycloalkyl group, and
an aromatic group (e.g., a phenyl group, a pyridyl group) optionally substituted by substituent(s) selected from a halogen atom, a $C_{1-6}$ alkyl group, a $C_{1-3}$ alkoxy group, a hydroxyl group and an amino group.

In a more preferable combination of $R^4$ and $R^5$, $R^4$ is a hydrogen atom, and $R^5$ is a 2-hydroxyethyl group, a 2-methoxyethyl group, a 2-hydroxycyclohexyl group, a 2-hydroxycyclopentyl group, a 2-(hydroxymethyl)cyclohexyl group or a 3-hydroxytetrahydropyran-4-yl group.

When $R^4$ is a hydrogen atom, and $R^5$ is a 2-hydroxycyclohexyl group, a 2-hydroxycyclopentyl group, a 2-(hydroxymethyl)cyclohexyl group or a 3-hydroxytetrahydropyran-4-yl group, the relative configuration of the binding of the nitrogen atom of the amino group and the carbon atom on the ring, and the binding of the hydroxyl group or the hydroxymethyl group and the carbon atom on the ring is preferably trans.

Particularly, an embodiment wherein $R^1$ has an absolute configuration shown by the following formula is preferable.

In addition, one of $R^4$ and $R^5$ is preferably a hydrogen atom,

Examples of the substituent that the "cyclic amino group" of the "optionally substituted cyclic amino group" for $R^1$ optionally has include substituents selected from
(1) a halogen atom,
(2) a hydroxyl group,
(3) an optionally substituted $C_{1-6}$ alkyl group,
(4) an optionally substituted $C_{2-6}$ alkenyl group,
(5) an optionally substituted $C_{1-6}$ alkoxy group,
(6) an optionally substituted $C_{3-6}$ cycloalkyl group,
(7) an optionally substituted $C_{3-6}$ cycloalkenyl group,
(8) an optionally substituted $C_{6-14}$ aryl group,
(9) an optionally substituted heterocyclic group,
(10) a $C_{1-6}$ alkyl-carbonyl group,
(11) a $C_{1-6}$ alkoxy-carbonyl group
and the like. The number of the substituents is 1 to 4, preferably 1 to 3.

The aforementioned "$C_{1-6}$ alkyl group", "$C_{2-6}$ alkenyl group" and "$C_{1-6}$ alkoxy group" are optionally substituted by 1 to 3 substituents selected from the aforementioned substituent group A.

The aforementioned "$C_{3-6}$ cycloalkyl group", "$C_{3-6}$ cycloalkenyl group", "$C_{6-14}$ aryl group" and "heterocyclic group" are optionally substituted by 1 to 3 substituents selected from the aforementioned substituent group B.

$R^1$ is preferably
(a) an amino group optionally substituted by 1 or 2 substituents selected from
(1) an amino group,
(2) a $C_{1-6}$ alkyl group optionally substituted by 1 to 3 substituents selected from (i) a hydroxyl group, (ii) a $C_{1-3}$ alkoxy group, (iii) a $C_{3-6}$ cycloalkyl group substituted by 1 to 3 hydroxyl groups, (iv) a phenyl group, (v) a furyl group, (vi) a tetrahydrofuranyl group, (vii) a piperidino group and (viii) a morpholino group,
(3) a $C_{3-6}$ cycloalkyl group optionally substituted by 1 to 3 substituents selected from a halogen atom, a hydroxyl group and a hydroxymethyl group,
(4) a 4- to 10-membered cyclic amino group (e.g., piperidino),
(5) a phenyl group optionally substituted by 1 to 3 substituents selected from a halogen atom, a $C_{1-6}$ alkyl group optionally substituted by 1 to 3 halogen atoms and a hydroxymethyl group,
(6) a dihydroindenyl group substituted by 1 to 3 hydroxyl groups,
(7) a pyrazolyl group,
(8) a tetrahydrofuranyl group, and
(9) a tetrahydropyranyl group substituted by 1 to 3 hydroxyl groups, or
(b) a 4- to 10-membered cyclic amino group (e.g., azetidin-1-yl, pyrrolidin-1-yl, piperidino, 1,3-dihydro-2H-isoindol-2-yl) optionally substituted by 1 to 3 substituents selected from a hydroxyl group and a hydroxymethyl group.

Another preferable embodiment of $R^1$ is
(a) an amino group optionally substituted by 1 or 2 substituents selected from
(1) an amino group,
(2) a $C_{1-6}$ alkyl group optionally substituted by 1 or 2 substituents selected from a hydroxyl group, a $C_{1-3}$ alkoxy group, a $C_{3-6}$ cycloalkyl group, a phenyl group, a furyl group, a tetrahydrofuranyl group and a morpholino group,
(3) a $C_{3-6}$ cycloalkyl group optionally substituted by a hydroxyl group or a hydroxymethyl group,
(4) a 4- to 7-membered cyclic amino group (e.g., piperidino),
(5) a phenyl group optionally substituted by substituent(s) selected from a halogen atom, a $C_{1-6}$ alkyl group and a hydroxymethyl group,
(6) a dihydroindenyl group substituted by a hydroxyl group,
(7) a pyrazolyl group,
(8) a tetrahydrofuranyl group, and
(9) a tetrahydropyranyl group substituted by a hydroxyl group, or
(b) a 4- to 7-membered cyclic amino group (e.g., azetidin-1-yl, pyrrolidin-1-yl, piperidino) optionally substituted by substituent(s) selected from a hydroxyl group and a hydroxymethyl group.

$R^2$ and $R^3$ are each independently a hydrogen atom or a substituent.

Examples of the substituent for $R^2$ or $R^3$ include
(1) a halogen atom,
(2) a cyano group,
(3) a nitro group,
(4) a hydroxyl group,
(5) a $C_{1-6}$ alkyl group (preferably, a $C_{1-3}$ alkyl group) optionally substituted by 1 to 3 halogen atoms,
(6) a $C_{1-6}$ alkoxy group (preferably, a $C_{1-3}$ alkoxy group) optionally substituted by 1 to 3 halogen atoms,
(7) a carboxy group,
(8) a $C_{1-6}$ alkyl-carbonyl group,
(9) a $C_{1-6}$ alkoxy-carbonyl group,
(10) a carbamoyl group,
(11) a mono- or di-$C_{1-6}$ alkylcarbamoyl group,
(12) an amino group,
(13) a mono- or di-$C_{1-6}$ alkylamino group and the like.

$R^2$ and $R^3$ are preferably the same and are hydrogen atoms or halogen atoms, more preferably the same and are hydrogen atoms or fluorine atoms.

Alternatively, an embodiment wherein $R^2$ is a hydrogen atom, and $R^3$ is a halogen atom or a $C_{1-3}$ alkoxy group substituted by 1 to 3 halogen atoms, is also preferable.

Ring A is an optionally substituted 5- to 10-membered ring. However, ring A is not an unsubstituted phenyl group; and when both $R^2$ and $R^3$ are hydrogen atoms, ring A is not an unsubstituted $C_{3-6}$ cycloalkyl group, or a phenyl group having a halogen atom or a methyl group at the 4-position.

Examples of the "5- to 10-membered ring" of the "optionally substituted 5- to 10-membered ring" for ring A include a 5- to 10-membered saturated ring, an aromatic ring and a fused ring. The aforementioned saturated ring, aromatic ring and fused ring optionally contain 1 to 4 (preferably 1 to 3, more preferably 1 or 2) hetero atoms selected from a nitrogen atom, a sulfur atom and an oxygen atom.

In ring A,
a preferable structure of the saturated ring is azetidinyl, pyrrolidinyl, piperidinyl, azepanyl, 1,4-diazepanyl, cycloheptyl, cyclopropyl, cyclobutyl, cyclopentyl or cyclohexyl (excluding unsubstituted cyclohexyl), each of which is optionally substituted, and
a preferable structure of the aromatic ring is a 6-membered ring such as pyridyl, pyrimidinyl, pyridazinyl, pyrazinyl, triazinyl and phenyl (excluding unsubstituted phenyl and phenyl substituted by a halogen atom at the 4-position), each of which is optionally substituted, and
a preferable structure of the fused ring is naphthyl, quinolyl, isoquinolyl, cinnolinyl, quinolizinyl, quinoxalinyl, quinazolinyl, phthalazinyl, naphthyridinyl, benzopyranyl, benzofuranyl, indenyl, benzothienyl, indolyl, benzimidazolyl, benzotriazolyl, imidazopyridyl, benzoxazinyl or decalinyl, each of which is optionally substituted.

Examples of the substituent that the "5- to 10-membered ring" of the "optionally substituted 5- to 10-membered ring" for ring A optionally has include
(1) a halogen atom,
(2) a cyano group,
(3) a nitro group,
(4) a hydroxyl group,
(5) a $C_{1-6}$ alkyl group (preferably, a $C_{1-3}$ alkyl group) optionally substituted by 1 to 3 halogen atoms,
(6) a $C_{1-6}$ alkoxy group (preferably, a $C_{1-3}$ alkoxy group) optionally substituted by 1 to 3 halogen atoms,
(7) a carboxy group,
(8) a $C_{1-6}$ alkyl-carbonyl group,
(9) a $C_{1-6}$ alkoxy-carbonyl group,
(10) a carbamoyl group,
(11) a mono- or di-$C_{1-6}$ alkylcarbamoyl group,
(12) an amino group,
(13) a mono- or di-$C_{1-6}$ alkylamino group,
(14) a heterocyclic group (e.g., a 5- to 10-membered aromatic heterocyclic group containing 1 to 4 (preferably 1 to 3, more preferably 1 or 2) hetero atoms selected from a nitrogen atom, a sulfur atom and an oxygen atom such as a pyrazolyl group, a pyridyl group and the like) optionally substituted by 1 to 3 $C_{1-6}$ alkyl groups,
and the like. The number of the substituents is 1 to 4, preferably 1 to 3, more preferably 1 or 2, particularly preferably 1.

Ring A is preferably a phenyl group wherein the 4-position is substituted by a substituent selected from (i) a $C_{1-3}$ alkyl group substituted by 1 to 3 halogen atoms, (ii) a $C_{1-3}$ alkoxy group, (iii) a carbamoyl group, (iv) a pyrazolyl group optionally substituted by 1 to 3 $C_{1-6}$ alkyl groups and (v) a pyridyl group substituted by 1 to 3 $C_{1-6}$ alkyl groups.

Ring A is more preferably a phenyl group wherein the 4-position is substituted by a substituent selected from
(i) a $C_{1-3}$ alkyl group substituted by 1 to 3 halogen atoms, (ii) a $C_{1-3}$ alkoxy group, (iii) a carbamoyl group and (iv) a pyrazolyl group.

Ring A is further preferably a phenyl group wherein the 4-position is substituted by a substituent selected from a $C_{1-3}$ alkoxy group, a carbamoyl group and a pyrazolyl group.

Preferred as compound (I) are the following compounds.
[Compound (I)-A]
A compound of the formula (I) wherein
$R^1$ is
(a) an amino group optionally substituted by 1 or 2 substituents selected from
(1) an amino group,
(2) a $C_{1-6}$ alkyl group optionally substituted by 1 or 2 substituents selected from
(i) a hydroxyl group, (ii) a $C_{1-3}$ alkoxy group, (iii) a $C_{3-6}$ cycloalkyl group optionally substituted by 1 to 3 hydroxyl groups, (iv) a phenyl group, (v) a furyl group, (vi) a tetrahydrofuranyl group, (vii) a piperidino group and (viii) a morpholino group,
(3) a $C_{3-6}$ cycloalkyl group optionally substituted by 1 to 3 substituents selected from a halogen atom, a hydroxyl group and a hydroxymethyl group,
(4) a 4- to 10-membered cyclic amino group (e.g., piperidino),
(5) a phenyl group optionally substituted by substituent(s) selected from a halogen atom, a $C_{1-6}$ alkyl group and a hydroxymethyl group,
(6) a dihydroindenyl group substituted by a hydroxyl group,
(7) a pyrazolyl group,
(8) a tetrahydrofuranyl group, and
(9) a tetrahydropyranyl group substituted by a hydroxyl group, or
(b) a 4- to 10-membered cyclic amino group (e.g., azetidin-1-yl, pyrrolidin-1-yl, piperidino, 1,3-dihydro-2H-isoindol-2-yl) optionally substituted by a substituent selected from a hydroxyl group and a hydroxymethyl group,
$R^2$ and $R^3$ are the same and each is a hydrogen atom or a halogen atom, or
$R^2$ is a hydrogen atom, and $R^3$ is a halogen atom, or a $C_{1-3}$ alkoxy group substituted by 1 to 3 halogen atoms,
X is —CH= or —N=, and
ring A is a phenyl group wherein the 4-position is substituted by a substituent selected from
(i) a $C_{1-3}$ alkyl group substituted by 1 to 3 halogen atoms, (ii) a $C_{1-3}$ alkoxy group, (iii) a carbamoyl group and (iv) a pyrazolyl group,
or a salt thereof.

[Compound (I)-B]

A compound of the formula (I) wherein
$R^1$ is
(a) an amino group optionally substituted by 1 or 2 substituents selected from
(1) an amino group,
(2) a $C_{1-6}$ alkyl group optionally substituted by 1 or 2 substituents selected from a hydroxyl group, a $C_{1-3}$ alkoxy group, a $C_{3-6}$ cycloalkyl group, a phenyl group, a furyl group, a tetrahydrofuranyl group and a morpholino group,
(3) a $C_{3-6}$ cycloalkyl group optionally substituted by a halogen atom or a hydroxymethyl group,
(4) a 4- to 7-membered cyclic amino group (e.g., piperidino),
(5) a phenyl group optionally substituted by substituent(s) selected from a halogen atom, a $C_{1-6}$ alkyl group and a hydroxymethyl group,
(6) a dihydroindenyl group substituted by a hydroxyl group,
(7) a pyrazolyl group,
(8) a tetrahydrofuranyl group, and
(9) a tetrahydropyranyl group substituted by a hydroxyl group, or
(b) a 4- to 7-membered cyclic amino group (e.g., azetidin-1-yl, pyrrolidin-1-yl, piperidino) optionally substituted by a substituent selected from a hydroxyl group and a hydroxymethyl group,
$R^2$ and $R^3$ are the same and each is a hydrogen atom or a halogen atom,
X is —CH= or —N=, and
ring A is a phenyl group wherein the 4-position is substituted by a substituent selected from a $C_{1-3}$ alkoxy group, a carbamoyl group and a pyrazolyl group,
or a salt thereof.

When compound (I) is in a form of a salt, examples of such salt include salts with inorganic base, an ammonium salt, salts with organic base, salts with inorganic acid, salts with organic acid, salts with basic or acidic amino acid, and the like.

Preferable examples of the salt with inorganic base include alkali metal salts such as sodium salt, potassium salt and the like; alkaline earth metal salts such as calcium salt, magnesium salt, barium salt and the like; an aluminum salt, and the like.

Preferable examples of the salt with organic base include salts with trimethylamine, triethylamine, pyridine, picoline, ethanolamine, diethanolamine, triethanolamine, dicyclohexylamine, N,N'-dibenzylethylenediamine and the like.

Preferable examples of the salt with inorganic acid include salts with hydrochloric acid, hydrobromic acid, nitric acid, sulfuric acid, phosphoric acid and the like.

Preferable examples of the salt with organic acid include salts with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include salts with arginine, lysine, ornithine and the like.

Preferable examples of the salt with acidic amino acid include salts with aspartic acid, glutamic acid and the like.

Among these salts, a pharmaceutically acceptable salt is preferable. When a compound has a basic functional group, examples of a preferable pharmaceutically acceptable salt include salts with inorganic acid such as hydrochloric acid, hydrobromic acid, nitric acid, sulfuric acid, phosphoric acid and the like, and salts with organic acid such as acetic acid, phthalic acid, fumaric acid, oxalic acid, tartaric acid, maleic acid, citric acid, succinic acid, methanesulfonic acid, p-toluenesulfonic acid and the like. In addition, when a compound has an acidic functional group, examples thereof include inorganic salts such as alkali metal salts (e.g., sodium salt, potassium salt etc.), alkaline earth metal salts (e.g., calcium salt, magnesium salt, barium salt etc.) and the like, ammonium salt and the like.

Compound (I) may be a crystal, and both a single crystal and crystal mixtures are encompassed in the compound (I).

Compound (I) may be a pharmaceutically acceptable cocrystal or cocrystal salt. Here, the cocrystal or cocrystal salt means a crystalline substance consisting of two or more particular substances which are solids at room temperature, each having different physical properties (e.g., structure, melting point, heat of melting, hygroscopicity, solubility, stability etc.). The cocrystal and cocrystal salt can be produced by cocrystallization method known per se.

Compound (I) encompasses solvates (e.g., hydrate) and non-solvates within the scope thereof. Compound (I) may be a compound labeled or substituted with an isotope (e.g., $^2H$, $^3H$, $^{11}C$, $^{14}C$, $^{18}F$, $^{35}S$, $^{125}I$). A compound labeled with or substituted by an isotope can be used, for example, as a tracer used for Positron Emission Tomography (PET) (PET tracer), and is useful in the field of medical diagnosis and the like.

When compound (I) of the present invention has an asymmetric center, isomers such as enantiomer, diastereomer and the like may be present. Such isomers and a mixture thereof are all encompassed within the scope of the present invention. When an isomer is formed due to the conformation or tautomerism, such isomers and a mixture thereof are all encompassed in compound (I) of the present invention.

The production methods of the compound of the present invention are explained below.

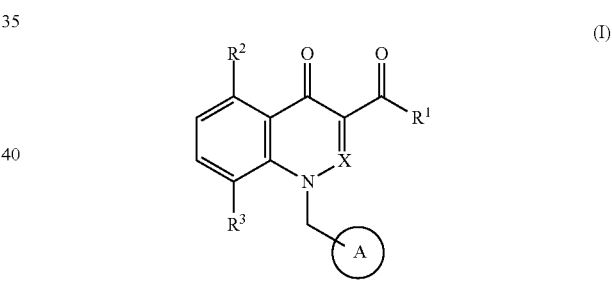

wherein $R^1$, $R^2$, $R^3$, X and ring A are as defined above.

A compound represented by the above-mentioned of the formula (I) can be produced by, for example, the methods shown below or a method analogous thereto and the like. In the following synthesis methods, the starting compound may be used as a salt, and as such salt, those exemplified as the salt of compound (I) can be used.

While the yield of the compound represented by the above-mentioned formula (I), which is obtained by the following method, can vary depending on the reaction conditions used, compound (I) can be easily obtained at high purity from the resultant products by general separation and purification means (recrystallization, column chromatography and the like).

Examples of the inert solvent to be used for the production method of the compound of the present invention include the following solvents.
ether solvents: diethyl ether, diisopropyl ether, diphenyl ether, tetrahydrofuran, 1,4-dioxane, 1,2-dimethoxyethane etc.

aromatic hydrocarbon solvents: benzene, toluene, xylene, trifluoromethylbenzene etc.
aliphatic hydrocarbon solvents: cyclohexane, hexane etc.
amide solvents: N,N-dimethylformamide, N,N-dimethylacetamide, hexamethylphosphoric triamide etc.
halogenated hydrocarbon solvents: dichloromethane, chloroform, carbon tetrachloride, 1,2-dichloroethane etc.
nitrile solvents: acetonitrile, propionitrile etc.
sulfoxide solvents: dimethyl sulfoxide etc.
ketone solvents: acetone, methyl ethyl ketone etc.

Examples of the base to be used for the production method of the compound of the present invention include the following bases.
inorganic bases: sodium hydroxide, potassium hydroxide, magnesium hydroxide etc.
basic salts: sodium carbonate, potassium carbonate, cesium carbonate, calcium carbonate, sodium hydrogen carbonate etc.
metal alkoxides: sodium methoxide, sodium ethoxide, potassium tert-butoxide etc.
alkali metal hydrides: sodium hydride, potassium hydride etc.
metal amides: sodium amide, lithium diisopropylamide, lithium hexamethyldisilazide etc.
aromatic amines: pyridine, lutidine etc.
tertiary amines: triethylamine, diisopropylethylamine, tributylamine, cyclohexyldimethylamine, 4-dimethylaminopyridine, N,N-dimethylaniline, N-methylpiperidine, N-methylpyrrolidine, N-methylmorpholine etc.

Production Method 1

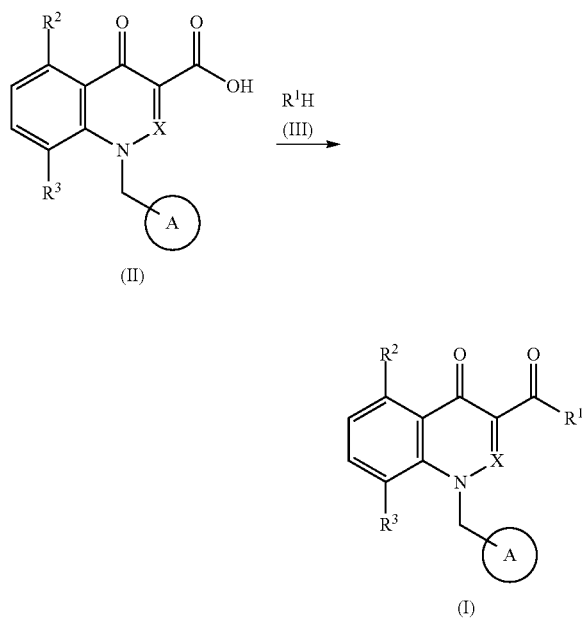

wherein $R^1$, $R^2$, $R^3$, X and ring A are as defined above.

Compound (I) can be produced by an amidation reaction of compound (II). Compounds (II) and (III) may be commercially available reagents or can be prepared by referring to the method shown in Reference Example or a method analogous thereto, or a known method (Journal of Heterocyclic Chemistry, 1998, 35, 955 or Chemical and Pharmaceutical Bulletin, 1988, 36, 1321).

The above-mentioned "amidation reaction" includes the following "method using a dehydrating condensing agent", the "method using a reactive derivative of a carboxylic acid" and the like.

i) Method Using a Dehydrating Condensing Agent

The method is performed by reacting compound (II) with compound (III) in the presence of a dehydrating condensing agent, in an inert solvent. Where necessary, the reaction can be performed in the presence of 1-hydroxybenzotriazole (HOBt) in a catalytic amount to 5 molar equivalents relative to compound (II), a base in a catalytic amount to 5 molar equivalents relative to compound (II), and the like.

As compound (III), a commercially available compound can be obtained easily, or can also be produced according to a method known per se or a method analogous thereto.

The amount of compound (III) to be used is generally 0.5 to 5 molar equivalents, preferably 0.8 to 1.5 molar equivalents, relative to compound (II).

Examples of the above-mentioned "dehydrating condensing agent" include dicyclohexylcarbodiimide (DCC), 1-ethyl-3-(3-dimethylaminopropyl)carbodiimide hydrochloride (EDC-HCl or WSC), O-(7-azabenzotriazol-1-yl)-N,N,N',N'-tetramethyluronium hexafluorophosphate (HATU) and the like. The amount of the "dehydrating condensing agent" to be used is generally 1 to 10 molar equivalents, preferably 1 to 5 molar equivalents, relative to compound (II).

Examples of the above-mentioned "inert solvent" include nitrile solvents, amide solvents, halogenated hydrocarbon solvents, ether solvents and the like. These solvents may be used in a mixture of two or more kinds thereof in an appropriate ratio. Among them, amide solvents are preferable.

Examples of the above-mentioned "base" include "aromatic amines", "tertiary amines" and the like. Among them, triethylamine and diisopropylethylamine are preferable.

The reaction temperature is generally −70° C. to 150° C., preferably −20° C. to 100° C.

The reaction time is generally 0.1 hr to 100 hr, preferably 1 hr to 48 hr.

ii) Method Using a Reactive Derivative of a Carboxylic Acid

A reactive derivative of compound (II) is reacted with compound (III) in 0.5 to 5 molar equivalents (preferably 0.8 to 3 molar equivalents) relative to compound (II) in an inert solvent. Where necessary, the reaction may be performed in the presence of a base in 1 to 10 molar equivalents, preferably 1 to 3 molar equivalents, relative to compound (II).

Examples of the "reactive derivative" of compound (II) include acid halides (e.g., acid chlorides, acid bromides), mixed acid anhydrides (e.g., acid anhydrides with a $C_{1-6}$ alkyl-carboxylic acid, a $C_{6-10}$ aryl-carboxylic acid, a $C_{1-6}$ alkyl carbonate etc.), active esters (e.g., esters with a phenol optionally having substituent(s), HOBt, N-hydroxysuccinimide etc.), and the like.

Examples of the "substituent" of the above-mentioned "phenol optionally having substituent(s)" include 1 to 5 substituents selected from the aforementioned substituent group B.

Specific examples of the "phenol optionally having substituent(s)" include phenol, pentachlorophenol, pentafluorophenol, p-nitrophenol and the like.

The reactive derivative is preferably an acid halide.

Examples of the above-mentioned "inert solvent" include ether solvents, halogenated hydrocarbon solvents, aromatic hydrocarbon solvents, aliphatic hydrocarbon solvents, nitrile solvents, amide solvents, ketone solvents, sulfoxide solvents, water and the like. These solvents may be used in a mixture of two or more kinds thereof in an appropriate ratio. Among these, acetonitrile, tetrahydrofuran (THF), dichloromethane, chloroform and the like are preferable.

Examples of the above-mentioned "base" include "aromatic amines", "tertiary amines" and the like. Among these, triethylamine and diisopropylethylamine are preferable.

The reaction temperature is generally −20° C. to 100° C., preferably −20° C. to 50° C.

The reaction time is generally 5 min to 40 hr, preferably 30 min to 18 hr.

Production Method 2

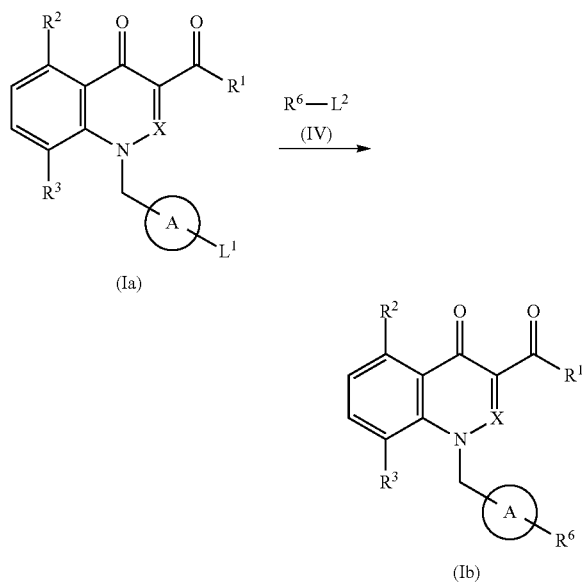

wherein $L^1$ and $L^2$ are each a leaving group, $R^6$ is a substituent on ring A, and $R^1$, $R^2$, $R^3$, X and ring A are as defined above.

The above-mentioned formulas show a method of producing the object compound (Ib) by introducing substituent $R^6$ on ring A of compound (Ia) by using (IV).

Examples of the leaving groups $L^1$ and $L^2$ include alkali metal (e.g., lithium, sodium etc.), a halogen atom (e.g., fluorine, chlorine, bromine, iodine etc.), a $C_{1-6}$ alkoxy group (e.g., methoxy group etc.), a $C_{6-14}$ aryloxy group (e.g., phenoxy group etc.), an optionally substituted acyloxy group (e.g., acetyloxy group, benzoyloxy group etc.), an optionally halogenated $C_{1-6}$ alkylsulfonyloxy group [e.g., methanesulfonyloxy group, ethanesulfonyloxy group, trichloromethanesulfonyloxy group, trifluoromethanesulfonyloxy (triflate) group etc.], an optionally substituted $C_{6-14}$ arylsulfonyloxy group [for example, $C_{6-14}$ arylsulfonyloxy group optionally having 1 to 3 substituents selected from $C_{1-6}$ alkyl group (e.g., methyl group, ethyl group, propyl group, isopropyl group, butyl group, isobutyl group, sec-butyl group, tert-butyl group, pentyl group, hexyl group etc.), $C_{1-6}$ alkoxy group (e.g., methoxy group, ethoxy group, propoxy group, isopropoxy group, butoxy group, isobutoxy group, sec-butoxy group, pentyloxy group, hexyloxy group etc.) and a nitro group, and the like can be mentioned, and specific examples include benzenesulfonyloxy group, m-nitrobenzenesulfonyloxy group, p-toluenesulfonyloxy group, naphthylsulfonyloxy group etc.], a $C_{1-6}$ alkyloxonio group (e.g., dimethyloxonio group, diethyloxonio group etc.), a diazo group, a diazonio group, an optionally substituted $C_{6-14}$ aryliodonio group (e.g., phenyliodonio group), a boron functional group (e.g.,

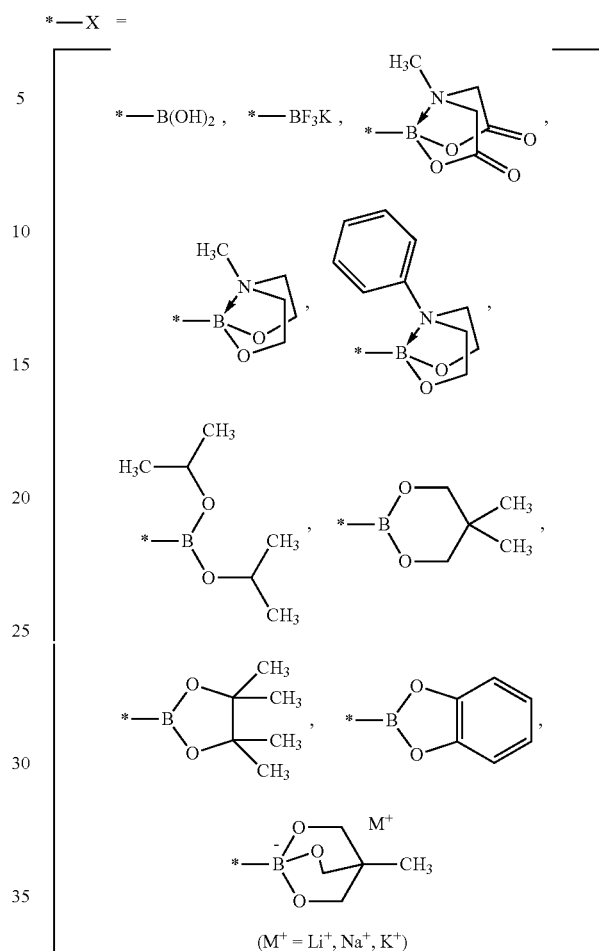

etc.), an optionally substituted $C_{1-6}$ alkylsilyl group (e.g., trimethylsilyl group etc.), an optionally substituted $C_{1-6}$ alkylstannyl group (e.g., tributylstannyl group etc.), an optionally substituted $C_{2-6}$ alkenylstannyl group, an optionally substituted $C_{6-14}$ arylstannyl group, a metal-containing substituent such as magnesium halide, zinc halide and the like, and the like.

Also, $L^1$ and $L^2$ include substituents convertible to a leaving group, and they can be converted in a desired step to a leaving group by a reaction known per se. For example, when $L^1$ and $L^2$ are methylthio groups, they can be converted to a methanesulfonyl group by an oxidation reaction, and the like.

The starting compounds (Ia) and (IV) shown by the above-mentioned reaction may be commercially available reagents or can be produced by a method known per se, the method shown in Reference Example or a method analogous thereto.

This reaction is performed in the presence of a base, an additive and a metal catalyst as necessary, in a solvent that does not adversely influence the reaction. The amount of compound (IV) to be used is generally about 1 to about 10 molar equivalents, preferably about 1 to about 5 molar equivalents, relative to compound (Ia).

Examples of such "base" include alkali metal salts such as potassium hydroxide, sodium hydroxide, sodium hydrogen carbonate, potassium carbonate and the like; amines such as pyridine, triethylamine, N,N-dimethylaniline, 1,8-diazabicyclo[5.4.0]undec-7-ene and the like; metal hydrides such as potassium hydride, sodium hydride and the like; alkali metal alkoxides such as sodium methoxide, sodium ethoxide, potassium tert-butoxide and the like.

The amount of the base to be used is preferably about 1 to about 5 molar equivalents relative to compound (Ia).

Examples of such "additive" include inorganic salts such as sodium iodide, potassium iodide and the like, ammonium salts such as tetrabutylammonium iodide and the like, molecular sieves such as molecular sieve 3A, molecular sieve 4A and the like.

The amount in weight ratio of the "additive" to be used is about 0.1 to 500-fold, preferably 0.1 to 30-fold, relative to compound (Ia).

Examples of such "metal catalyst" include metals such as nickel, palladium, copper and the like, metal salt, metal complex consisting of these and ligand, and the like. Examples of these reagents include tetrakis(triphenylphosphine)palladium(0), bis(triphenylphosphine)palladium(II) dichloride, [1,1'-bis(diphenylphosphino)ferrocene]palladium(II) dichloride, [1,1'-bis(diphenylphosphino)ferrocene]palladium(II) dichloride-dichloromethane adduct, tris(dibenzylideneacetone)dipalladium(0), bis(di-tert-butyl(4-dimethylaminophenyl)phosphine)dichloropalladium(II), chloro(2-dicyclohexylphosphino-2',4',6'-triisopropyl-1,1'-biphenyl) [2-(2-aminoethyl)phenyl)]palladium(II), chloro-(2-dicyclohexylphosphino-2',6'-diisopropoxy-1,1'-biphenyl) [2-(2-aminoethyl)phenyl]palladium(II)-methyl-tert-butyl ether adduct, chloro[2-(dicyclohexylphosphino)-3,6-dimethoxy-2',4',6'-triisopropyl-1,1'-biphenyl][2-(2-aminoethyl)phenyl]palladium(II)-methyl-tert-butyl ether adduct, chloro[2-(di-tert-butylphosphino)-2',4',6'-triisopropyl-1,1'-biphenyl][2-(2-aminoethyl)phenyl)]palladium(II), trans-dichlorobis(tri-o-tolylphosphine)palladium(II), palladium(II) trifluoroacetate, palladium(II) acetate, nickel(II) acetylacetonate, 1,2-bis(diphenylphosphino)ethane nickel chloride complex, copper iodide, copper bromide, copper chloride, copper acetate, copper oxide and the like. Furthermore, a ligand may be added to the reaction system. Examples of the ligand include phosphine ligand [e.g., triphenylphosphine, 2,2'-bis(diphenylphosphino)-1,1'-binaphthyl, 2-dicyclohexylphosphino-2',6'-diisopropoxy-1,1'-biphenyl, 2-(dicyclohexylphosphino)-3,6-dimethoxy-2',4',6'-triisopropyl-1,1'-biphenyl, 2-di-tert-butylphosphino-3,4,5,6-tetramethyl-2',4',6'-triisopropyl-1,1'-biphenyl, 2-(di-tert-butylphosphino)biphenyl, 2-(dicyclohexylphosphino)biphenyl, 2-dicyclohexylphosphino-2',6'-dimethoxy-1,1'-biphenyl, 2-dicyclohexylphosphino-2',4',6'-triisopropyl-1,1'-biphenyl, 2-(dicyclohexylphosphino)-2'-(N,N-dimethylamino)biphenyl, 1,1'-bis(diphenylphosphino)ferrocene, tri-tert-butylphosphine, tricyclohexylphosphine, 4,5-bis(diphenylphosphino)-9,9-dimethylxanthene etc.], amine ligand (N,N'-dimethylethylenediamine, trans-1,2-diaminocyclohexane, trans-N,N'-dimethyl-1,2-cyclohexanediamine, 1,10-phenanthroline, 4,7-dimethoxy-1,10-phenanthroline, 3,4,7,8-tetramethyl-1,10-phenanthroline etc.), diketone ligand (2-acetylcyclohexanone, 2-isobutyrylhexanone, 2,2,6,6-tetramethyl-3,5-heptanedione etc.), salicylaldoxime, proline and the like.

The amount of the "metal catalyst" to be used is generally about 0.0001 to 1000 wt %, preferably about 0.01 to 200 wt %, relative to compound (Ia).

The amount of the "ligand" to be used is generally about 0.0001 to about 1000 wt %, preferably about 0.01 to about 200 wt %, relative to compound (Ia).

This reaction is advantageously performed without solvent or in a solvent inert to the reaction. The solvent is not particularly limited as long as the reaction proceeds, and, for example, solvents such as alcohols such as methanol, ethanol, 1-propanol, 2-propanol, 1-butanol, 2-methyl-2-propanol, 2-methyl-2-butanol and the like, ethers such as diethyl ether, diisopropyl ether, cyclopentyl methyl ether, tetrahydrofuran, 2-methyltetrahydrofuran, 1,4-dioxane, 1,2-dimethoxyethane and the like, hydrocarbons such as cyclohexane, hexane and the like, aromatic hydrocarbons such as benzene, chlorobenzene, toluene, xylene, (trifluoromethyl)benzene and the like, amides such as N,N-dimethylformamide, N,N-dimethylacetamide, 1-methyl-2-pyrrolidone and the like, halogenated hydrocarbons such as dichloromethane, chloroform, carbon tetrachloride, 1,2-dichloroethane and the like, nitriles such as acetonitrile, propionitrile and the like, sulfoxides such as dimethyl sulfoxide and the like, nitrogen-containing aromatic hydrocarbons such as pyridine, lutidine, quinoline and the like, water and the like or a mixed solvent thereof and the like are preferable.

The reaction temperature is generally about −50° C. to about 150° C., preferably about −10° C. to about 100° C.

The reaction time is generally about 0.5 to about 20 hr.

In the aforementioned reaction, when the starting compound has a hydroxy group, an amino group, a carboxy group or a carbonyl group as a substituent, a protecting group generally used in the peptide chemistry and the like may be introduced into these groups, and the object compound can be obtained by removing the protecting group as necessary after the reaction.

Examples of the hydroxy-protecting group include a $C_{1-6}$ alkyl group (e.g., methyl, ethyl, propyl, isopropyl, butyl, tert-butyl), a phenyl group, a trityl group, a $C_{7-10}$ aralkyl group (e.g., benzyl), a formyl group, a $C_{1-6}$ alkyl-carbonyl group (e.g., acetyl, propionyl), a benzoyl group, a $C_{7-10}$ aralkyl-carbonyl group (e.g., benzylcarbonyl), a 2-tetrahydropyranyl group, a 2-tetrahydrofuranyl group, a silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom (e.g., fluorine, chlorine, bromine, iodine), a $C_{1-6}$ alkyl group (e.g., methyl, ethyl, propyl), a $C_{1-6}$ alkoxy group (e.g., methoxy, ethoxy, propoxy), a nitro group and the like.

Examples of the amino-protecting group include a formyl group, a $C_{1-6}$ alkyl-carbonyl group (e.g., acetyl, propionyl), a $C_{1-6}$ alkoxy-carbonyl group (e.g., methoxycarbonyl, ethoxycarbonyl, tert-butoxycarbonyl), a benzoyl group, a $C_{7-10}$ aralkyl-carbonyl group (e.g., benzylcarbonyl), a $C_{7-14}$ aralkyloxy-carbonyl group (e.g., benzyloxycarbonyl, 9-fluorenylmethoxycarbonyl), a trityl group, a phthaloyl group, a N,N-dimethylaminomethylene group, a silyl group (e.g., trimethylsilyl, triethylsilyl, dimethylphenylsilyl, tert-butyldimethylsilyl, tert-butyldiethylsilyl), a $C_{2-6}$ alkenyl group (e.g., 1-allyl) and the like. These groups are optionally substituted by 1 to 3 substituents selected from a halogen atom (e.g., fluorine, chlorine, bromine, iodine), a $C_{1-6}$ alkoxy group (e.g., methoxy, ethoxy, propoxy), a nitro group and the like.

Examples of the carboxy-protecting group include a $C_{1-6}$ alkyl group (e.g., methyl, ethyl, propyl, isopropyl, butyl, tert-butyl), a $C_{7-11}$ aralkyl group (e.g., benzyl), a phenyl group, a trityl group, a silyl group (e.g., trimethylsilyl, triethylsilyl, dimethylphenylsilyl, tert-butyldimethylsilyl, tert-butyldiethylsilyl, tert-butyldiphenylsilyl), a $C_{2-6}$ alkenyl group (e.g., 1-allyl) and the like. These groups are optionally substituted by 1 to 3 substituents selected from a halogen atom (e.g., fluorine, chlorine, bromine, iodine), a $C_{1-6}$ alkoxy group (e.g., methoxy, ethoxy, propoxy), nitro group and the like.

Examples of the carbonyl-protecting group include a cyclic acetal (e.g., 1,3-dioxane), a non-cyclic acetal (e.g., a di-$C_{1-6}$ alkyl acetal) and the like.

These protecting groups can be removed by a method known per se, for example, the method described in Protective Groups in Organic Synthesis, John Wiley and Sons (1980) and the like. For example, a method using acid, base, ultraviolet rays, hydrazine, phenylhydrazine, sodium N-methyldithiocarbamate, tetrabutylammonium fluoride, palladium acetate, trialkylsilyl halide (e.g., trimethylsilyl iodide, trimethylsilyl bromide) and the like, a reduction method and the like can be mentioned.

When compound (I) has an optical isomer, a stereoisomer, a regioisomer or a rotamer, these are also encompassed in compound (I), and can be obtained as a single product according to synthesis and separation methods known per se. For example, when compound (I) contains an optical isomer, an optical isomer resolved from this compound is also encompassed in compound (I).

The optical isomer can be produced according to a method known per se. To be specific, an optically active synthetic intermediate is used, or the final racemate product is subjected to optical resolution according to a conventional method to give an optical isomer.

For example, the method of optical resolution may be a method known per se, such as a fractional recrystallization method, a chiral column method, a diastereomer method etc.

1) Fractional Recrystallization Method

A method wherein a salt with a racemate with an optically active compound (e.g., (+)-mandelic acid, (−)-mandelic acid, (+)-tartaric acid, (−)-tartaric acid, (+)-1-phenethylamine, (−)-1-phenethylamine, cinchonine, (−)-cinchonidine, brucine etc.) is formed, which is separated by a fractional recrystallization method, and if desired, a neutralization step to give a free optical isomer.

2) Chiral Column Method

A method wherein a racemate or a salt thereof is applied to a column for separation of an optical isomer (a chiral column) to allow separation. In the case of a liquid chromatography, for example, a mixture of the optical isomers is applied to a chiral column such as ENANTIO-OVM (manufactured by Tosoh Corporation), CHIRAL series (manufactured by Daicel Corporation) and the like, and developed with water, various buffers (e.g., phosphate buffer, etc.) and organic solvents (e.g., ethanol, methanol, isopropanol, acetonitrile, trifluoroacetic acid, diethylamine etc.), solely or as a mixed solution thereof to separate the optical isomer.

3) Diastereomer Method

A method wherein a racemic mixture is prepared into a diastereomeric mixture by chemical reaction with an optically active reagent, which is made into a single substance by a typical separation means (e.g., a fractional recrystallization method, a chromatography method etc.) and the like, and is subjected to a chemical treatment such as hydrolysis and the like to remove an optically active reagent moiety, whereby an optical isomer is obtained. For example, when compound (I) contains hydroxy group, or primary or secondary amino group within a molecule, the compound and an optically active organic acid (e.g., MTPA [α-methoxy-α-(trifluoromethyl)phenylacetic acid], (−)-menthoxyacetic acid etc.) and the like are subjected to condensation reaction to give diastereomers of the ester compound or the amide compound, respectively. When compound (I) has a carboxylic acid group, this compound and an optically active amine or an optically active alcohol reagent are subjected to condensation reaction to give diastereomers of the amide compound or the ester compound, respectively. The separated diastereomer is converted to an optical isomer of the original compound by acid hydrolysis or base hydrolysis.

When compound (I) is obtained as a free compound, the compound can be converted to an objective salt according to a method known per se or a method analogous thereto. Conversely, when it is obtained as a salt, the salt can be converted to a free form or other objective salt by a method known per se or a method analogous thereto.

Compound (I) may be a prodrug, and the prodrug of compound (I) refers to a compound which is converted to compound (I) as a result of a reaction with an enzyme, gastric acid, etc. under physiological conditions in vivo, thus a compound that undergoes enzymatic oxidation, reduction, hydrolysis etc. to convert to compound (I) and a compound that undergoes hydrolysis and the like by gastric acid, etc. to convert to compound (I).

Examples of the prodrug for compound (I) include a compound obtained by subjecting an amino group in compound (I) to acylation, alkylation or phosphorylation (e.g., a compound obtained by subjecting an amino group in compound (I) to eicosanoylation, alanylation, pentylaminocarbonylation, (5-methyl-2-oxo-1,3-dioxolen-4-yl)methoxycarbonylation, tetrahydrofurylation, pyrrolidylmethylation, pivaloyloxymethylation, t-butylation and the like);

a compound obtained by subjecting a hydroxy group in compound (I) to acylation, alkylation, phosphorylation or boration (e.g., a compound obtained by subjecting a hydroxy group in compound (I) to acetylation, palmitoylation, propanoylation, pivaloylation, succinylation, fumarylation, alanylation or dimethylaminomethylcarbonylation and the like); a compound obtained by subjecting a carboxyl group in compound (I) to esterification or amidation (e.g., a compound obtained by subjecting a carboxyl group in compound (I) to ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification or methylamidation and the like) and the like. Any of these compounds can be produced from compound (I) according to a method known per se.

A prodrug of compound (I) may also be one which is converted to compound (I) under physiological conditions as described in "IYAKUHIN no KAIHATSU (Development of Pharmaceuticals)", Vol. 7, Design of Molecules, p. 163-198 (HIROKAWA SHOTEN).

Compound (I) may be a crystal, and a single crystal form and a mixture of crystal forms are both encompassed in compound (I) of the present invention. The crystal can be produced by crystallizing according to a crystallization method known per se.

Compound (I) is useful for mammals (e.g., mouse, rat, hamster, rabbit, cat, dog, bovine, sheep, monkey, human etc.) as an agent for the prophylaxis or treatment of diseases, for example, (1) psychiatric diseases [e.g., depression, major depression, bipolar depression, dysthymic disorder, emotional disorder (seasonal affective disorder and the like), recurrent depression, postpartum depression, stress disorder, depression symptom, mania, anxiety, generalized anxiety disorder, anxiety syndrome, panic disorder, phobia, social phobia, social anxiety disorder, obsessive disorder, post-traumatic stress syndrome, post-traumatic stress disorder, Tourette syndrome, autism, fragile X syndrome, Rett syndrome, adjustment disorder, bipolar disorder, neurosis, schizophrenia (e.g., positive symptom, negative symptom, cognitive impairment), chronic fatigue syndrome, anxiety neurosis, compulsive neurosis, epilepsy, anxiety, anxious mental state, emotional abnormality, cyclothymia, nervous erethism, faint, addiction, low sex drive, attention deficit hyperactivity disorder (ADHD), psychotic major depression, refractory major depression, treatment-resistant depression],
(2) neurodegenerative diseases [e.g., Alzheimer's disease, Alzheimer-type senile dementia, Parkinson's disease, Huntington's disease, multi-infarct dementia, frontotemporal dementia, frontotemporal dementia Parkinson's Type, progressive supranuclear palsy, Pick's syndrome, Niemann-Pick syndrome, corticobasal degeneration, Down's disease, vascular dementia, postencephalitic parkinsonism, Lewy body dementia, HIV dementia, amyotrophic lateral sclerosis (ALS), motor neurogenesis disease (MND), Creutzfeldt-Jakob disease or prion disease, cerebral palsy, multiple sclerosis],
(3) age-related cognition memory disorders [e.g., age-related memory disorders, senile dementia]
(4) sleep disorders [e.g., intrinsic sleep disorders (e.g., psychophysiological insomnia and the like), extrinsic sleep disorder, circadian rhythm disorders (e.g., time zone change syndrome (jet lag), shift work sleep disorder, irregular sleep-wake pattern, delayed sleep phase syndrome, advanced sleep phase syndrome, non-24-hour sleep-wake and the like), parasomnia, sleep disorders associated with internal medical or psychiatric disorder (e.g., chronic obstructive pulmonary diseases, Alzheimer's disease, Parkinson's disease, cerebrovascular dementia, schizophrenia, depression, anxiety neurosis), stress insomnia, insomnia, insomniac neurosis, sleep apnea syndrome],
(5) respiratory depression caused by anesthetics, traumatic disease, or neurodegenerative disease and the like,
(6) traumatic brain injury, cerebral apoplexy, neurotic anorexia, eating disorder, anorexia nervosa, hyperorexia, other eating disorder, alcohol dependence, alcohol abuse, alcoholic amnesia, alcohol paranoia, alcohol preference, alcohol withdrawal, alcoholic insanity, alcohol poisoning, alcoholic jealousy, alcoholic mania, alcohol-dependent psychiatric disorder, alcoholic insanity, pharmacophilia, pharmacophobia, pharmacomania, drug withdrawal, migraine, stress headache, catatonic headache, diabetic neuropathy, obesity, diabetes, muscular spasm, Meniere's disease, autonomic ataxia, alopecia, glaucoma, hypertension, cardiac disease, tachycardia, congestive cardiac failure, hyperventilation, bronchial asthma, apnea, sudden infant death syndrome, inflammatory disease, allergic disease, impotence, climacteric disorder, infertility, cancer, immunodeficiency syndrome caused by HIV infection, immunodeficiency syndrome caused by stress, cerebrospinal meningitis, acromegaly, incontinence, metabolic syndrome, osteoporosis, peptic ulcer, irritable bowel syndrome, inflammatory bowel disease, ulcerative colitis, Crohn's disease, stress gastrointestinal disorder, nervous vomiting, peptic ulcer, diarrhea, constipation, postoperative ileus, stress gastrointestinal disorder,
(7) pain (pain)
and the like.
Compound (I) is particularly preferably effective as a cholinergic muscarinic M1 receptor function enhancer, a prophylactic or therapeutic drug for Alzheimer's disease, schizophrenia, pain (pain), sleep disorder and the like.

Since compound (I) has an excellent cholinergic muscarinic M1 receptor positive allosteric modulator activity, it is expected to provide an excellent prophylactic or therapeutic effect for the above-mentioned diseases.

The "positive allosteric modulator" refers to a compound having an action to potentiate a receptor activating function that an endogenous activator (acetylcholine for this receptor) has, by binding to a site different from that of the endogenous activator to enhance the affinity of the endogenous activator.

The "cholinergic muscarinic M1 receptor positive allosteric modulator" refers to a compound having an action on M1 receptor, which is one of the subtypes of muscarinic receptor (named based on the selective activation of the receptor by muscarine) that is one kind of receptor for excitatory endogenous neurotransmitter acetylcholine, to potentiate a receptor activating function that acetylcholine has, by binding to a site different from that of acetylcholine to enhance the affinity of acetylcholine and the like.

The "cholinergic muscarinic M1 receptor positive allosteric modulation (cholinergic muscarinic M1 receptor positive allosteric modulate)" refers to an action to potentiate a receptor activating function that acetylcholine has, through an effect of enhancing the affinity of acetylcholine and the like, which is afforded by the binding of a positive allosteric modulator to a site different from that of acetylcholine in M1 receptor, which is one of the subtypes of muscarinic receptor (named based on the selective activation of the receptor by muscarine) that is one kind of receptor for excitatory endogenous neurotransmitter acetylcholine.

The "method of cholinergic muscarinic M1 receptor positive allosteric modulation" is a method of enhancing a receptor activating function that acetylcholine has, comprising binding a positive allosteric modulator to a site different from that of acetylcholine in M1 receptor, which is one of the subtypes of muscarinic receptor (named based on the selective activation of the receptor by muscarine) that is one kind of receptor for excitatory endogenous neurotransmitter acetylcholine, to enhance the affinity of acetylcholine and the like.

Since compound (I) is excellent in in vivo kinetics (e.g., plasma drug half-life, intracerebral migration, metabolic stability), shows low toxicity (e.g., more excellent as a medicament in terms of acute toxicity, chronic toxicity, genetic toxicity, reproductive toxicity, cardiotoxicity, drug interaction, carcinogenicity and the like), and also has excellent properties as a pharmaceutical product such as a few side effects and the like, it can be safely administered orally or parenterally to a mammal (e.g., mouse, rat, hamster, rabbit, cat, dog, bovine, sheep, monkey, human and the like). Examples of the "parenteral" include intravenous, intramuscular, subcutaneous, intra-organ, intranasal, intradermal, instillation, intracerebral, intrarectal, intravaginal, intraperitoneal and intratumor administrations, administration to the vicinity of tumor etc. and direct administration to the lesion.

A preparation containing compound (I) may be any of a solid preparation such as powder, granule, tablet, capsule, orally disintegrable film and the like, or a liquid agent such as syrup, emulsion, injection and the like.

The medicament of the present invention can be produced by a conventional method such as blending, kneading, granulation, tableting, coating, sterilization treatment, emulsification and the like according to the form of the preparation. As for the production of the preparation, for example, each item of the Japanese Pharmacopoeia Preparation General Rules and the like can be referred to. In addition, the medicament of the present invention may be formed into a sustained-release preparation containing an active ingredient and a biodegradable polymer compound. The sustained-release preparation can be produced according to the method described in JP-A-9-263545.

In the preparation of the present invention, the content of compound (I) varies depending on the form of the preparation, but is generally 0.01 to 100% by weight, preferably 0.1 to 50% by weight, more preferably 0.5 to 20% by weight, as the amount of compound (I) relative to the whole preparation.

When compound (I) is used as the above-mentioned pharmaceutical products, it may be used alone or in admixture with a suitable, pharmacologically acceptable carrier, for example, excipients (e.g., starch, lactose, sucrose, calcium carbonate, calcium phosphate, etc.), binders (e.g., starch, arabic gum, carboxymethyl cellulose, hydroxypropyl cellulose, crystalline cellulose, alginic acid, gelatin, polyvinylpyrrolidone, etc.), lubricants (e.g., stearic acid, magnesium stearate, calcium stearate, talc, etc.), disintegrants (e.g., calcium carboxymethylcellulose, talc, etc.), diluents (e.g., water for injection, physiological saline, etc.) and if desired, with the additives (e.g., a stabilizer, a preservative, a colorant, a fragrance, a solubilizing agent, an emulsifier, a buffer, an isotonic agent, etc.) and the like, by a conventional method, which is processed into a dosage form of a solid agent such as powder, fine granule, granule, tablet, capsule and the like or a liquid form such as injection and the like, and safely administered orally or parenterally. When compound (I) is formed as a preparation for topical administration, it can also be directly administered to the affected part of an articular disease. In this case, an injection is preferable. The compound can also be administered as a parenteral agent for topical administration (e.g., intramuscular injection, subcutaneous injection, organ injection, injection to the vicinity of a joint and the like, solid preparation such as implant, granule, powder and the like, liquid such as suspension and the like, ointment etc.) and the like.

For formulation into an injection, for example, compound (I) is formulated into an aqueous suspension with a dispersing agent (e.g., surfactant such as Tween 80, HCO-60 and the like, polysaccharides such as carboxymethylcellulose, sodium alginate, hyaluronic acid and the like, polysorbate etc.), preservative (e.g., methylparaben, propylparaben etc.), isotonic agent (e.g., sodium chloride, mannitol, sorbitol, glucose etc.), buffer (e.g., calcium carbonate etc.), pH adjuster (e.g., sodium phosphate, potassium phosphate etc.) and the like to give a practical preparation for injection. In addition, an oily suspension can be obtained by dispersing the compound together with vegetable oil such as sesame oil, corn oil and the like or a mixture thereof with a phospholipid such as lecithin and the like, or medium-chain triglyceride (e.g., miglyol 812 etc.) to give an injection to be actually used.

The dose of compound (I) varies depending on the subject of administration, administration route and symptoms and is not particularly limited. For example, for oral administration to adult patients (body weight adult 40 to 80 kg, for example, 60 kg) with schizophrenia, the dose is, for example, 0.001 to 1000 mg/kg body weight/day, preferably 0.01 to 100 mg/kg body weight/day, more preferably 0.1 to 10 mg/kg body weight/day, as compound (I). This amount can be administered in one to three portions per day.

A medicament containing the compound of the present invention can be safely administered solely or by mixing with a pharmaceutically acceptable carrier according to a method known per se (e.g., the method described in the Japanese Pharmacopoeia etc.) as the production method of a pharmaceutical preparation, and in the form of, for example, tablet (including sugar-coated tablet, film-coated tablet, sublingual tablet, orally disintegrating tablet, buccal and the like), pill, powder, granule, capsule (including soft capsule, microcapsule), troche, syrup, liquid, emulsion, suspension, release control preparation (e.g., immediate-release preparation, sustained-release preparation, sustained-release microcapsule), aerosol, film (e.g., orally disintegrating film, oral mucosa-adhesive film), injection (e.g., subcutaneous injection, intravenous injection, intramuscular injection, intraperitoneal injection), drip infusion, transdermal absorption type preparation, ointment, lotion, adhesive preparation, suppository (e.g., rectal suppository, vaginal suppository), pellet, nasal preparation, pulmonary preparation (inhalant), eye drop and the like, orally or parenterally (e.g., intravenous, intramuscular, subcutaneous, intraorgan, intranasal, intradermal, instillation, intracerebral, intrarectal, intravaginal, intraperitoneal administrations, and administration to the lesion).

As the aforementioned "pharmaceutically acceptable carrier", various organic or inorganic carriers conventionally used as preparation materials (starting materials) can be used. For example, excipient, lubricant, binder, disintegrant and the like are used for solid preparations, and solvent, solubilizing agent, suspending agent, isotonic agent, buffer, soothing agent and the like are used for liquid preparations. Where necessary, preparation additives such as preservative, antioxidant, colorant, sweetening agent and the like can also be used.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

While the pharmaceutical composition varies according to the dosage form, administration method, carrier and the like, it can be produced according to a conventional method by adding the compound of the present invention in a proportion of generally 0.01-100% (w/w), preferably 0.1-95% (w/w), of the total amount of the preparation.

The compound of the present invention can be used in combination with other active ingredients (hereinafter to be abbreviated as concomitant drug).

Examples of the concomitant drug include the following. benzodiazepine (chlordiazepoxide, diazepam, potassium clorazepate, lorazepam, clonazepam, alprazolam etc.), L-type calcium channel inhibitor (pregabalin etc.), tricyclic or tetracyclic antidepressant (imipramine hydrochloride, amitriptyline hydrochloride, desipramine hydrochloride, clomipramine hydrochloride etc.), selective serotonin reuptake inhibitor (fluvoxamine maleate, fluoxetine hydrochloride, citalopram hydrobromide, sertraline hydrochloride, paroxetine hydrochloride, escitalopram oxalate etc.), serotonin-noradrenaline reuptake inhibitor (venlafaxine hydrochloride, duloxetine hydrochloride, desvenlafaxine hydrochloride etc.), noradrenaline reuptake inhibitor (reboxetine mesylate etc.), noradrenaline-dopamine reuptake inhibitor (bupropion hydrochloride etc.), mirtazapine, trazodone hydrochloride, nefazodone hydrochloride, bupropion hydrochloride, setiptiline maleate, 5-$HT_{1A}$ agonist (buspirone hydrochloride, tandospirone citrate, osemozotan hydrochloride etc.), 5-$HT_3$ antagonist (cyamemazine etc.), heart non-selective β inhibitor (propranolol hydrochloride, oxprenolol hydrochloride etc.), histamine $H_1$ antagonist (hydroxyzine hydrochloride etc.), therapeutic drug for schizophrenia (chlorpromazine, haloperidol, sulpiride, clozapine, trifluoperazine hydrochloride, fluphenazine hydrochloride, olanzapine, quetiapine fumarate, risperidone, aripiprazole etc.), CRF antagonist, other antianxiety drug (meprobamate etc.), tachykinin antagonist (MK-869, saredutant etc.), medicament that acts on metabotropic glutamate receptor, CCK antagonist, β3 adrenaline antagonist (amibegron hydrochloride etc.), GAT-1 inhibitor (tiagabine hydrochloride etc.), N-type calcium channel inhibitor, carbonic anhydrase II inhibitor, NMDA glycine moiety agonist, NMDA antagonist (memantine etc.), peripheral benzodiazepine receptor agonist, vasopressin antagonist, vasopressin V1b antagonist, vasopressin V1a antagonist, phosphodiesterase inhibitor, opioid antagonist, opioid agonist, uridine, nicotinic acid receptor agonist, thyroid hormone (T3, T4), TSH, TRH, MAO inhibitor (phenelzine sulfate, tranylcypromine sulfate, moclobemide etc.), 5-$HT_{2A}$ antagonist, 5-$HT_{2A}$ inverse agonist, COMT inhibitor (entacapone etc.), therapeutic drug for bipolar disorder (lithium carbonate, sodium valproate, lamotrigine, riluzole, felbamate etc.), cannabinoid CB1 antagonist (rimonabant etc.), FAAH inhibitor, sodium channel inhibitor, anti-ADHD drug (methylphenidate hydrochloride, methamphetamine hydrochloride etc.), therapeutic drug for alcoholism, therapeutic drug for autisma, therapeutic drug for chronic fatigue syndrome, therapeutic drug for spasm, therapeutic drug for fibromyalgia syndrome, therapeutic drug for headache, therapeutic drug for insomnia (etizolam, zopiclone, triazolam, zolpidem, ramelteon, indiplon etc.), therapeutic drug for quitting smoking, therapeutic drug for myasthenia gravis, therapeutic drug for cerebral infarction, therapeutic drug for mania, therapeutic drug for hypersomnia, therapeutic drug for pain, therapeutic drug for dysthymia, therapeutic drug for autonomic ataxia, therapeutic drug for male and female sexual dysfunction, therapeutic drug for migraine, therapeutic drug for pathological gambler, therapeutic drug for restless legs syndrome, therapeutic drug for substance addiction, therapeutic drug for alcohol-related syndrome, therapeutic drug for irritable bowel syndrome, therapeutic drug for Alzheimer's disease (donepezil, galanthamine, memantine etc.), therapeutic drug for Parkinson's disease, therapeutic drug for ALS (riluzole, neurotrophic factor etc.), therapeutic drug for lipid abnormality such as cholesterol-lowering drug (statin series (pravastatin sodium, atorvastatin, simvastatin, rosuvastatin etc.), fibrate (clofibrate etc.), squalene synthetase inhibitor), therapeutic drug for abnormal behavior or suppressant of dromomania due to dementia (sedatives, antianxiety drug etc.), apoptosis inhibitor, antiobesity drug, therapeutic drug for diabetes, therapeutic drug for hypertension, therapeutic drug for hypotension, therapeutic drug for rheumatism (DMARD), anti-cancer agent, therapeutic drug for hypothyroidism (PTH), calcium receptor antagonist, sex hormone or a derivative thereof (progesterone, estradiol, estradiol benzoate etc.), neuronal differentiation promoter, nerve regeneration promoter, non-steroidal anti-inflammatory drug (meloxicam, tenoxicam, indomethacin, ibuprofen, celecoxib, rofecoxib, aspirin etc.), steroid (dexamethasone, cortisone acetate etc.), anti-cytokine drug (TNF inhibitor, MAP kinase inhibitor etc.), antibody medicament, nucleic acid or nucleic acid derivative, aptamer drug and the like.

By combining the compound of the present invention and a concomitant drug, a superior effect such as (1) the dose can be reduced as compared to single administration of the compound of the present invention or a concomitant drug, (2) the drug to be combined with the compound of the present invention can be selected according to the condition of patients (mild case, severe case and the like), (3) the period of treatment can be set longer by selecting a concomitant drug having different action and mechanism from the compound of the present invention, (4) a sustained treatment effect can be designed by selecting a concomitant drug having different action and mechanism from the compound of the present invention, (5) a synergistic effect can be afforded by a combined use of the compound of the present invention and a concomitant drug, and the like, can be achieved.

Hereinafter the compound of the present invention and a concomitant drug used in combination are referred to as the "combination agent of the present invention".

When using the combination agent of the present invention, the administration time of the compound of the present invention or a pharmaceutical composition thereof and the concomitant drug or a pharmaceutical composition thereof is not restricted, and the compound of the present invention or the concomitant drug can be administered to an administration subject simultaneously, or may be administered at different times. The dosage of the concomitant drug may be determined according to the dose clinically used, and can be appropriately selected depending on an administration subject, administration route, disease, combination and the like.

The administration mode of the combination drug of the present invention is not particularly restricted, and it is sufficient that the compound of the present invention and the concomitant drug are combined in administration. Examples of such administration mode include the following methods: (1) administration of a single preparation obtained by simultaneously processing the compound of the present invention and the concomitant drug, (2) simultaneous administration of two kinds of preparations of the compound of the present invention and the concomitant drug, which have been separately produced, by the same administration route, (3) administration of two kinds of preparations of the compound of the present invention and the concomitant drug, which have been separately produced, by the same administration route in a staggered manner, (4) simultaneous administration of two kinds of preparations of the compound of the present invention and the concomitant drug, which have been separately produced, by different administration routes, (5) administration of two kinds of preparations of the compound of the present invention and the concomitant drug, which have been separately produced, by different administration routes in a staggered manner (e.g., administration in the order of the compound of the present invention and the concomitant drug, or in the reverse order) and the like.

The combination drug of the present invention exhibits low toxicity. For example, the compound of the present invention or(and) the aforementioned concomitant drug can be combined with a pharmacologically acceptable carrier according to the known method to prepare a pharmaceutical composition such as tablets (including sugar-coated tablet and film-coated tablet), powders, granules, capsules (including soft capsule), liquids, injections, suppositories, sustained-release agents, etc. These compositions can be administered safely orally or non-orally (e.g., topical, rectal, intravenous administration etc.). Injection can be administered intravenously, intramuscularly, subcutaneously, or by intraorgan administration or directly to the lesion.

Examples of the pharmacologically acceptable carriers usable for the production of a combination agent in the present invention, various organic or inorganic carrier substances conventionally used as preparation materials can be mentioned. For solid preparations, for example, excipient, lubricant, binder and disintegrant can be used. For liquid preparations, for example, solvent, solubilizing agent, suspending agent, isotonic agent, buffering agent, soothing agent and the like can be used. Where necessary, conventional preservative, antioxidant, colorant, sweetening agent, adsorbent, wetting agent and the like can be used as appropriate.

Examples of the excipient include lactose, sucrose, D-mannitol, starch, corn starch, crystalline cellulose, light anhydrous silicic acid and the like.

Examples of the lubricant include magnesium stearate, calcium stearate, talc, colloidal silica and the like.

Examples of the binder include crystalline cellulose, white sugar, D-mannitol, dextrin, hydroxypropylcellulose, hydroxypropylmethylcellulose, polyvinylpyrrolidone, starch, sucrose, gelatin, methylcellulose, carboxymethylcellulose sodium and the like.

Examples of the disintegrant include starch, carboxymethylcellulose, carboxymethylcellulose calcium, sodium carboxymethyl starch, L-hydroxypropylcellulose and the like.

Examples of the solvent include water for injection, alcohol, propylene glycol, macrogol, sesame oil, corn oil, olive oil and the like.

Examples of the solubilizing agent include polyethylene glycol, propylene glycol, D-mannitol, benzyl benzoate, ethanol, trisaminomethane, cholesterol, triethanolamine, sodium carbonate, sodium citrate and the like.

Examples of the suspending agent include surfactants such as stearyl triethanolamine, sodium lauryl sulfate, laurylaminopropionic acid, lecithin, benzalkonium chloride, benzetonium chloride, glycerin monostearate and the like; hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; and the like.

Examples of the isotonic agent include glucose, D-sorbitol, sodium chloride, glycerin, D-mannitol and the like.

Examples of the buffer include buffer solutions such as phosphates, acetates, carbonates, citrates and the like.

Examples of the soothing agent include benzyl alcohol and the like.

Examples of the preservative include p-oxybenzoates, chlorobutanol, benzyl alcohol, phenylethyl alcohol, dehydroacetic acid, sorbic acid and the like.

Examples of the antioxidant include sulfite, ascorbic acid, α-tocopherol and the like.

The mixing ratio of the compound of the present invention to the concomitant drug in the combination agent of the present invention can be appropriately selected depending on an administration subject, administration route, diseases and the like.

For example, the content of the compound of the present invention in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of the concomitant drug in the combination agent of the present invention differs depending on the form of a preparation, and usually from about 0.01 to about 100 wt %, preferably from about 0.1 to about 50 wt %, further preferably from about 0.5 to about 20 wt %, based on the preparation.

The content of additives such as a carrier and the like in the combination agent of the present invention differs depending on the form of a preparation, and usually from about 1 to about 99.99 wt %, preferably from about 10 to about 90 wt %, based on the preparation.

When the compound of the present invention and a concomitant drug are separately formulated into preparations, the contents thereof are similar to the above.

EXAMPLES

The present invention is explained in detail in the following by referring to Reference Examples, Examples, Experimental Examples and Formulation Examples, which are not to be construed as limitative, and the invention may be changed within the scope of the present invention.

In the following Examples, the "room temperature" generally means about 10° C. to about 35° C. The ratios indicated for mixed solvents are volume mixing ratios, unless otherwise specified. % means wt %, unless otherwise specified.

In the following Reference Examples and Examples, the following abbreviations are used.

THF: tetrahydrofuran
DMF: N,N-dimethylformamide
DMSO: dimethyl sulfoxide
DME: 1,2-dimethoxyethane
$^1$H NMR (proton nuclear magnetic resonance spectrum) was measured by Fourier-transform NMR. For the analysis, ACD/SpecManager (trade name) and the like were used. Peaks with very mild protons such as a hydroxy group, an amino group and the like are not sometimes described.

MS (mass spectrum) was measured by LC/MS (liquid chromatography mass spectrometer). As Ionization, ESI (Electro Spray Ionization) method, or APCI (Atmospheric Pressure Chemical Ionization) method was used. The data indicates those found.

Reference Example 1

5,8-difluoro-1-(4-methoxybenzyl)-4-oxo-1,4-dihydroquinoline-3-carboxylic acid

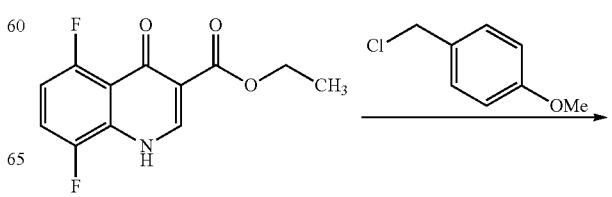

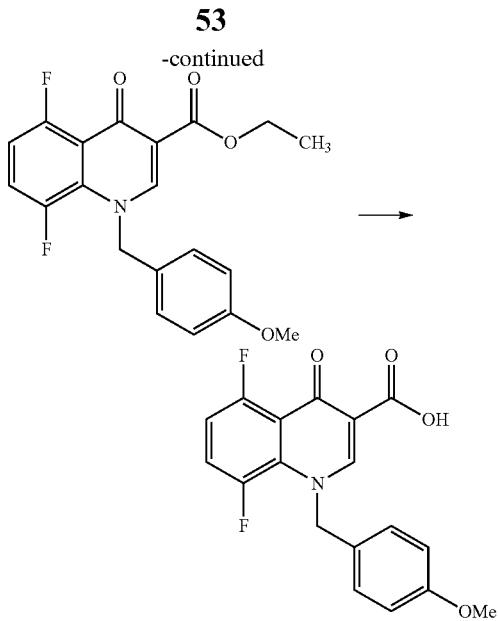

To a solution of ethyl 5,8-difluoro-4-oxo-1,4-dihydroquinoline-3-carboxylate (5.0 g), potassium iodide (3.3 g) and potassium carbonate (4.1 g) in DMF (100 mL) was added 1-(chloromethyl)-4-methoxybenzene (4.6 g), and the mixture was stirred at 70° C. for 14 hr. The reaction mixture was diluted with water and ethyl acetate, and the organic layer was separated, washed with saturated brine, dried over anhydrous sodium sulfate, and concentrated. The obtained residue was dissolved in ethanol-THF (1:1, 40 mL), 1 N aqueous sodium hydroxide solution (20 mL) was added, and the mixture was stirred at room temperature for 6 hr. The reaction mixture was diluted with water, neutralized with 1 N hydrochloric acid (20 mL), and the precipitate was collected by filtration, washed with water, and dried to give the title compound (4.4 g).

$^1$H NMR (400 MHz, DMSO-$d_6$) δ 3.34 (3H, s), 5.79 (2H, d, J=3.7 Hz), 6.90 (2H, d, J=8.6 Hz), 7.12 (2H, d, J=8.6 Hz), 7.36-7.45 (1H, m), 7.73-7.84 (1H, m), 9.13 (1H, s), 14.79 (1H, s).

Reference Example 2

1-(4-methoxybenzyl)-4-oxo-1,4-dihydrocinnoline-3-carboxylic acid

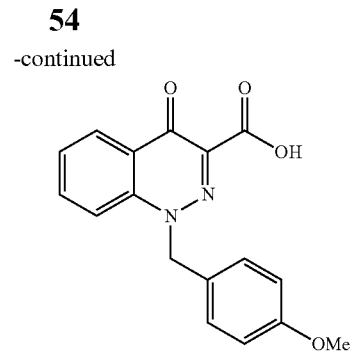

To a solution of ethyl 4-oxo-1,4-dihydrocinnoline-3-carboxylate (2.0 g), potassium iodide (1.5 g) and potassium carbonate (2.5 g) in DMF (50 mL) was added 1-(chloromethyl)-4-methoxybenzene (1.4 mL), and the mixture was stirred at 70° C. for 14 hr. The reaction mixture was diluted with water and ethyl acetate, and the organic layer was separated, washed with saturated brine, dried over anhydrous sodium sulfate, and concentrated. The obtained residue was dissolved in ethanol-THF (1:1, 30 mL), 1 N aqueous sodium hydroxide solution (15 mL) was added, and the mixture was stirred at room temperature for 6 hr. The reaction mixture was diluted with water, neutralized with 1 N hydrochloric acid (15 mL), and the precipitate was collected by filtration, washed with water, and dried to give the title compound (1.1 g).

$^1$H NMR (400 MHz, DMSO-$d_6$) δ 3.71 (3H, s), 5.88 (2H, s), 6.91 (2H, d, J=8.6 Hz), 7.31 (2H, d, J=8.6 Hz), 7.69 (1H, t, J=7.6 Hz), 7.97 (1H, t, J=7.5 Hz), 8.03-8.11 (1H, m), 8.31 (1H, d, J=7.8 Hz), 14.35 (1H, brs).

Reference Example 3

1-(4-carbamoylbenzyl)-4-oxo-1,4-dihydroquinoline-3-carboxylic acid

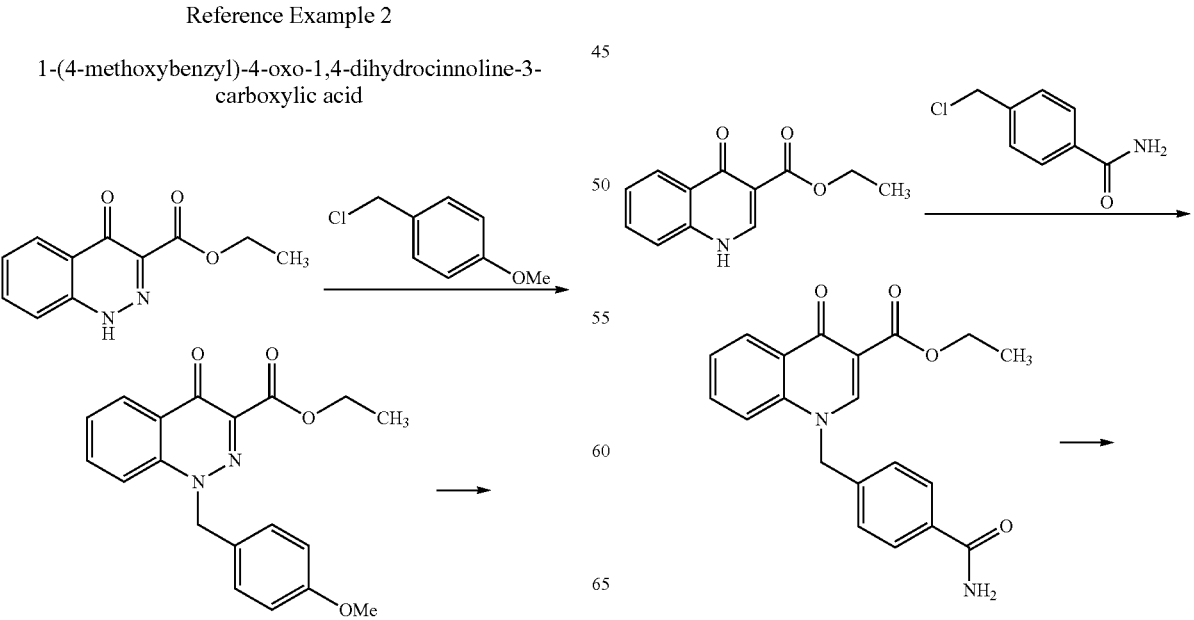

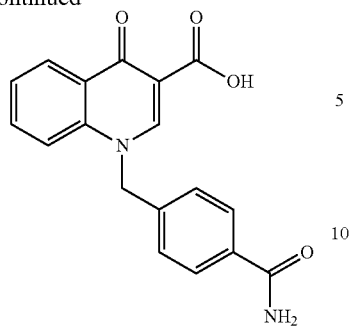

In the same manner as in Reference Example 1, the title compound (0.40 g) was obtained from ethyl 4-oxo-1,4-dihydroquinoline-3-carboxylate (1.0 g) and 4-(chloromethyl)benzamide (0.78 g).

$^1$H NMR (300 MHz, DMSO-$d_6$) δ 5.94 (2H, s), 7.24-7.43 (3H, m), 7.55-7.68 (1H, m), 7.74-8.00 (5H, m), 8.41 (1H, d, J=8.3 Hz), 9.32 (1H, s), 15.15 (1H, s).

Reference Example 4

1-(4-carbamoylbenzyl)-4-oxo-1,4-dihydrocinnoline-3-carboxylic acid

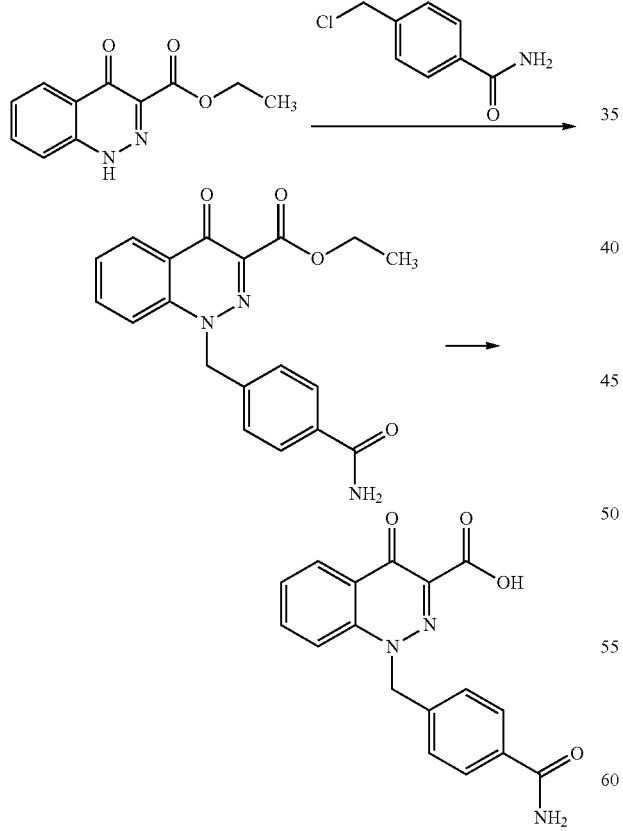

In the same manner as in Reference Example 1, the title compound (0.39 g) was obtained from ethyl 4-oxo-1,4-dihydrocinnoline-3-carboxylate (1.0 g) and 4-(chloromethyl)benzamide (0.78 g).

$^1$H NMR (300 MHz, DMSO-$d_6$) δ 6.01 (2H, s), 7.38 (3H, d, J=8.3 Hz), 7.69 (1H, dt, J=7.8, 4.1 Hz), 7.83 (2H, d, J=8.3 Hz), 7.95 (3H, d, J=3.4 Hz), 8.32 (1H, d, J=8.0 Hz), 14.29 (1H, brs).

Reference Example 5

1-(4-carbamoylbenzyl)-4-oxo-8-(trifluoromethoxy)-1,4-dihydroquinoline-3-carboxylic acid

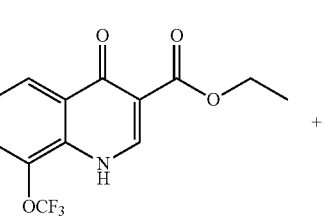

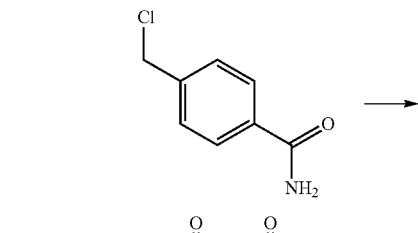

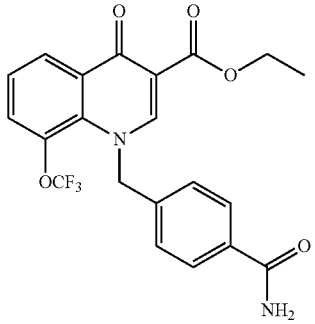

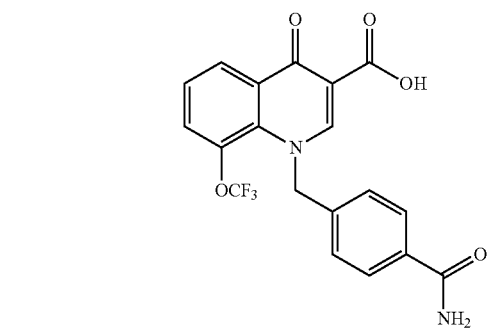

In the same manner as in Reference Example 1, the title compound (0.75 g) was obtained from ethyl 4-oxo-8-(trifluoromethoxy)-1,4-dihydroquinoline-3-carboxylate (1.0 g) and 4-(chloromethyl)benzamide (0.62 g).

$^1$H NMR (400 MHz, DMSO-$d_6$) δ 5.97 (2H, s), 7.12 (2H, d, J=7.8 Hz), 7.37 (1H, brs), 7.67-7.75 (1H, m), 7.79 (2H, d, J=7.6 Hz), 7.88 (1H, d, J=7.8 Hz), 7.95 (1H, brs), 8.47 (1H, d, J=7.8 Hz), 9.20 (1H, s), 14.64 (1H, s).

Reference Example 6

1-(chloromethyl)-4-(1,1-difluoroethyl)benzene

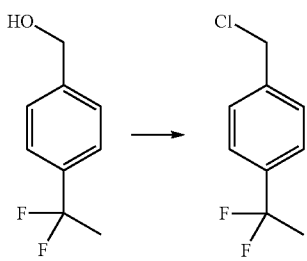

A solution of [4-(1,1-difluoroethyl)phenyl]methanol (336 mg, 1.95 mmol) obtained by reference to a document (Tetrahedron, 1975, 31, 391.), methanesulfonyl chloride (0.453 mL, 5.85 mmol) and triethylamine (0.82 mL) in THF (5 mL) was stirred at 50° C. for 14 hr. The reaction mixture was diluted with ethyl acetate, washed with saturated brine, and the organic layer was dried over anhydrous sodium sulfate, and concentrated. The residue was purified by silica gel column chromatography (hexane-ethyl acetate) to give the title compound (0.28 g).

$^1$H NMR (400 MHz, DMSO-$d_6$) δ 1.96 (3H, t, J=18.8 Hz), 4.81 (2H, s), 7.41-7.73 (4H, m).

Reference Example 7

1-[4-(1,1-difluoroethyl)benzyl]-4-oxo-1,4-dihydroquinoline-3-carboxylic acid

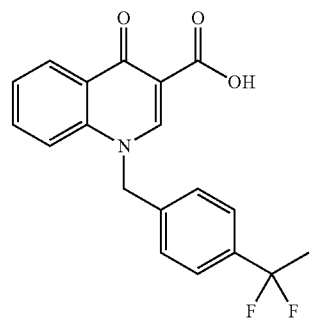

In the same manner as in Reference Example 1, the title compound (0.079 g) was obtained from ethyl 4-oxo-1,4-dihydroquinoline-3-carboxylate (0.10 g) and 1-(chloromethyl)-4-(1,1-difluoroethyl)benzene (0.10 g) obtained in Reference Example 6.

$^1$H NMR (400 MHz, DMSO-$d_6$) δ 1.92 (3H, t, J=19.0 Hz), 5.94 (2H, s), 7.38 (2H, d, J=8.1 Hz), 7.54 (2H, d, J=8.1 Hz), 7.63 (1H, t, J=7.1 Hz), 7.77-7.94 (2H, m), 8.40 (1H, d, J=6.8 Hz), 9.33 (1H, s), 15.15 (1H, brs).

Reference Example 8

1-[4-(1H-pyrazol-1-yl)benzyl]-4-oxo-1,4-dihydrocinnoline-3-carboxylic acid

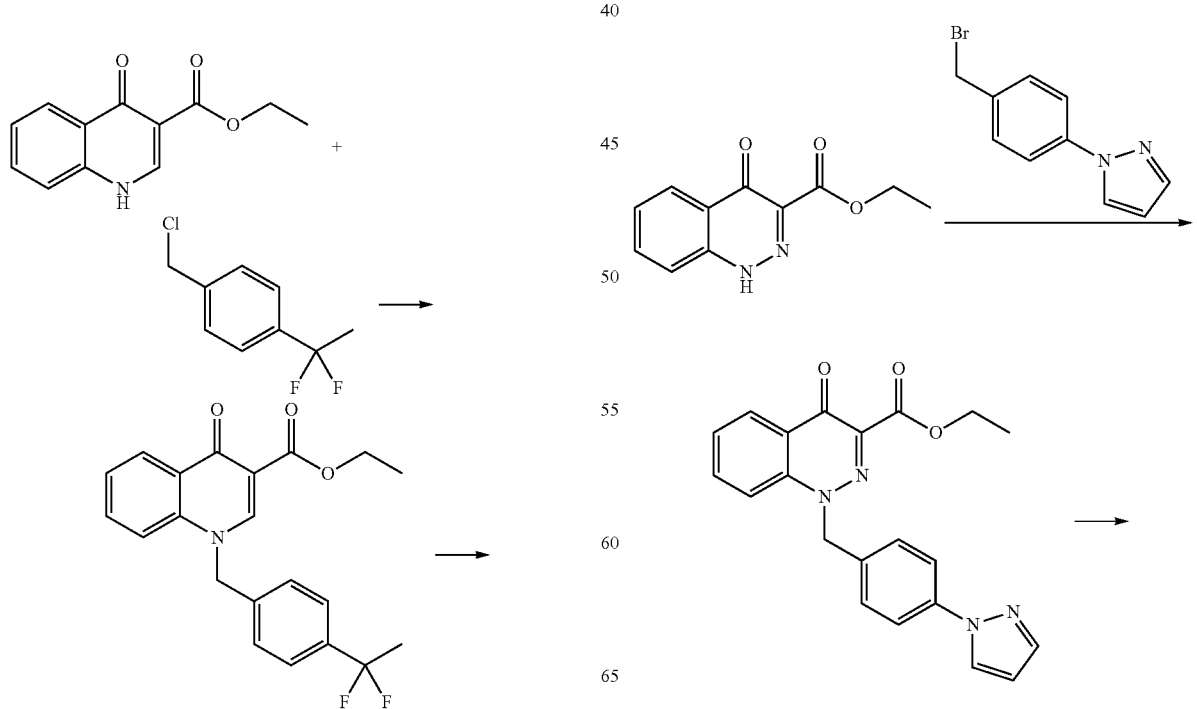

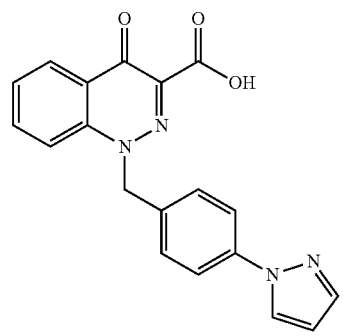

In the same manner as in Reference Example 1, the title compound (0.35 g) was obtained from ethyl 4-oxo-1,4-dihydrocinnoline-3-carboxylate (0.40 g) and 1-[4-(bromomethyl)phenyl]-1H-pyrazole (0.48 g).

$^1$H NMR (400 MHz, DMSO-$d_6$) δ 6.00 (2H, s), 6.53 (1H, s), 7.47 (2H, d, J=8.6 Hz), 7.66-7.75 (2H, m), 7.82 (2H, d, J=8.3 Hz), 7.93-8.00 (1H, m), 8.01-8.08 (1H, m), 8.33 (1H, d, J=8.1 Hz), 8.47 (1H, d, J=2.2 Hz), 14.33 (1H, brs).

Reference Example 9

8-chloro-1-(4-methoxybenzyl)-4-oxo-1,4-dihydroquinoline-3-carboxylic acid

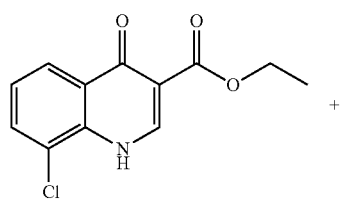

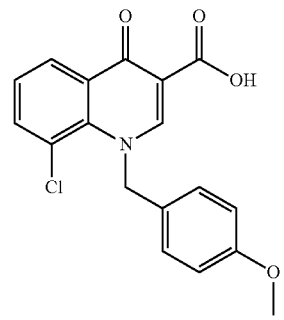

To a solution of ethyl 4-oxo-8-chloro-1,4-dihydroquinoline-3-carboxylate (1.0 g), potassium iodide (0.66 g) and sodium carbonate (1.1 g) in DMF (20 mL) was added 1-(chloromethyl)-4-methoxybenzene (0.7 mL), and the mixture was stirred at 70° C. overnight. The reaction mixture was diluted with water and ethyl acetate, and the organic layer was separated, washed with saturated brine, dried over anhydrous sodium sulfate, and concentrated. The residue was solidified with a diisopropyl ether-ethyl acetate mixed solution. The obtained solid was dissolved in ethanol-THF (1:1, 12 mL), 1 N aqueous sodium hydroxide solution (6 mL) was added, and the mixture was stirred at room temperature for 6 hr. The reaction mixture was diluted with water, neutralized with 1 N hydrochloric acid (10 mL), and the precipitate was collected by filtration, washed with water, and dried to give the title compound (0.52 g).

$^1$H NMR (400 MHz, DMSO-$d_6$) δ 3.70 (3H, s), 6.15 (2H, s), 6.88 (2H, d, J=8.8 Hz), 7.05 (2H, d, J=8.8 Hz), 7.61 (1H, t, J=7.9 Hz), 7.99 (1H, dd, J=7.8, 1.5 Hz), 8.43 (1H, dd, J=8.1, 1.5 Hz), 9.10 (1H, s), 14.64 (1H, s).

Reference Example 10

3-benzyltetrahydrobenzo[d]oxazole-2,5(3H,6H)-dione

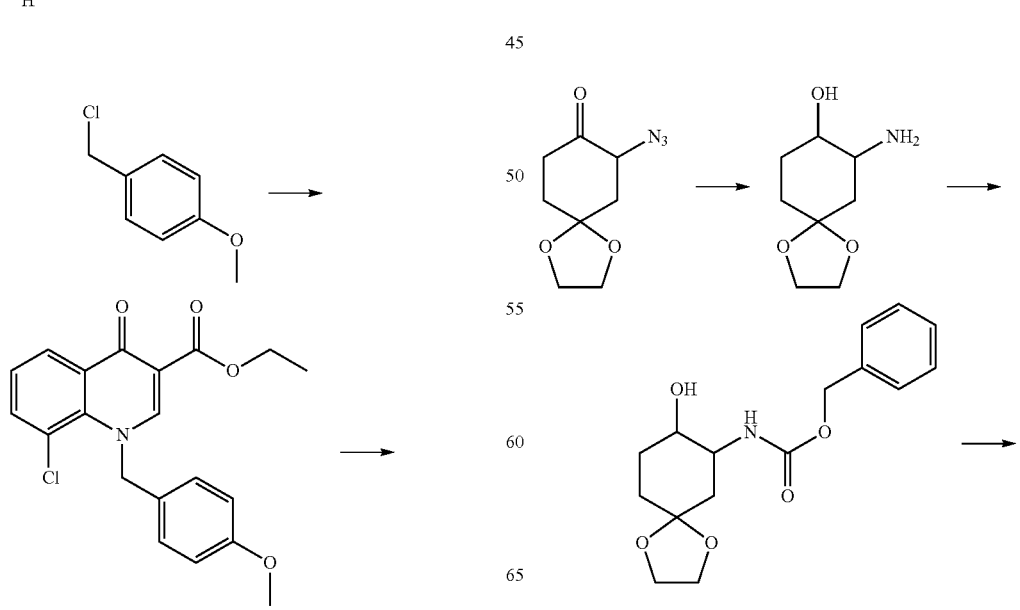

-continued

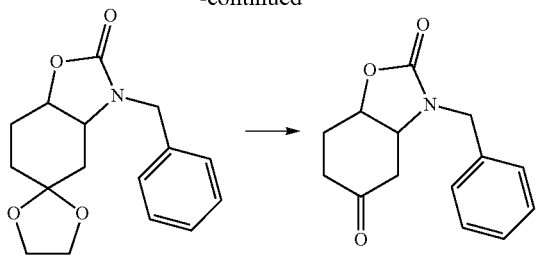

A solution of lithium aluminum hydride (4.42 g) in THF (100 mL) was ice-cooled under a nitrogen atmosphere, and a solution of 7-azido-1,4-dioxaspiro[4.5]decan-8-one (11.5 g) known from a document (Tetrahedron, 1995, 51, 11075.) in THF (100 mL) was added dropwise. After confirmation of the completion of the reaction by TLC, sodium sulfate decahydrate was added. The resulting precipitate was collected by filtration, and extracted by solid-liquid extraction using dichloromethane. The filtrate was concentrated, and the residue was dissolved in a dioxane-saturated aqueous sodium hydrogen carbonate mixed solution (1:1, 400 mL). To the solution was added benzyl chloroformate (14.9 g), and the mixture was stirred at room temperature overnight. The reaction mixture was diluted with dichloromethane, and the organic layer was washed with water and saturated brine, dried over anhydrous sodium sulfate, and concentrated. To a solution of the residue in DMF (80 mL) was added sodium hydride (60% in oil, 4.15 g) and the mixture was stirred for 30 min. Benzyl bromide (22.2 g) was added, and the mixture was stirred overnight. To the reaction solution was added methanol (10 mL), and the mixture was stirred for 10 min. The solvent was evaporated under reduced pressure and dichloromethane was added to the residue. The precipitate was filtered off, and the filtrate was concentrated. To the residue was added acetone-1 N hydrochloric acid (3:1, 800 mL), and the mixture was stirred at 60° C. for 2 days. Acetone was evaporated under reduced pressure, and saturated sodium hydrogen carbonate was added to the aqueous layer to adjust the solution to pH>9. To the solution was added dichloromethane, and the organic layer was separated, dried over anhydrous sodium sulfate, and concentrated. The residue was purified by silica gel chromatography (petroleum ether-ethyl acetate) to give the title compound (6.98 g) as a white solid.

$^1$H NMR (400 MHz, CDCl$_3$) δ 1.93-2.02 (1H, m), 2.33-2.49 (3H, m), 2.63-2.71 (2H, m), 3.31-3.38 (1H, m), 4.27-4.34 (2H, m), 4.56 (1H, d, J=14.8 Hz), 7.31-7.40 (5H, m).

Reference Example 11

3-benzyl-5,5-difluorohexahydrobenzo[d]oxazol-2 (3H)-one

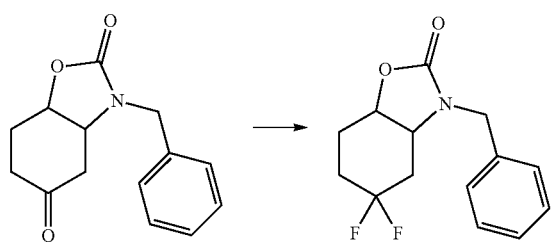 [SMILES: O=C1CCC2OC(=O)N(Cc3ccccc3)C2C1 ; O=C1OC2CCC(F)(F)CC2N1Cc1ccccc1]

To a solution of 3-benzyltetrahydrobenzo[d]oxazole-2,5 (3H,6H)-dione (1.37 g) obtained in Reference Example 10 in dichloromethane (100 mL) was added dropwise diethylaminosulfur trifluoride (1.8 g) under ice-cooling, and the mixture was stirred at room temperature overnight. The reaction solution was diluted with dichloromethane, and washed with water and saturated brine, and the organic layer was dried over anhydrous sodium sulfate, and concentrated. The residue was purified by silica gel column chromatography (petroleum ether-ethyl acetate) to give the title compound (0.98 g) as a white solid.

$^1$H NMR (400 MHz, CDCl$_3$): δ 1.65-1.93 (3H, m), 2.22-2.34 (3H, m), 3.23-3.29 (1H, m), 3.89-3.95 (1H, m), 4.36-4.46 (2H, m), 7.27-7.38 (5H, m).

Reference Example 12

2-(benzylamino)-4,4-difluorocyclohexanol

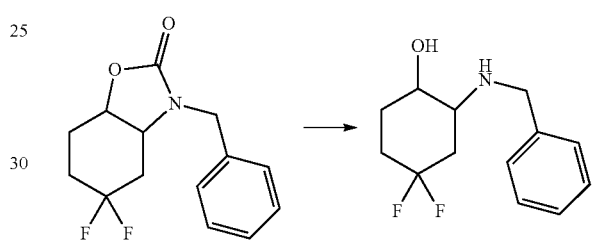

To a solution of 3-benzyl-5,5-difluorohexahydrobenzo[d] oxazol-2(3H)-one (0.98 g) obtained in Reference Example 11 in ethanol-water (10:1, 66 mL) was added potassium hydroxide (0.41 g), and the mixture was stirred at 80° C. overnight. The reaction solution was concentrated, and the residue was purified by silica gel column chromatography (dichloromethane-methanol) to give the title compound (0.54 g) as a white solid.

$^1$H NMR (400 MHz, CDCl$_3$): δ 1.47-1.64 (6H, m), 1.72-1.88 (1H, m), 2.04-2.19 (2H, m), 3.30-3.36 (1H, m), 3.73 (1H, d, J=12.8 Hz), 3.94 (1H, d, J=12.8 Hz), 7.28-7.39 (5H, m).

Reference Example 13

(1,2-trans)-2-amino-4,4-difluorocyclohexanol hydrochloride

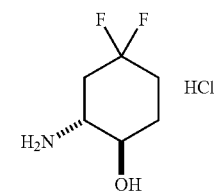

To a solution of 2-(benzylamino)-4,4-difluorocyclohexanol (3.0 g) in methanol (100 mL) obtained in Reference Example 12 was added palladium carbon (0.3 g), and the mixture was stirred under a hydrogen atmosphere at room temperature overnight. Insoluble material was filtered off, and the filtrate was concentrated. The residue was dissolved in 4 N hydrogen chloride (ethyl acetate solution, 100 mL) and concentrated to give the title compound (2.26 g) as a white solid.

$^1$H NMR (400 MHz, CDCl$_3$): δ 1.39-1.48 (1H, m), 1.86-2.11 (4H, m), 2.38-2.45 (1H, m), 2.90-2.96 (1H, m), 3.55-3.62 (1H, m), 5.66 (1H, d, J=5.6 Hz), 8.20 (3H, brs).

Reference Example 14 ethyl 4-oxo-1-{4-[1-(tetrahydro-2H-pyran-2-yl)-1H-pyrazol-5-yl]benzyl}-1,4-dihydroquinoline-3-carboxylate

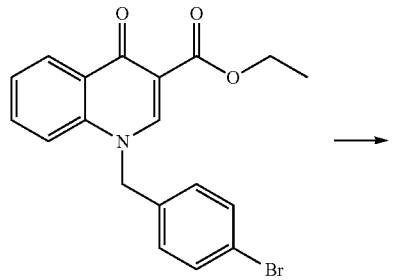

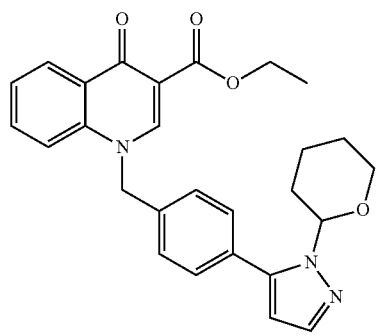

To a suspension of ethyl 1-(4-bromobenzyl)-4-oxo-1,4-dihydroquinoline-3-carboxylate (0.8 g) known from a document (Journal of Medicinal Chemistry, 2007, 50, 5471), 1-(tetrahydro-2H-pyran-2-yl)-5-(4,4,5,5-tetramethyl-1,3,2-dioxaborolan-2-yl)-1H-pyrazole (0.86 g) and potassium phosphate (1.1 g) in DME-water (4:1, 20 mL) was added [1,1-bis(diphenylphosphino)ferrocene]dichloropalladium (II) (0.08 g), and the mixture was stirred at 100° C. for 1 hr under microwave irradiation. The reaction mixture was diluted with ethyl acetate, and the insoluble material was filtered off. The filtrate was washed with saturated brine, dried over anhydrous sodium sulfate, and concentrated. The residue was purified by silica gel chromatography (hexane-ethyl acetate) to give the title compound (0.37 g) as a pale-yellow solid.

$^1$H NMR (400 MHz, DMSO-d$_6$) δ 1.31 (3H, t, J=7.0 Hz), 1.43-1.63 (3H, m), 1.76 (1H, d, J=12.7 Hz), 1.90 (1H, brs), 2.36 (1H, d, J=10.5 Hz), 3.50 (1H, t, J=9.5 Hz), 3.94 (1H, d, J=11.2 Hz), 4.26 (2H, q, J=6.6 Hz), 5.16 (1H, d, J=9.8 Hz), 5.76 (2H, s), 6.43 (1H, s), 7.39 (2H, d, J=7.8 Hz), 7.42-7.57 (4H, m), 7.62-7.76 (2H, m), 8.27 (1H, d, J=8.1 Hz), 8.97 (1H, s).

Reference Example 15

4-oxo-1-{4-[1-(tetrahydro-2H-pyran-2-yl)-1H-pyrazol-5-yl]benzyl}-1,4-dihydroquinoline-3-carboxylic acid

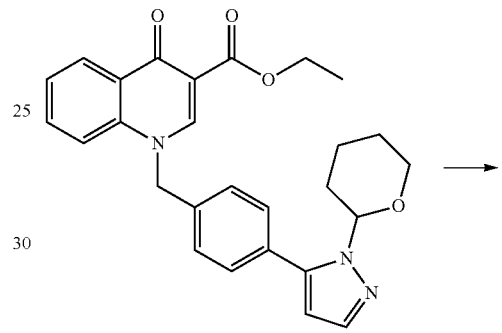

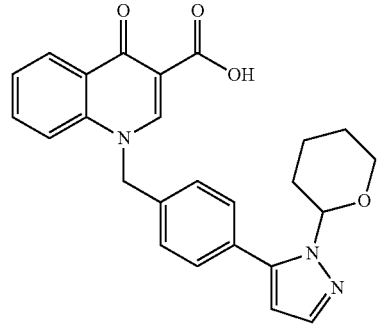

Ethyl 4-oxo-1-{4-[1-(tetrahydro-2H-pyran-2-yl)-1H-pyrazol-5-yl]benzyl}-1,4-dihydroquinoline-3-carboxylate (0.37 g) obtained in Reference Example 14 was dissolved in ethanol-THF (1:1, 10 mL), 1 N aqueous sodium hydroxide solution (5 mL) was added, and the mixture was stirred at room temperature for 6 hr. The reaction mixture was diluted with water and neutralized with 1 N hydrochloric acid (5 mL). The precipitate was collected by filtration, washed with water and dried to give the title compound (0.31 g).

$^1$H NMR (400 MHz, DMSO-d$_6$) δ 1.39-1.62 (3H, m), 1.76 (1H, d, J=12.5 Hz), 1.91 (1H, brs), 2.36 (1H, d, J=10.8 Hz), 3.49 (1H, d, J=9.0 Hz), 3.94 (1H, d, J=10.5 Hz), 5.16 (1H, d, J=9.3 Hz), 5.96 (2H, s), 6.44 (1H, s), 7.42 (2H, d, J=8.1), 7.47-7.58 (3H, m), 7.65 (1H, d, J=3.9 Hz), 7.91 (2H, brs), 8.42 (1H, d, J=8.1 Hz), 9.35 (1H, s), 15.18 (1H, s).

Reference Example 16

1-(4-bromobenzyl)-N-[(1,2-trans)-2-hydroxycyclopentyl]-4-oxo-1,4-dihydroquinoline-3-carboxamide

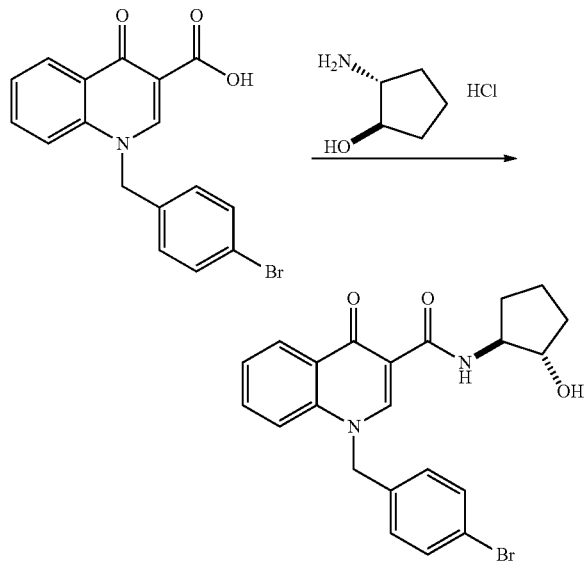

To a solution of 1-(4-bromobenzyl)-4-oxo-1,4-dihydroquinoline-3-carboxylic acid (0.83 g) known from a document (Journal of Medicinal Chemistry, 2007, 50, 5471) in DMF (20 mL) were added (1,2-trans)-2-aminocyclopentanol hydrochloride (0.38 g), O-(7-azabenzotriazol-1-yl)-N,N,N',N'-tetramethyluronium hexafluorophosphate (1.1 g) and triethylamine (0.80 mL), and the mixture was stirred at room temperature overnight. Water was added to the reaction mixture, and the precipitate was collected by filtration and dried to give the title compound (1.0 g) as a pale-yellow solid.

$^1$H NMR (300 MHz, DMSO-$d_6$) δ 1.37-1.94 (5H, m), 2.00-2.17 (1H, m), 3.88-4.10 (2H, m), 5.77 (2H, s), 5.86 (1H, s), 7.13-7.30 (2H, m), 7.44-7.97 (5H, m), 8.29-8.44 (1H, m), 9.08 (1H, s), 10.03 (1H, d, J=7.4 Hz).

Example 1

5,8-difluoro-1-(4-methoxybenzyl)-4-oxo-1,4-dihydroquinoline-3-carboxamide

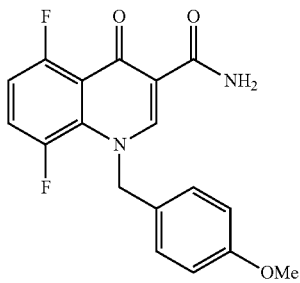 [SMILES: COc1ccc(Cn2cc(C(N)=O)c(=O)c3c(F)ccc(F)c32)cc1]

To a solution of 5,8-difluoro-1-(4-methoxybenzyl)-4-oxo-1,4-dihydroquinoline-3-carboxylic acid (0.065 g) obtained in Reference Example 1, N-[(ethylimino)methylene]-N',N'-dimethylpropane-1,3-diamine hydrochloride (0.058 g) and 1-hydroxybenzotriazole (0.051 g) in DMF (2 mL) was added 2 M ammonia (ethanol solution, 0.19 mL), and the mixture was stirred at room temperature overnight. The reaction mixture was diluted with water and ethyl acetate, and the organic layer was separated, washed with saturated brine, dried over anhydrous sodium sulfate, and concentrated. The residue was purified by silica gel chromatography (hexane-ethyl acetate) to give the title compound (0.048 g).

MS (ESI+): [M+H]$^+$ 345.2

$^1$H NMR (400 MHz, DMSO-$d_6$) δ 3.71 (3H, s), 5.68 (2H, d, J=3.2 Hz), 6.90 (2H, d, J=8.6 Hz), 7.08 (2H, d, J=8.6 Hz), 7.17-7.32 (1H, m), 7.55-7.70 (2H, m), 8.89 (1H, s), 9.01 (1H, d, J=4.2 Hz).

Example 2

5,8-difluoro-1-(4-methoxybenzyl)-4-oxo-N-phenyl-1,4-dihydroquinoline-3-carboxamide

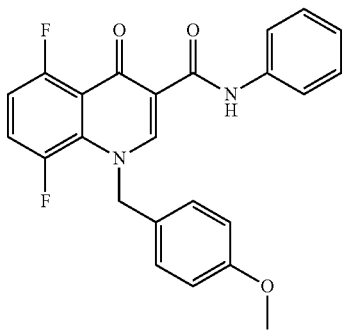 [SMILES: COc1ccc(Cn2cc(C(=O)Nc3ccccc3)c(=O)c3c(F)ccc(F)c32)cc1]

To a solution of 5,8-difluoro-1-(4-methoxybenzyl)-4-oxo-1,4-dihydroquinoline-3-carboxylic acid (28 mg) obtained in Reference Example 1 in DMF (0.5 mL) were added aniline (15 mg), a solution of O-(7-azabenzotriazol-1-yl)-N,N,N',N'-tetramethyluronium hexafluorophosphate (60 mg) in DMF (0.5 mL) and N,N-diisopropylethylamine (0.027 mL), and the mixture was stirred at room temperature for 15 hr. Ethyl acetate (3 mL), saturated aqueous sodium hydrogen carbonate solution (1 mL) and water (1 mL) were added to the reaction solution, and the mixture was stirred. The organic layer was applied to a phase separator, and the eluted organic layer was concentrated by blowing air. The residue was purified by preparative high performance liquid chromatography (acetonitrile/10 mM aqueous ammonium hydrogen carbonate solution) to give the title compound (3.4 mg).

MS (ESI+): [M+H]$^+$ 421.1

$^1$H NMR (400 MHz, DMSO-d) δ 3.71 (3H, s), 5.76 (2H, d, J=2.7 Hz), 6.91 (2H, d, J=8.6 Hz), 7.12 (3H, d, J=8.1 Hz), 7.27-7.41 (3H, m), 7.65-7.78 (3H, m), 9.05 (1H, s), 12.06 (1H, s).

Example 3

5,8-difluoro-N-[(1,2-trans)-2-hydroxycyclohexyl]-4-oxo-1-[4-(1H-pyrazol-1-yl)benzyl]-1,4-dihydro-quinoline-3-carboxamide

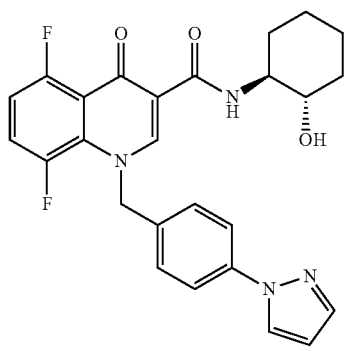 [SMILES: O=C(N[C@H]1CCCC[C@@H]1O)c1cn(Cc2ccc(-n3cccn3)cc2)c2c(F)ccc(F)c2c1=O]

To a solution of 5,8-difluoro-1-[4-(1H-pyrazol-1-yl)benzyl]-4-oxo-1,4-dihydroquinoline-3-carboxylic acid (100 mg) known from a document (Bioorganic and Medicinal Chemistry Letters, 2010, 20, 1334.) in DMF (4 mL) were added (1,2-trans)-2-hydroxycyclohexylamine hydrochloride (60 mg), N1-[(ethylimino)methylene]-N3,N3-dimethylpropane-1,3-diamine hydrochloride (75 mg), 1H-benzo[d][1,2,3]triazol-1-ol monohydrate (60 mg) and triethylamine (0.11 mL), and the mixture was stirred at room temperature for 15 hr. Water (10 mL) was added to the reaction solution, the mixture was stirred, and the precipitated solid was collected by filtration and dried to give the title compound (110 mg).

MS (ESI+): [M+H]$^+$ 479.3

$^1$H NMR (400 MHz, DMSO-d$_6$) δ 1.16-1.38 (4H, m), 1.54-1.70 (2H, m), 1.80-1.91 (1H, m), 1.97-2.07 (1H, m), 3.36-3.44 (1H, m), 3.61-3.71 (1H, m), 4.83 (1H, d, J=4.9 Hz), 5.82 (2H, d, J=2.4 Hz), 6.53 (1H, s), 7.20-7.33 (3H, m), 7.59-7.69 (1H, m), 7.72 (1H, s), 7.80 (2H, d, J=8.3 Hz), 8.45 (1H, d, J=2.4 Hz), 8.93 (1H, s), 9.81 (1H, d, J=7.3 Hz).

Example 4

N-[(1,2-trans)-2-hydroxycyclohexyl]-4-oxo-1-[4-(1H-pyrazol-1-yl)benzyl]-1,4-dihydrocinnoline-3-carboxamide

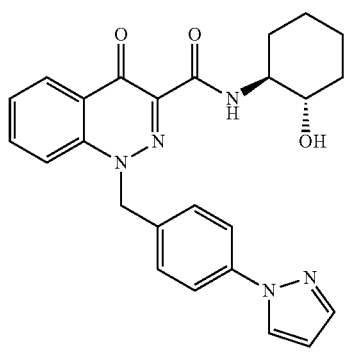 [SMILES: O=C(N[C@H]1CCCC[C@@H]1O)c1nn(Cc2ccc(-n3cccn3)cc2)c2ccccc2c1=O]

To a solution of 1-[4-(1H-pyrazol-1-yl)benzyl]-4-oxo-1,4-dihydrocinnoline-3-carboxylic acid (100 mg) obtained in Reference Example 8 in DMF (4 mL) were added (1,2-trans)-2-hydroxycyclohexylamine hydrochloride (65 mg), N1-[(ethylimino)methylene]-N3,N3-dimethylpropane-1,3-diamine hydrochloride (83 mg), 1H-benzo[d][1,2,3]triazol-1-ol monohydrate (66 mg) and triethylamine (0.11 mL), and the mixture was stirred at room temperature for 15 hr. Water (10 mL) was added to the reaction solution, the mixture was stirred, and the precipitated solid was collected by filtration and dried to give the title compound (104 mg).

MS (ESI+): [M+H]$^+$ 444.2

$^1$H NMR (400 MHz, DMSO-d$_6$) δ 1.20-1.39 (4H, m), 1.57-1.71 (2H, m), 1.87 (1H, brs), 2.06 (1H, brs), 3.37-3.46 (1H, m), 3.65-3.77 (1H, m), 4.84 (1H, d, J=4.9 Hz), 5.95 (2H, s), 6.53 (1H, s), 7.44 (2H, d, J=8.6 Hz), 7.62 (1H, t, J=7.5 Hz), 7.72 (1H, s), 7.81 (2H, d, J=8.6 Hz), 7.85-7.99 (2H, m), 8.30 (1H, d, J=8.1 Hz), 8.46 (1H, d, J=2.2 Hz), 9.78 (1H, d, J=7.6 Hz).

Example 5

1-(4-carbamoylbenzyl)-N-[(1S,2S)-2-hydroxycyclohexyl]-4-oxo-1,4-dihydroquinoline-3-carboxamide

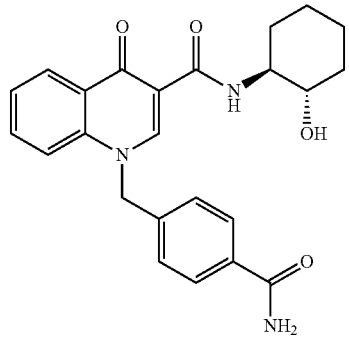

To a solution of 1-(4-carbamoylbenzyl)-4-oxo-1,4-dihydroquinoline-3-carboxylic acid (200 mg) obtained in Reference Example 3 in DMF (5 mL) were added (1S,2S)-2-hydroxycyclohexylamine hydrochloride (93 mg), O-(7-azabenzotriazol-1-yl)-N,N,N',N'-tetramethyluronium hexafluorophosphate (353 mg) and triethylamine (0.26 mL), and the mixture was stirred at room temperature for 15 hr. Water (10 mL) was added to the reaction solution, the mixture was stirred, and the precipitated solid was collected by filtration.

The crude crystals were recrystallized from ethanol to give the title compound (162 mg).

MS (ESI+): [M+H]$^+$ 420.3

$^1$H NMR (300 MHz, DMSO-d$_6$) δ 1.30 (4H, d, J=8.3 Hz), 1.55-1.71 (2H, m), 1.87 (1H, d, J=8.3 Hz), 2.03 (1H, d, J=10.6 Hz), 3.34-3.46 (1H, m), 3.71 (1H, d, J=8.7 Hz), 4.81 (1H, d, J=4.9 Hz), 5.85 (2H, s), 7.28 (2H, d, J=8.3 Hz), 7.34 (1H, brs), 7.50 (1H, t, J=7.2 Hz), 7.65-7.77 (2H, m), 7.82 (2H, d, J=8.3 Hz), 7.92 (1H, brs), 8.36 (1H, d, J=7.6 Hz), 9.09 (1H, s), 10.08 (1H, d, J=7.6 Hz).

Example 6

1,5-anhydro-2,3-dideoxy-3-({[5,8-difluoro-1-(4-methoxybenzyl)-4-oxo-1,4-dihydroquinolin-3-yl]carbonyl}amino)-DL-threo-pentitol

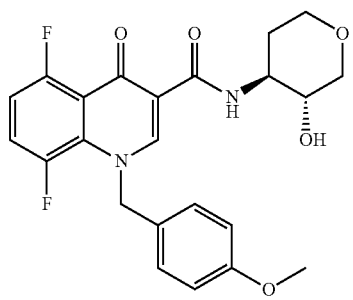 [SMILES: COc1ccc(Cn2cc(C(=O)N[C@H]3CCOC[C@@H]3O)c(=O)c3c(F)ccc(F)c32)cc1]

To a solution of 5,8-difluoro-1-(4-methoxybenzyl)-4-oxo-1,4-dihydroquinoline-3-carboxylic acid (100 mg) obtained in Reference Example 1 in DMF (2 mL) were added (trans)-4-amino-3-hydroxytetrahydropyran (49 mg) prepared according to a document (Journal of Medicinal Chemistry, 2001, 44, 731.), O-(7-azabenzotriazol-1-yl)-N,N,N',N'-tetramethyluronium hexafluorophosphate (165 mg) and triethylamine (0.12 mL), and the mixture was stirred at room temperature for 15 hr. Water (10 mL) was added to the reaction solution, the mixture was stirred, and the precipitated solid was collected by filtration and dried to give the title compound (129 mg).

MS (ESI+): [M+H]+ 445.1

$^1$H NMR (400 MHz, DMSO-d$_6$) δ 1.38-1.58 (1H, m), 1.95-2.12 (1H, m), 3.04-3.16 (2H, m), 3.41-3.49 (1H, m), 3.71 (3H, s), 3.74-3.87 (3H, m), 5.17 (1H, d, J=5.6 Hz), 5.71 (2H, brs), 6.90 (2H, d, J=8.6 Hz), 7.08 (2H, d, J=8.6 Hz), 7.16-7.37 (1H, m), 7.56-7.75 (1H, m), 8.90 (1H, s), 9.85 (1H, d, J=7.1 Hz).

Example 10

5,8-difluoro-N-[(1,2-trans)-2-hydroxycyclohexyl]-1-(4-methoxybenzyl)-4-oxo-1,4-dihydroquinoline-3-carboxamide

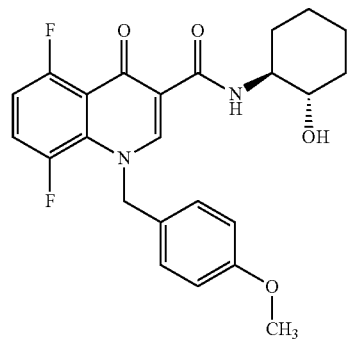 [SMILES: COc1ccc(Cn2cc(C(=O)N[C@H]3CCCC[C@@H]3O)c(=O)c3c(F)ccc(F)c32)cc1]

To a solution of 5,8-difluoro-1-(4-methoxybenzyl)-4-oxo-1,4-dihydroquinoline-3-carboxylic acid (0.15 g) obtained in Reference Example 1 in DMF (4 mL) were added (1,2-trans)-2-hydroxycyclohexylamine hydrochloride (0.10 g), N-[(ethylimino)methylene]-N',N'-dimethylpropane-1,3-diamine hydrochloride (0.13 g), 1-hydroxybenzotriazole (0.10 g) and triethylamine (0.18 mL), and the mixture was stirred at room temperature overnight. The reaction solution and ethyl acetate were combined, and the mixture was stirred. The organic layer was separated, washed with 1 N hydrochloric acid, saturated sodium hydrogen carbonate and brine, dried over anhydrous sodium sulfate and concentrated. The residue was solidified with diisopropyl ether to give the title compound (0.17 g) as a pale-yellow solid.

MS (ESI+): [M+H]+ 443.2

$^1$H NMR (400 MHz, DMSO-d$_6$) δ 1.14-1.37 (4H, m), 1.66 (2H, brs), 1.85 (1H, d, J=2.9 Hz), 2.01 (1H, brs), 3.35-3.44 (1H, m), 3.58-3.68 (1H, m), 3.71 (3H, s), 4.82 (1H, d, J=4.9 Hz), 5.70 (2H, d, J=2.4 Hz), 6.90 (2H, d, J=8.6 Hz), 7.07 (2H, d, J=8.6 Hz), 7.20-7.29 (1H, m), 7.59-7.70 (1H, m), 8.88 (1H, s), 9.79 (1H, d, J=7.6 Hz).

Example 27

5,8-difluoro-N-[(1S,2S)-2-hydroxycyclohexyl]-1-(4-methoxybenzyl)-4-oxo-1,4-dihydroquinoline-3-carboxamide

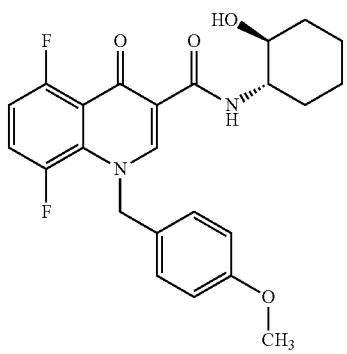 [SMILES: COc1ccc(Cn2cc(C(=O)N[C@H]3CCCC[C@@H]3O)c(=O)c3c(F)ccc(F)c32)cc1]

To a solution of 5,8-difluoro-1-(4-methoxybenzyl)-4-oxo-1,4-dihydroquinoline-3-carboxylic acid (0.30 g) obtained in Reference Example 1 in DMF (10 mL) were added (1S,2S)-2-hydroxycyclohexylamine hydrochloride (0.20 g), N-[(ethylimino)methylene]-N',N'-dimethylpropane-1,3-diamine hydrochloride (0.25 g), 1-hydroxybenzotriazole (0.20 g) and triethylamine (0.36 mL), and the mixture was stirred at room temperature overnight. Water and ethyl acetate were added to the reaction solution, and the mixture was stirred. The organic layer was separated, washed with 1 N hydrochloric acid, saturated sodium hydrogen carbonate and brine, dried over anhydrous sodium sulfate and concentrated. The residue was solidified with diisopropyl ether to give the title compound (0.23 g) as a pale-yellow solid.

MS (ESI+): [M+H]+ 443.1

$^1$H NMR (400 MHz, DMSO-d$_6$) δ 1.14-1.37 (4H, m), 1.54-1.69 (2H, m), 1.80-1.91 (1H, m), 1.96-2.07 (1H, m), 3.36-3.43 (1H, m), 3.58-3.74 (4H, m), 4.82 (1H, d, J=5.1 Hz), 5.70 (2H, d, J=2.4 Hz), 6.90 (2H, d, J=8.8 Hz), 7.07 (2H, d,

J=8.6 Hz), 7.19-7.30 (1H, m), 7.65 (1H, ddd, J=13.9, 9.2, 4.3 Hz), 8.88 (1H, s), 9.79 (1H, d, J=7.3 Hz).

Example 71

1,5-anhydro-2,3-dideoxy-3-({[1-(4-methoxybenzyl)-4-oxo-1,4-dihydrocinnolin-3-yl]carbonyl}amino)-DL-threo-pentitol

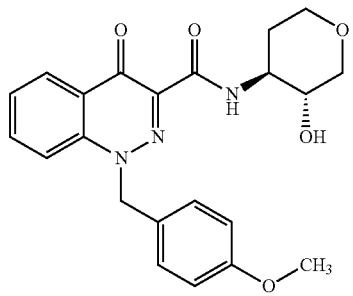 [SMILES: COc1ccc(Cn2nc(C(=O)N[C@H]3CCOC[C@@H]3O)c(=O)c3ccccc32)cc1]

To a solution of 1-(4-methoxybenzyl)-4-oxo-1,4-dihydrocinnoline-3-carboxylic acid (0.10 g) obtained in Reference Example 2 in DMF (2 mL) were added (trans)-4-amino-3-hydroxytetrahydropyran (0.054 g) prepared according to a document (Journal of Medicinal Chemistry, 2001, 44, 731.), O-(7-azabenzotriazol-1-yl)-N,N,N',N'-tetramethyluronium hexafluorophosphate (0.18 g) and triethylamine (0.14 mL), and the mixture was stirred at room temperature for 15 hr. The reaction mixture was diluted with ethyl acetate and washed with saturated brine, and the organic layer was dried over anhydrous sodium sulfate and concentrated. The residue was purified by silica gel column chromatography (hexane-ethyl acetate) to give the title compound (0.076 g).

MS (ESI+): [M+H]$^+$ 410.1

$^1$H NMR (400 MHz, DMSO-d$_6$) δ 1.52 (1H, brs), 2.09 (1H, brs), 3.12 (1H, t, J=10.1 Hz), 3.36-3.55 (2H, m), 3.70 (3H, s), 3.74-3.95 (3H, m), 5.16 (1H, d, J=5.6 Hz), 5.83 (2H, s), 6.90 (2H, d, J=8.8 Hz), 7.28 (2H, d, J=8.8 Hz), 7.54-7.67 (1H, m), 7.82-7.93 (1H, m), 7.93-8.02 (1H, m), 8.28 (1H, d, J=8.1 Hz), 9.82 (1H, d, J=7.3 HZ).

Example 73

1-(4-carbamoylbenzyl)-4-oxo-1,4-dihydrocinnoline-3-carboxamide

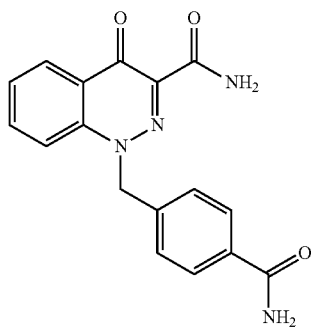 [SMILES: NC(=O)c1ccc(Cn2nc(C(N)=O)c(=O)c3ccccc32)cc1]

To a solution of 1-(4-carbamoylbenzyl)-4-oxo-1,4-dihydrocinnoline-3-carboxylic acid (0.15 g) obtained in Reference Example 4 in DMF (10 mL) were added N-[(ethylimino)methylene]-N',N'-dimethylpropane-1,3-diamine hydrochloride (0.13 g), 1-hydroxybenzotriazole ammonium salt (0.11 g) and triethylamine (0.19 mL), and the mixture was stirred at room temperature overnight. A saturated aqueous sodium hydrogen carbonate solution was added to the reaction solution, and the mixture was extracted with ethyl acetate, washed with brine, dried over anhydrous sodium sulfate and concentrated. The residue was solidified with diisopropyl ether to give the title compound (0.12 g) as a colorless solid.

MS (ESI+): [M+H]$^+$ 323.1

$^1$H NMR (300 MHz, DMSO-d$_6$) δ 5.92 (2H, s), 7.36 (3H, d, J=8.0 Hz), 7.53-7.65 (1H, m), 7.77-7.99 (6H, m), 8.28 (1H, d, J=8.0 Hz), 8.87 (1H, d, J=2.3 Hz).

Example 74

1-(4-carbamoylbenzyl)-N-[(1,2-trans)-2-hydroxycyclohexyl]-4-oxo-1,4-dihydroquinoline-3-carboxamide

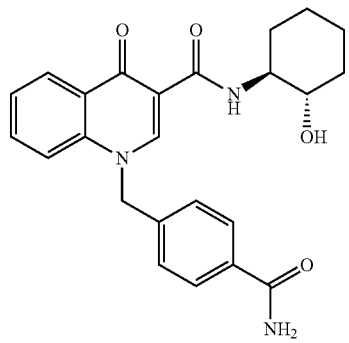 [SMILES: NC(=O)c1ccc(Cn2cc(C(=O)N[C@H]3CCCC[C@@H]3O)c(=O)c3ccccc32)cc1]

To a solution of 1-(4-carbamoylbenzyl)-4-oxo-1,4-dihydroquinoline-3-carboxylic acid (0.15 g) obtained in Reference Example 3 in DMF (10 mL) were added (1,2-trans)-2-hydroxycyclohexylamine hydrochloride (0.08 g), O-(7-azabenzotriazol-1-yl)-N,N,N',N'-tetramethyluronium hexafluorophosphate (0.27 g) and triethylamine (0.19 mL), and the mixture was stirred at room temperature overnight. Water was added to the reaction mixture, and the precipitate was collected by filtration and dried. The precipitate was washed with diisopropyl ether to give the title compound (0.12 g) as a colorless solid.

MS (ESI+): [M+H]$^+$ 420.2

$^1$H NMR (300 MHz, DMSO-d$_6$) δ 1.30 (4H, d, J=8.3 Hz), 1.55-1.71 (2H, m), 1.87 (1H, d, J=8.3 Hz), 2.03 (1H, d, J=10.6 Hz), 3.34-3.46 (1H, m), 3.71 (1H, d, J=8.7 Hz), 4.81 (1H, d, J=4.9 Hz), 5.85 (2H, s), 7.28 (2H, d, J=8.3 Hz), 7.34 (1H, brs), 7.50 (1H, t, J=7.2 Hz), 7.65-7.77 (2H, m), 7.82 (2H, d, J=8.3 Hz), 7.92 (1H, brs), 8.36 (1H, d, J=7.6 Hz), 9.09 (1H, s), 10.08 (1H, d, J=7.6 Hz).

Example 75

1-(4-carbamoylbenzyl)-N-[(1,2-trans)-2-hydroxycyclohexyl]-4-oxo-1,4-dihydrocinnoline-3-carboxamide

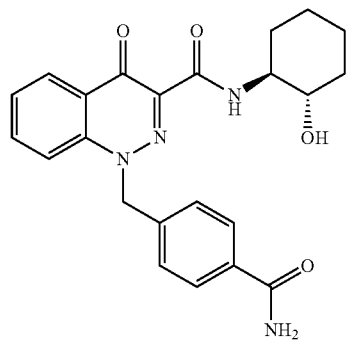 [SMILES: NC(=O)c1ccc(Cn2nc(C(=O)N[C@H]3CCCC[C@@H]3O)c(=O)c3ccccc32)cc1]

To a solution of 1-(4-carbamoylbenzyl)-4-oxo-1,4-dihydrocinnoline-3-carboxylic acid (0.15 g) obtained in Reference Example 4 in DMF (10 mL) were added (1,2-trans)-2-hydroxycyclohexylamine hydrochloride (0.08 g), O-(7-azabenzotriazol-1-yl)-N,N,N',N'-tetramethyluronium hexafluorophosphate (0.26 g) and triethylamine (0.19 mL), and the mixture was stirred at room temperature overnight. Water was added to the reaction mixture, and the precipitate was collected by filtration and dried. The precipitate was washed with diisopropyl ether to give the title compound (0.13 g) as a colorless solid.

MS (ESI+): [M+H]⁺ 421.2

¹H NMR (300 MHz, DMSO-d₆) δ 1.16-1.41 (4H, m), 1.55-1.71 (2H, m), 1.82-1.93 (1H, m), 1.98-2.09 (1H, m), 3.35-3.47 (1H, m), 3.63-3.76 (1H, m), 4.79 (1H, d, J=5.3 Hz), 5.96 (2H, s), 7.35 (3H, d, J=8.0 Hz), 7.57-7.64 (1H, m), 7.78-7.89 (4H, m), 7.93 (1H, brs), 8.29 (1H, d, J=8.0 Hz), 9.74 (1H, d, J=7.6 Hz).

Example 78

1-(4-carbamoylbenzyl)-N-[(1S,2S)-2-hydroxycyclohexyl]-4-oxo-1,4-dihydroquinoline-3-carboxamide

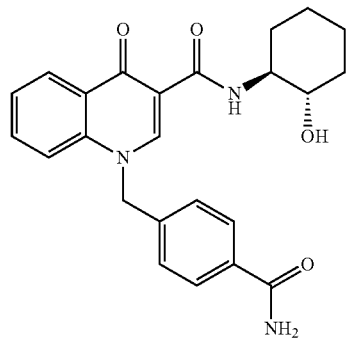 [SMILES: NC(=O)c1ccc(Cn2cc(C(=O)N[C@H]3CCCC[C@@H]3O)c(=O)c3ccccc32)cc1]

To a solution of 1-(4-carbamoylbenzyl)-4-oxo-1,4-dihydroquinoline-3-carboxylic acid (0.20 g) obtained in Reference Example 3 in DMF (5 mL) were added (1S,2S)-2-hydroxycyclohexylamine hydrochloride (0.09 g), O-(7-azabenzotriazol-1-yl)-N,N,N',N'-tetramethyluronium hexafluorophosphate (0.35 g) and triethylamine (0.26 mL), and the mixture was stirred at room temperature overnight. Water was added to the reaction mixture, and the precipitate was collected by filtration and dried. The precipitate was recrystallized from ethanol-water (10:1) to give the title compound (0.16 g) as a colorless solid.

MS (ESI+): [M+H]⁺ 420.3

¹H NMR (400 MHz, DMSO-d₆) δ 1.15-1.39 (4H, m), 1.55-1.71 (2H, m), 1.81-1.92 (1H, m), 2.05 (1H, brs), 3.40 (1H, brs), 3.69 (1H, brs), 4.83 (1H, d, J=4.6 Hz), 5.85 (2H, s), 7.28 (2H, d, J=7.6 Hz), 7.37 (1H, brs), 7.50 (1H, t, J=7.3 Hz), 7.66-7.76 (2H, m), 7.82 (2H, d, J=7.6 Hz), 7.94 (1H, brs), 8.36 (1H, d, J=7.8 Hz), 9.09 (1H, s), 10.09 (1H, d, J=7.3 Hz).

Example 80

8-fluoro-N-[(1,2-trans)-2-hydroxycyclohexyl]-4-oxo-1-[4-(1H-pyrazol-1-yl)benzyl]-1,4-dihydroquinoline-3-carboxamide

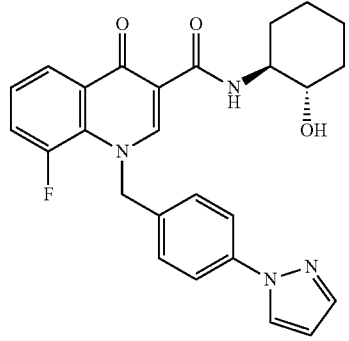 [SMILES: O=C(N[C@H]1CCCC[C@@H]1O)c1cn(Cc2ccc(-n3cccn3)cc2)c2c(F)cccc2c1=O]

To a solution of 1-[4-(1H-pyrazol-1-yl)benzyl]-8-fluoro-4-oxo-1,4-dihydroquinoline-3-carboxylic acid (0.12 g) obtained by referring to a document (Bioorganic and Medicinal Chemistry Letters, 2010, 20, 1334) in DMF (5 mL) were added (1,2-trans)-2-hydroxycyclohexylamine hydrochloride (0.05 g), O-(7-azabenzotriazol-1-yl)-N,N,N',N'-tetramethyluronium hexafluorophosphate (0.18 g) and triethylamine (0.13 mL), and the mixture was stirred at room temperature overnight. Water was added to the reaction mixture, and the precipitate was collected by filtration and dried. This precipitate was recrystallized from ethanol-water (10:1) to give the title compound (0.13 g) as a colorless solid.

MS (ESI+): [M+H]⁺ 461.3

¹H NMR (400 MHz, DMSO-d₆) δ 1.15-1.39 (4H, m), 1.55-1.70 (2H, m), 1.87 (1H, d, J=9.5 Hz), 2.03 (1H, d, J=11.2 Hz), 3.37-3.45 (1H, m), 3.69 (1H, d, J=8.3 Hz), 4.83 (1H, d, J=5.1 Hz), 5.86 (2H, brs), 6.52 (1H, s), 7.24 (2H, d, J=8.3 Hz), 7.51 (1H, td, J=7.9, 4.4 Hz), 7.64 (1H, dd, J=14.5, 7.9 Hz), 7.72 (1H, s), 7.80 (2H, d, J=8.3 Hz), 8.22 (1H, d, J=8.1 Hz), 8.44 (1H, d, J=2.2 Hz), 9.01 (1H, s), 9.93 (1H, d, J=7.6 Hz).

Example 84

N-[(1,2-trans)-5,5-difluoro-2-hydroxycyclohexyl]-5,8-difluoro-1-(4-methoxybenzyl)-4-oxo-1,4-dihydroquinoline-3-carboxamide

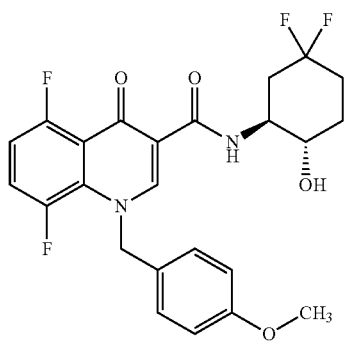 [SMILES: COc1ccc(Cn2cc(C(=O)N[C@H]3CC(F)(F)CC[C@@H]3O)c(=O)c3c(F)ccc(F)c32)cc1]

To a solution of 5,8-difluoro-1-(4-methoxybenzyl)-4-oxo-1,4-dihydroquinoline-3-carboxylic acid (0.30 g) obtained in Reference Example 1 in DMF (2 mL) were added (1,2-trans)-2-amino-4,4-difluorocyclohexanol hydrochloride (0.08 g) obtained in Reference Example 13, N-[(ethylimino)methylene]-N',N'-dimethylpropane-1,3-diamine hydrochloride (0.08 g), 1-hydroxybenzotriazole (0.06 g) and triethylamine (0.08 mL), and the mixture was stirred at room temperature for 4 hr. The reaction solution was diluted with ethyl acetate, washed with water and brine, dried over anhydrous sodium sulfate and concentrated. The residue was solidified with diisopropyl ether-ethyl acetate to give the title compound (0.09 g) as a white solid.

MS (ESI+): [M+H]$^+$ 479.3

$^1$H NMR (400 MHz, DMSO-d$_6$) δ 1.58 (1H, brs), 1.77-2.20 (4H, m), 2.30-2.41 (1H, m), 3.54-3.81 (4H, m), 4.02 (1H, brs), 5.15 (1H, brs), 5.70 (2H, brs), 6.90 (2H, d, J=7.8 Hz), 7.08 (2H, d, J=7.8 Hz), 7.25 (1H, t, J=9.8 Hz), 7.66 (1H, brs), 8.88 (1H, s), 9.93 (1H, d, J=7.1 Hz).

Example 85

N-[(1,2-trans)-2-hydroxycyclohexyl]-4-oxo-1-[4-(1H-pyrazol-5-yl)benzyl]-1,4-dihydroquinoline-3-carboxamide

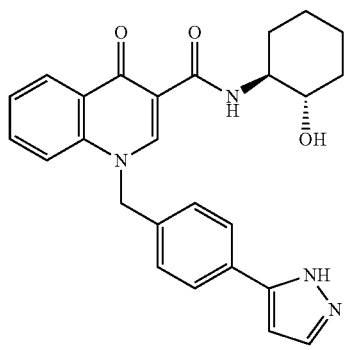 [SMILES: O=C(N[C@H]1CCCC[C@@H]1O)c1cn(Cc2ccc(-c3ccn[nH]3)cc2)c2ccccc2c1=O]

To a solution (10 mL) of 4-oxo-1-{4-[1-(tetrahydro-2H-pyran-2-yl)-1H-pyrazol-5-yl]benzyl}-1,4-dihydroquinoline-3-carboxylic acid (0.10 g) obtained in Reference Example 15 in DMF were added (1,2-trans)-2-hydroxycyclohexylamine hydrochloride (0.04 g), O-(7-azabenzotriazol-1-yl)-N,N,N',N'-tetramethyluronium hexafluorophosphate (0.13 g) and triethylamine (0.1 mL), and the mixture was stirred at room temperature overnight. Water was added to the reaction mixture, and the precipitate was collected by filtration and dissolved in ethyl acetate (2 mL). 4 N Hydrogen chloride-ethyl acetate solution (2 mL) was added, and the mixture was stirred for 2 hr. The reaction mixture was diluted with ethyl acetate, washed with saturated sodium hydrogen carbonate and saturated brine, dried over anhydrous sodium sulfate, and concentrated. The residue was purified by silica gel column chromatography (hexane-ethyl acetate) to give the title compound (0.016 g) as a pale-yellow solid.

MS (ESI+): [M+H]$^+$ 443.3

$^1$H NMR (400 MHz, DMSO-d$_6$) δ 1.17-1.38 (4H, m), 1.56-1.70 (2H, m), 1.87 (1H, d, J=10.0 Hz), 2.03 (1H, d, J=12.5 Hz), 3.37-3.47 (1H, m), 3.66-3.74 (1H, m), 4.83 (1H, d, J=4.9 Hz), 5.80 (2H, s), 6.66 (1H, d, J=2.0 Hz), 7.27 (2H, d, J=8.1 Hz), 7.51 (1H, t, J=7.8 Hz), 7.69-7.81 (5H, m), 8.36 (1H, d, J=7.8 Hz), 9.10 (1H, s), 10.10 (1H, d, J=7.6 Hz), 12.88 (1H, brs).

Example 88

1-(4-carbamoylbenzyl)-N-[(1,2-trans)-2-fluorocyclohexyl]-4-oxo-1,4-dihydroquinoline-3-carboxamide

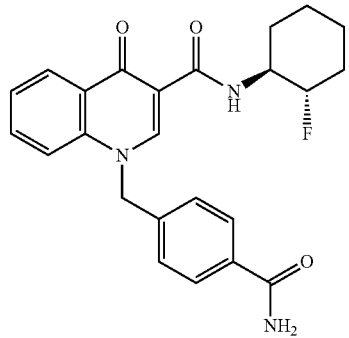 [SMILES: NC(=O)c1ccc(Cn2cc(C(=O)N[C@H]3CCCC[C@@H]3F)c(=O)c3ccccc32)cc1]

To a solution (5 mL) of 1-(4-carbamoylbenzyl)-4-oxo-1,4-dihydroquinoline-3-carboxylic acid (0.1 g) obtained in Reference Example 3, (trans)-2-fluorocyclohexylamine hydrobromide (0.068 g) prepared according to a known method (Coburn et al., WO 2007/011833) and triethylamine (0.13 mL) in DMF was added O-(7-azabenzotriazol-1-yl)-N,N,N',N'-tetramethyluronium hexafluorophosphate (0.18 g), and the mixture was stirred at room temperature overnight. Water was added to the reaction mixture, and the precipitate was collected by filtration and dried to give the title compound (0.11 g) as a colorless solid.

MS (ESI+): [M+H]$^+$ 422.1

$^1$H NMR (400 MHz, DMSO-d$_6$) δ 1.30-1.46 (3H, m), 1.49-1.77 (3H, m), 1.91-2.12 (2H, m), 3.99-4.12 (1H, m), 4.45-4.66 (1H, m), 5.85 (2H, s), 7.29 (2H, d, J=8.1 Hz), 7.36 (1H, brs), 7.51 (1H, t, J=7.3 Hz), 7.66-7.77 (2H, m), 7.82 (2H, d, J=8.3 Hz), 7.94 (1H, brs), 8.36 (1H, d, J=7.1 Hz), 9.11 (1H, s), 10.20 (1H, d, J=8.3 Hz).

Example 92

8-fluoro-N-[(1,2-trans)-2-hydroxycyclopentyl]-4-oxo-1-[4-(1H-pyrazol-1-yl)benzyl]-1,4-dihydroquinoline-3-carboxamide

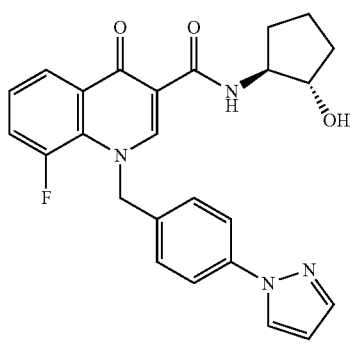 [SMILES: O=C(N[C@H]1CCC[C@@H]1O)c1cn(Cc2ccc(-n3cccn3)cc2)c2c(F)cccc2c1=O]

To a solution (5 mL) of 1-[4-(1H-pyrazol-1-yl)benzyl]-8-fluoro-4-oxo-1,4-dihydroquinoline-3-carboxylic acid (0.1 g) prepared by referring to a document (Bioorganic and Medicinal Chemistry Letters, 2010, 20, 1334), (trans)-2-aminocyclopentanol hydrochloride (0.057 g) and triethylamine (0.12 mL) in DMF was added O-(7-azabenzotriazol-1-yl)-N,N,N',N'-tetramethyluronium hexafluorophosphate (0.16 g), and the mixture was stirred at room temperature overnight. Water was added to the reaction mixture, and the precipitate was collected by filtration and dried to give the title compound (0.11 g) as a pale-yellow solid.

MS (ESI+): [M+H]$^+$ 447.2

$^1$H NMR (300 MHz, DMSO-d$_6$) δ 1.38-1.95 (5H, m), 2.02-2.18 (1H, m), 3.88-4.10 (2H, m), 5.86 (2H, d, J=2.8 Hz), 6.47-6.56 (1H, m), 7.25 (2H, d, J=8.5 Hz), 7.51 (1H, td, J=8.0, 4.4 Hz), 7.59-7.69 (1H, m), 7.72 (1H, d, J=1.7 Hz), 7.79 (2H, d, J=8.5 Hz), 8.21 (1H, d, J=7.9 Hz), 8.44 (1H, d, J=2.5 Hz), 9.02 (1H, s), 9.89 (1H, d, J=7.2 Hz).

Example 93

N-[(1,2-trans)-2-hydroxycyclopentyl]-1-[4-(2-methylpyridin-4-yl)benzyl]-4-oxo-1,4-dihydroquinoline-3-carboxamide

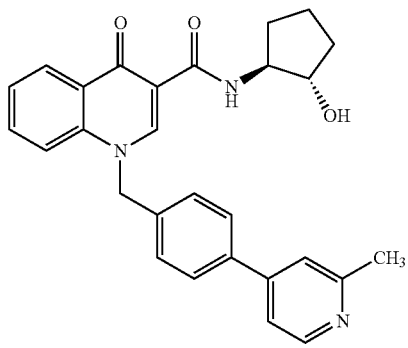 [SMILES: Cc1cc(-c2ccc(Cn3cc(C(=O)N[C@H]4CCC[C@@H]4O)c(=O)c4ccccc43)cc2)ccn1]

To a solution (4 mL) of 1-(4-bromobenzyl)-N-[(1,2-trans)-2-hydroxycyclopentyl]-4-oxo-1,4-dihydroquinoline-3-carboxamide (0.1 g) obtained in Reference Example 16 and 2-methyl-4-(4,4,5,5-tetramethyl-1,3,2-dioxaborolan-2-yl)pyridine (0.075 g) in DME were added 2 M aqueous sodium carbonate solution (1 mL) and [1,1-bis(diphenylphosphino)ferrocene]dichloropalladium(II) dichloromethane adduct (0.01 g), and the mixture was stirred at 100° C. for 1 hr under microwave irradiation. The reaction mixture was diluted with ethyl acetate, and the insoluble material was filtered off. The filtrate was washed with saturated brine, dried over anhydrous sodium sulfate and concentrated. The residue was purified by silica gel chromatography (hexane-ethyl acetate-methanol) to give the title compound (0.036 g) as a pale-yellow solid.

MS (ESI+): [M+H]$^+$ 454.4

$^1$H NMR (300 MHz, DMSO-d$_6$) δ 1.37-1.95 (5H, m), 2.02-2.18 (1H, m), 2.45 (3H, s), 3.89-4.11 (2H, m), 4.94 (1H, d, J=3.4 Hz), 5.86 (2H, s), 7.36 (2H, d, J=8.1 Hz), 7.41-7.57 (3H, m), 7.70-7.82 (4H, m), 8.36 (1H, d, J=7.7 Hz), 8.47 (1H, d, J=5.1 Hz), 9.13 (1H, s), 10.05 (1H, d, J=7.2 Hz).

Example 94

1-[4-(1,3-dimethyl-1H-pyrazol-4-yl)benzyl]-N-[(1,2-trans)-2-hydroxycyclopentyl]-4-oxo-1,4-dihydroquinoline-3-carboxamide

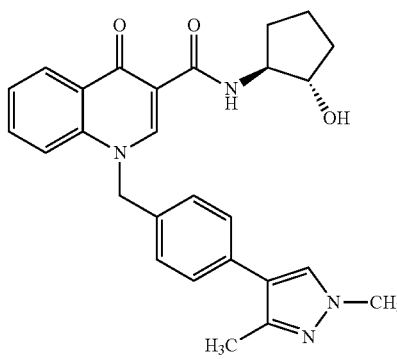

To a solution (4 mL) of 1-(4-bromobenzyl)-N-[(1,2-trans)-2-hydroxycyclopentyl]-4-oxo-1,4-dihydroquinoline-3-carboxamide (0.1 g) obtained in Reference Example 16 and 1,3-dimethyl-4-(4,4,5,5-tetramethyl-1,3,2-dioxaborolan-2-yl)-1H-pyrazole (0.075 g) in DME were added 2 M aqueous sodium carbonate solution (1 mL) and [1,1-bis(diphenylphosphino)ferrocene]dichloropalladium(II) dichloromethane adduct (0.01 g), and the mixture was stirred at 100° C. for 1 hr under microwave irradiation. The reaction mixture was diluted with ethyl acetate, and the insoluble material was filtered off. The filtrate was washed with saturated aqueous sodium hydrogen carbonate solution and saturated brine, dried over anhydrous sodium sulfate, and concentrated. The residue was purified by silica gel chromatography (hexane-ethyl acetate-methanol) to give the title compound (0.035 g) as a pale-yellow solid.

MS (ESI+): [M+H]$^+$ 457.4

$^1$H NMR (300 MHz, DMSO-d$_6$) δ 1.37-1.96 (5H, m), 2.02-2.17 (1H, m), 2.24 (3H, s), 3.75 (3H, s), 3.89-4.10 (2H, m), 5.78 (2H, s), 7.24 (2H, d, J=8.3 Hz), 7.39 (2H, d, J=8.3 Hz), 7.47-7.56 (1H, m), 7.71-7.86 (3H, m), 8.35 (1H, dd, J=8.0, 1.2 Hz), 9.09 (1H, s), 10.05 (1H, d, J=7.4 Hz).

All Example compounds are shown in the following Tables. The compounds of Examples 7 to 9, 11 to 26, 28 to 70, 72, 76, 77, 79, 81, 82, 83, 86, 87 and 89 to 91 were produced by using commercially available reagents or the compounds obtained in Reference Examples and according to the above-mentioned methods or a method analogous thereto. MS in the Table shows the actually measured values.

TABLE 1

| Ex. No. | compound name | structure | stereo-chemistry | MS (M + H)+ |
|---|---|---|---|---|
| 1 | 5,8-difluoro-1-(4-methoxybenzyl)-4-oxo-1,4-dihydroquinoline-3-carboxamide | 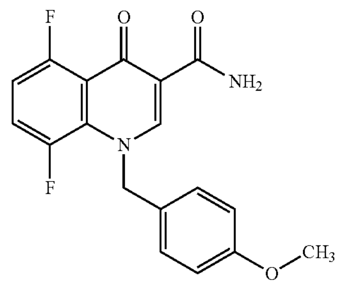 [SMILES: COc1ccc(Cn2cc(C(N)=O)c(=O)c3c(F)ccc(F)c32)cc1] | | 345.2 |
| 2 | 5,8-difluoro-1-(4-methoxybenzyl)-4-oxo-N-phenyl-1,4-dihydroquinoline-3-carboxamide | 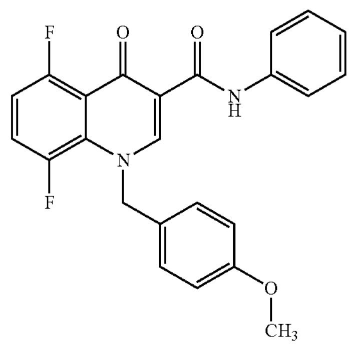 [SMILES: COc1ccc(Cn2cc(C(=O)Nc3ccccc3)c(=O)c3c(F)ccc(F)c32)cc1] | | 421.1 |
| 3 | 5,8-difluoro-N-[(1,2-trans)-2-hydroxycyclohexyl]-4-oxo-1-[4-(1H-pyrazol-1-yl)benzyl]-1,4-dihydroquinoline-3-carboxamide | 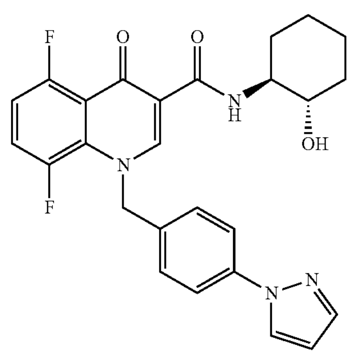 [SMILES: O=C(N[C@H]1CCCC[C@@H]1O)c1cn(Cc2ccc(-n3cccn3)cc2)c2c(F)ccc(F)c2c1=O] | 1,2-trans racemate | 479.3 |
| 4 | N-[(1,2-trans)-2-hydroxycyclohexyl]-4-oxo-1-[4-(1H-pyrazol-1-yl)benzyl]-1,4-dihydrocinnoline-3-carboxamide | 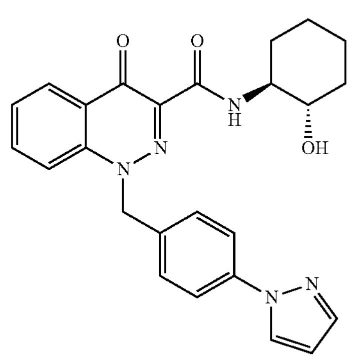 [SMILES: O=C(N[C@H]1CCCC[C@@H]1O)c1nn(Cc2ccc(-n3cccn3)cc2)c2ccccc2c1=O] | 1,2-trans racemate | 444.2 |

TABLE 1-continued

| Ex. No. | compound name | structure | stereo-chemistry | MS (M + H)+ |
|---|---|---|---|---|
| 5 | 1-(4-carbamoylbenzyl)-N-[(1S,2S)-2-hydroxycyclohexyl]-4-oxo-1,4-dihydroquinoline-3-carboxamide | 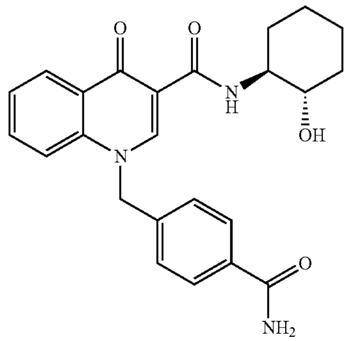 | 1S,2S | 420.3 |
| 6 | 1,5-anhydro-2,3-dideoxy-3-({[5,8-difluoro-1-(4-methoxybenzyl)-4-oxo-1,4-dihydroquinolin-3-yl]carbonyl}amino)-DL-threo-pentitol | 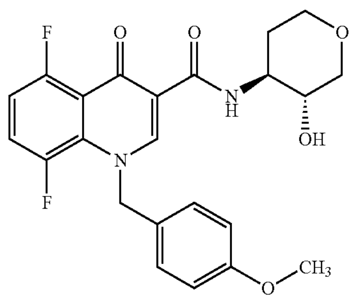 [SMILES: COc1ccc(Cn2cc(C(=O)N[C@H]3CCOC[C@@H]3O)c(=O)c3c(F)ccc(F)c32)cc1] | racemate | 445.1 |
| 7 | 5,8-difluoro-1-(4-methoxybenzyl)-N-methyl-4-oxo-1,4-dihydroquinoline-3-carboxamide | 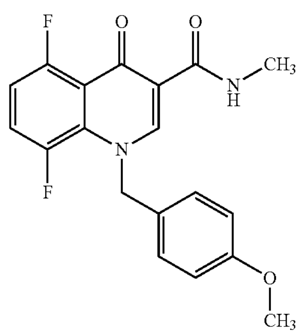 [SMILES: CNC(=O)c1cn(Cc2ccc(OC)cc2)c2c(F)ccc(F)c2c1=O] | | 359.1 |

1H NMR (400 MHz, DMSO-d6) δ 2.85 (3H, d, J = 4.9 Hz), 3.71 (3H, s), 5.69 (2H, d, J = 2.9 Hz), 6.89 (2H, d, J = 8.6 Hz), 7.08 (2H, d, J = 8.6 Hz), 7.18-7.28 (1H, m), 7.59-7.69 (1H, m), 8.89 (1H, s), 9.55 (1H, d, J = 4.6 Hz).

| 8 | N-cyclopropyl-5,8-difluoro-1-(4-methoxybenzyl)-4-oxo-1,4-dihydroquinoline-3-carboxamide | | | 385.1 |

TABLE 1-continued

| Ex. No. | compound name | structure | stereo-chemistry | MS (M + H)+ |
|---|---|---|---|---|
| 9 | 5,8-difluoro-1-(4-methoxybenzyl)-N-(1-methylethyl)-4-oxo-1,4-dihydroquinoline-3-carboxamide | 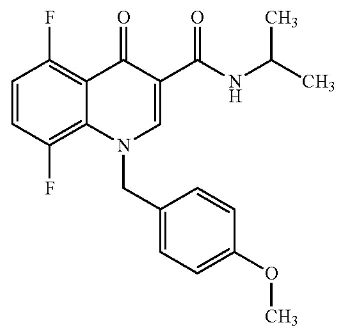 [SMILES: COc1ccc(Cn2cc(C(=O)NC(C)C)c(=O)c3c(F)ccc(F)c32)cc1] | | 387.2 |
| 10 | 5,8-difluoro-N-[(1,2-trans)-2-hydroxycyclohexyl]-1-(4-methoxybenzyl)-4-oxo-1,4-dihydroquinoline-3-carboxamide | 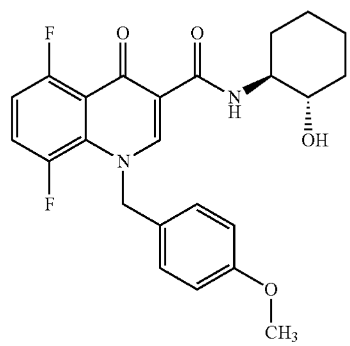 [SMILES: COc1ccc(Cn2cc(C(=O)N[C@H]3CCCC[C@@H]3O)c(=O)c3c(F)ccc(F)c32)cc1] | 1,2-trans racemate | 443.2 |
| 11 | 5,8-difluoro-N-[(1,2-cis)-2-hydroxycyclohexyl]-1-(4-methoxybenzyl)-4-oxo-1,4-dihydroquinoline-3-carboxamide | 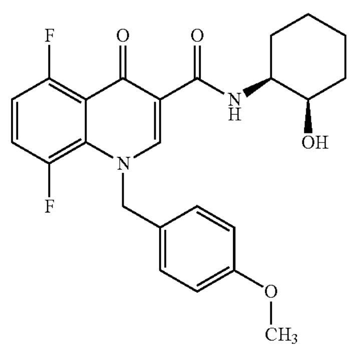 [SMILES: COc1ccc(Cn2cc(C(=O)N[C@H]3CCCC[C@H]3O)c(=O)c3c(F)ccc(F)c32)cc1] | 1,2-cis racemate | 443.2 |
| 12 | 5,8-difluoro-1-(4-methoxybenzyl)-N,N-dimethyl-4-oxo-1,4-dihydroquinoline-3-carboxamide | 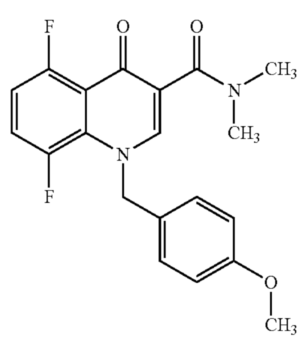 [SMILES: COc1ccc(Cn2cc(C(=O)N(C)C)c(=O)c3c(F)ccc(F)c32)cc1] | | 373.2 |

TABLE 1-continued

| Ex. No. | compound name | structure | stereo-chemistry | MS (M + H)+ |
|---|---|---|---|---|
| 13 | 1-(4-methoxybenzyl)-4-oxo-1,4-dihydroquinoline-3-carbohydrazide | | | 324.0 |

1H NMR (400 MHz, DMSO-d6) δ 3.70 (3H, s), 4.61 (2H, d, J = 4.4 Hz), 5.71 (2H, s), 6.91 (2H, d, J = 8.6 Hz), 7.21 (2H, d, J = 8.6 Hz), 7.50 (1H, t, J = 7.5 Hz), 7.71-7.79 (1H, m), 7.79-7.86 (1H, m), 8.34 (1H, d, J = 7.6 Hz), 9.07 (1H, s), 10.60-10.73 (1H, m).

| Ex. No. | compound name | structure | stereo-chemistry | MS (M + H)+ |
|---|---|---|---|---|
| 14 | N-cyclohexyl-5,8-difluoro-1-(4-methoxybenzyl)-4-oxo-1,4-dihydroquinoline-3-carboxamide | 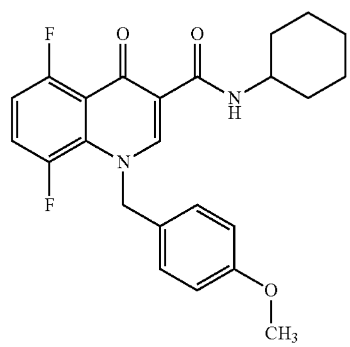 [SMILES: COc1ccc(Cn2cc(C(=O)NC3CCCCC3)c(=O)c3c(F)ccc(F)c32)cc1] | | 427.2 |
| 15 | 5,8-difluoro-N-[(1,4-trans)-4-hydroxycyclohexyl]-1-(4-methoxybenzyl)-4-oxo-1,4-dihydroquinoline-3-carboxamide | 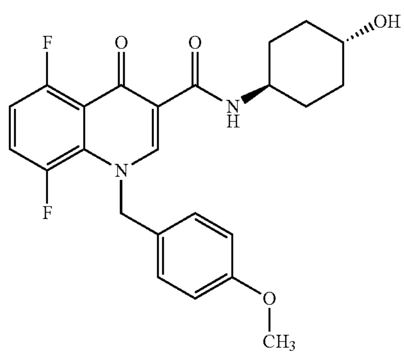 [SMILES: COc1ccc(Cn2cc(C(=O)N[C@H]3CC[C@H](O)CC3)c(=O)c3c(F)ccc(F)c32)cc1] | 1,4-trans | 443.2 |
| 16 | 5,8-difluoro-N-(3-hydroxycyclohexyl)-1-(4-methoxybenzyl)-4-oxo-1,4-dihydroquinoline-3-carboxamide | 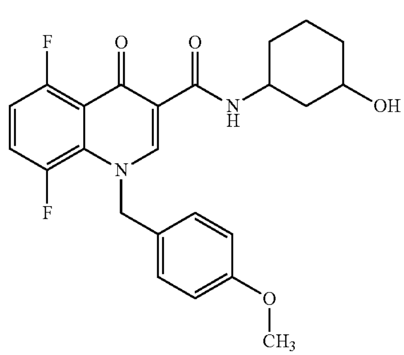 [SMILES: COc1ccc(Cn2cc(C(=O)NC3CCCC(O)C3)c(=O)c3c(F)ccc(F)c32)cc1] | racemate, diastereo-mixture | 443.2 |

TABLE 1-continued

| Ex. No. | compound name | structure | stereo-chemistry | MS (M + H)+ |
|---|---|---|---|---|
| 17 | 5,8-difluoro-N-(2-hydroxyethyl)-1-(4-methoxybenzyl)-4-oxo-1,4-dihydroquinoline-3-carboxamide | 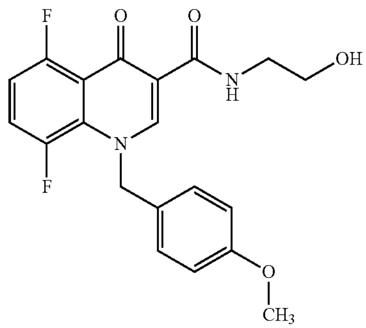 [SMILES: COc1ccc(Cn2cc(C(=O)NCCO)c(=O)c3c(F)ccc(F)c32)cc1] | | 389.2 |
| 18 | 5,8-difluoro-3-[(3-hydroxypiperidin-1-yl)carbonyl]-1-(4-methoxybenzyl)-quinolin-4(1H)-one | 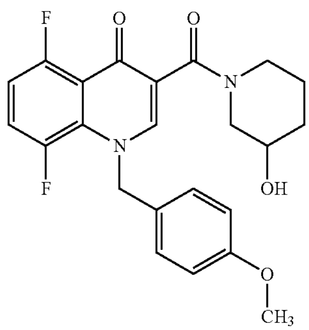 [SMILES: COc1ccc(Cn2cc(C(=O)N3CCCC(O)C3)c(=O)c3c(F)ccc(F)c32)cc1] | racemate | 429.1 |
| 19 | 5,8-difluoro-1-(4-methoxybenzyl)-3-(piperidin-1-ylcarbonyl)quinolin-4(1H)-one | 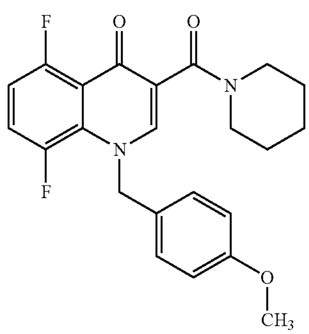 [SMILES: COc1ccc(Cn2cc(C(=O)N3CCCCC3)c(=O)c3c(F)ccc(F)c32)cc1] | | 413.1 |
| 20 | 5,8-difluoro-1-(4-methoxybenzyl)-N-(2-methoxyethyl)-4-oxo-1,4-dihydroquinoline-3-carboxamide | 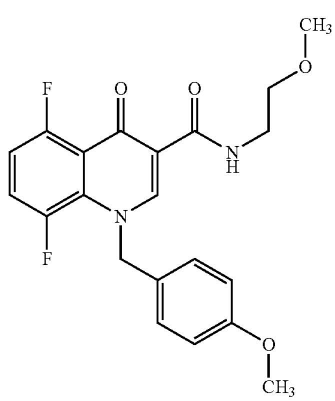 [SMILES: COCCNC(=O)c1cn(Cc2ccc(OC)cc2)c2c(F)ccc(F)c2c1=O] | | 403.1 |

1H NMR (400 MHz, DMSO-d6) δ 3.30 (3H, s), 3.44-3.54 (4H, m), 3.71 (3H, s), 5.69 (2H, d, J = 2.9 Hz), 6.89 (2H, d, J = 8.6 Hz), 7.08 (2H, d, J = 8.6 Hz), 7.20-7.32 (1H, m), 7.59-7.73 (1H, m), 8.89 (1H, s), 9.77-9.84 (1H, m).

TABLE 1-continued

| Ex. No. | compound name | structure | stereo-chemistry | MS (M + H)+ |
|---|---|---|---|---|
| 21 | 5,8-difluoro-1-(4-methoxybenzyl)-4-oxo-N-piperidin-1-yl-1,4-dihydroquinoline-3-carboxamide | 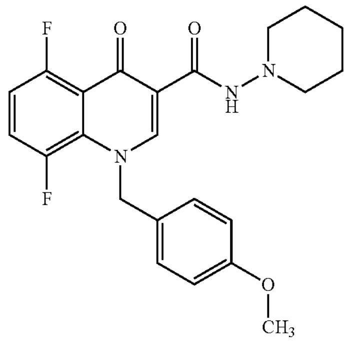 | | 428.1 |
| 22 | 5,8-difluoro-N-(2-hydroxy-2-phenylethyl)-1-(4-methoxybenzyl)-4-oxo-1,4-dihydroquinoline-3-carboxamide | 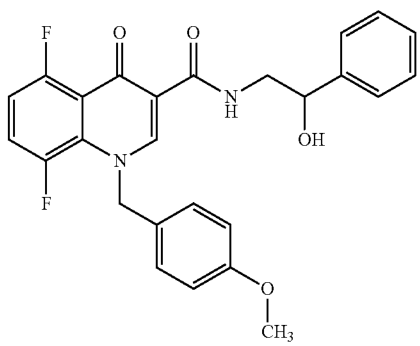 [SMILES: COc1ccc(Cn2cc(C(=O)NCC(O)c3ccccc3)c(=O)c3c(F)ccc(F)c32)cc1] | racemate | 465.0 |
| 23 | 5,8-difluoro-1-(4-methoxybenzyl)-4-oxo-N-(tetrahydrofuran-2-ylmethyl)-1,4-dihydroquinoline-3-carboxamide | 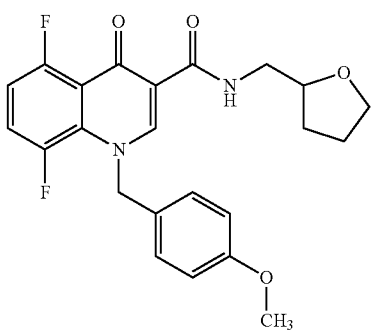 [SMILES: COc1ccc(Cn2cc(C(=O)NCC3CCCO3)c(=O)c3c(F)ccc(F)c32)cc1] | racemate | 429.1 |
| 24 | 5,8-difluoro-N,N-bis(2-hydroxyethyl)-1-(4-methoxybenzyl)-4-oxo-1,4-dihydroquinoline-3-carboxamide | 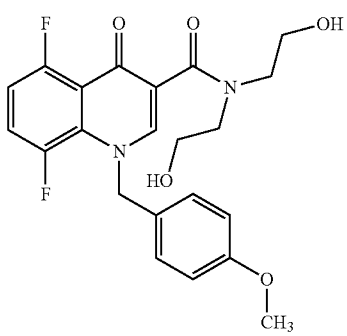 [SMILES: COc1ccc(Cn2cc(C(=O)N(CCO)CCO)c(=O)c3c(F)ccc(F)c32)cc1] | | 433.1 |

TABLE 1-continued

| Ex. No. | compound name | structure | stereo-chemistry | MS (M + H)+ |
|---|---|---|---|---|
| 25 | 5,8-difluoro-N-[(1,2-trans)-2-hydroxycyclopentyl]-1-(4-methoxybenzyl)-4-oxo-1,4-dihydroquinoline-3-carboxamide | 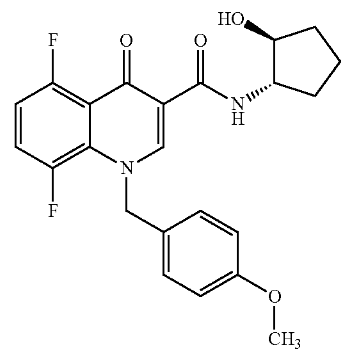 [SMILES: COc1ccc(Cn2cc(C(=O)N[C@H]3CCC[C@@H]3O)c(=O)c3c(F)ccc(F)c32)cc1] | 1,2-trans racemate | 429.1 |
| 26 | N-(2,3-dihydroxypropyl)-5,8-difluoro-1-(4-methoxybenzyl)-4-oxo-1,4-dihydroquinoline-3-carboxamide | 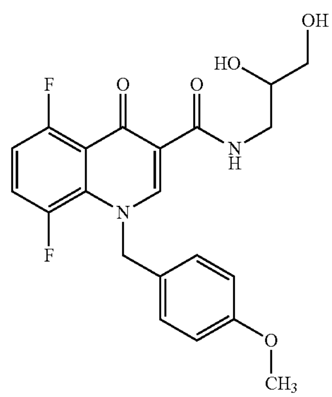 [SMILES: COc1ccc(Cn2cc(C(=O)NCC(O)CO)c(=O)c3c(F)ccc(F)c32)cc1] | racemate | 419.1 |
| 27 | 5,8-difluoro-N-[(1S,2S)-2-hydroxycyclohexyl]-1-(4-methoxybenzyl)-4-oxo-1,4-dihydroquinoline-3-carboxamide | 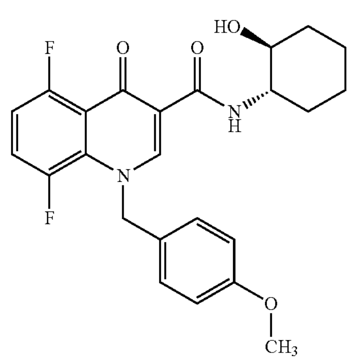 [SMILES: COc1ccc(Cn2cc(C(=O)N[C@H]3CCCC[C@@H]3O)c(=O)c3c(F)ccc(F)c32)cc1] | 1S,2S | 443.3 |
| 28 | 5,8-difluoro-N-[(1R,2R)-2-hydroxycyclohexyl]-1-(4-methoxybenzyl)-4-oxo-1,4-dihydroquinoline-3-carboxamide | 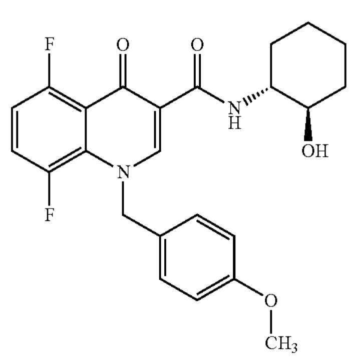 [SMILES: COc1ccc(Cn2cc(C(=O)N[C@@H]3CCCC[C@H]3O)c(=O)c3c(F)ccc(F)c32)cc1] | 1R,2R | 443.1 |

TABLE 1-continued

| Ex. No. | compound name | structure | stereo-chemistry | MS (M + H)+ |
|---|---|---|---|---|
| 29 | 5,8-difluoro-N-[(2S)-2-hydroxypropyl]-1-(4-methoxybenzyl)-4-oxo-1,4-dihydroquinoline-3-carboxamide | 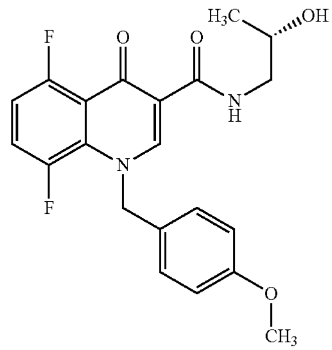 [SMILES: COc1ccc(Cn2cc(C(=O)NC[C@H](C)O)c(=O)c3c(F)ccc(F)c32)cc1] | S | 403.1 |
| 30 | 5,8-difluoro-N-[(2R)-2-hydroxypropyl]-1-(4-methoxybenzyl)-4-oxo-1,4-dihydroquinoline-3-carboxamide | 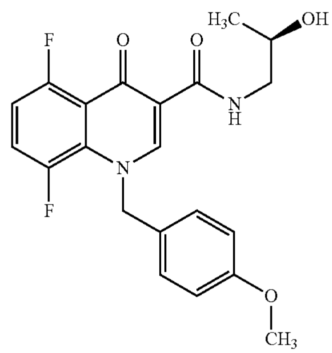 [SMILES: COc1ccc(Cn2cc(C(=O)NC[C@@H](C)O)c(=O)c3c(F)ccc(F)c32)cc1] | R | 403.1 |
| 31 | 5,8-difluoro-3-[(3-hydroxyazetidin-1-yl)carbonyl]-1-(4-methoxybenzyl)-quinolin-4(1H)-one | 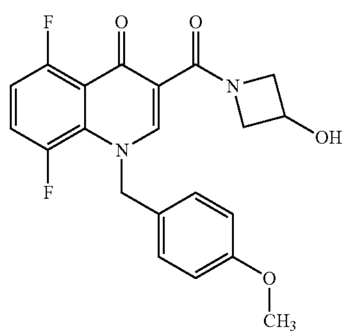 [SMILES: COc1ccc(Cn2cc(C(=O)N3CC(O)C3)c(=O)c3c(F)ccc(F)c32)cc1] | | 401.1 |
| 32 | 5,8-difluoro-N-(2-hydroxy-2-methylpropyl)-1-(4-methoxybenzyl)-4-oxo-1,4-dihydroquinoline-3-carboxamide | 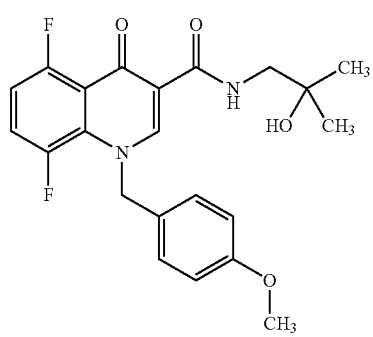 [SMILES: COc1ccc(Cn2cc(C(=O)NCC(C)(C)O)c(=O)c3c(F)ccc(F)c32)cc1] | | 417.1 |

TABLE 1-continued

| Ex. No. | compound name | structure | stereo-chemistry | MS (M + H)+ |
|---|---|---|---|---|
| 33 | 5,8-difluoro-N-[(1-hydroxycyclohexyl)-methyl]-1-(4-methoxybenzyl)-4-oxo-1,4-dihydroquinoline-3-carboxamide | 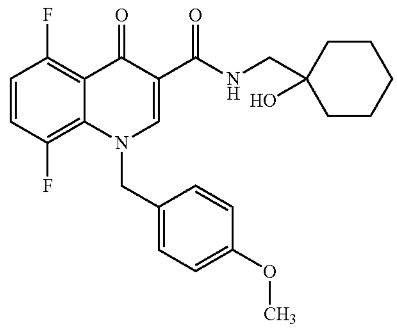 [SMILES: COc1ccc(Cn2cc(C(=O)NCC3(O)CCCCC3)c(=O)c3c(F)ccc(F)c32)cc1] | | 457.1 |
| 34 | 5,8-difluoro-1-(4-methoxybenzyl)-N-(2-methylphenyl)-4-oxo-1,4-dihydroquinoline-3-carboxamide | 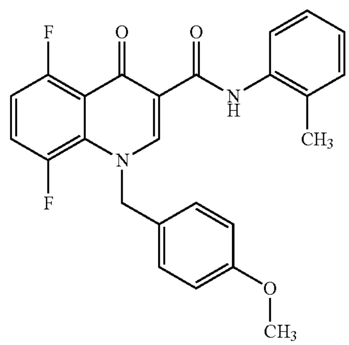 [SMILES: COc1ccc(Cn2cc(C(=O)Nc3ccccc3C)c(=O)c3c(F)ccc(F)c32)cc1] | | 435.2 |
| 35 | 5,8-difluoro-N-[2-(hydroxymethyl)-phenyl]-1-(4-methoxybenzyl)-4-oxo-1,4-dihydroquinoline-3-carboxamide | 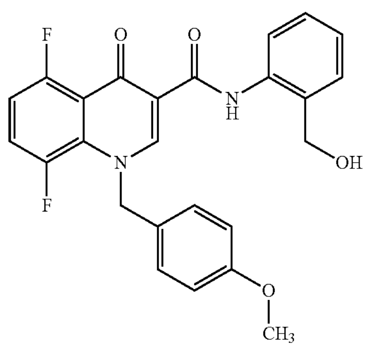 [SMILES: COc1ccc(Cn2cc(C(=O)Nc3ccccc3CO)c(=O)c3c(F)ccc(F)c32)cc1] | | 451.1 |
| 36 | 5,8-difluoro-N-(3-hydroxypropyl)-1-(4-methoxybenzyl)-4-oxo-1,4-dihydroquinoline-3-carboxamide | 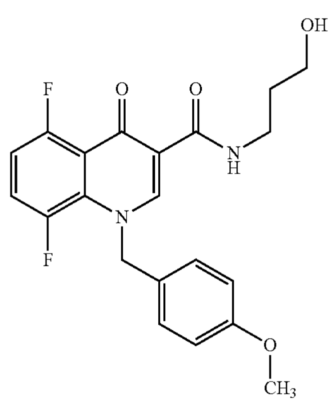 [SMILES: COc1ccc(Cn2cc(C(=O)NCCCO)c(=O)c3c(F)ccc(F)c32)cc1] | | 403.1 |

TABLE 1-continued

| Ex. No. | compound name | structure | stereo-chemistry | MS (M + H)+ |
|---|---|---|---|---|
| 37 | 5,8-difluoro-N-(2-hydroxyethyl)-1-(4-methoxybenzyl)-N-methyl-4-oxo-1,4-dihydroquinoline-3-carboxamide | 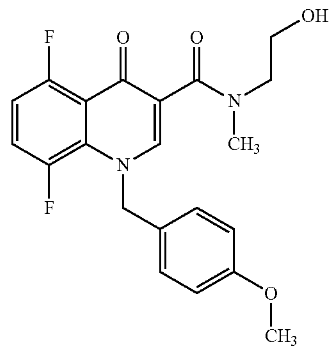 [SMILES: COc1ccc(Cn2cc(C(=O)N(C)CCO)c(=O)c3c(F)ccc(F)c32)cc1] | | 403.1 |
| 38 | 5,8-difluoro-3-{[(2R)-2-(hydroxymethyl)-pyrrolidin-1-yl]carbonyl}-1-(4-methoxybenzyl)-quinolin-4(1H)-one | 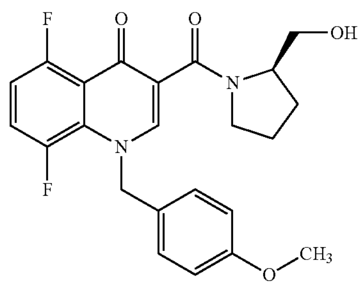 [SMILES: COc1ccc(Cn2cc(C(=O)N3CCC[C@@H]3CO)c(=O)c3c(F)ccc(F)c32)cc1] | R | 429.1 |
| 39 | 5,8-difluoro-N-[(1S,2S)-2-hydroxy-2,3-dihydro-1H-inden-1-yl]-1-(4-methoxybenzyl)-4-oxo-1,4-dihydroquinoline-3-carboxamide | 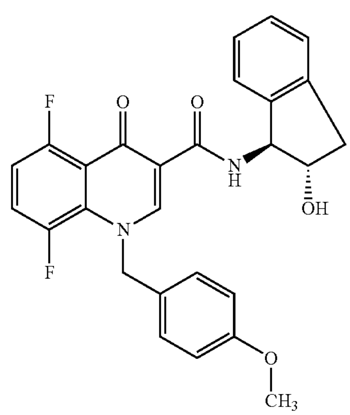 [SMILES: COc1ccc(Cn2cc(C(=O)N[C@H]3c4ccccc4C[C@@H]3O)c(=O)c3c(F)ccc(F)c32)cc1] | 1S,2S | 477.1 |
| 40 | 5,8-difluoro-1-(4-methoxybenzyl)-4-oxo-N-(1H-pyrazol-3-yl)-1,4-dihydroquinoline-3-carboxamide | 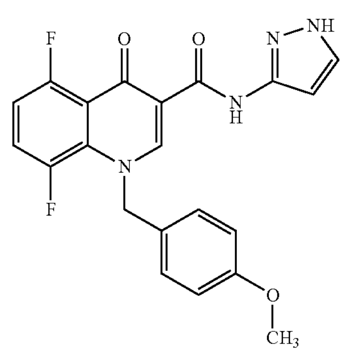 [SMILES: COc1ccc(Cn2cc(C(=O)Nc3cc[nH]n3)c(=O)c3c(F)ccc(F)c32)cc1] | | 411.1 |

TABLE 1-continued

| Ex. No. | compound name | structure | stereo-chemistry | MS (M + H)+ |
|---|---|---|---|---|
| 41 | 1-(4-methoxybenzyl)-4-oxo-N-phenyl-1,4-dihydrocinnoline-3-carboxamide | 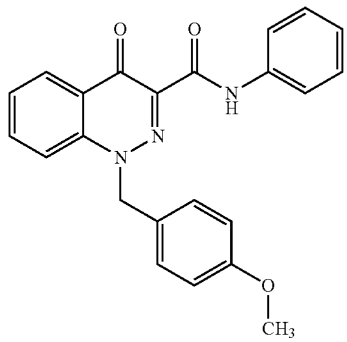 [SMILES: COc1ccc(Cn2nc(C(=O)Nc3ccccc3)c(=O)c3ccccc32)cc1] | | 386.1 |
| 42 | 3-[(3-hydroxypiperidin-1-yl)carbonyl]-1-(4-methoxybenzyl)-cinnolin-4(1H)-one | 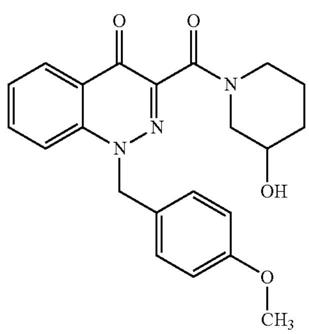 [SMILES: COc1ccc(Cn2nc(C(=O)N3CCCC(O)C3)c(=O)c3ccccc32)cc1] | racemate | 394.1 |
| 43 | 1-(4-methoxybenzyl)-3-(piperidin-1-ylcarbonyl)cinnolin-4(1H)-one | 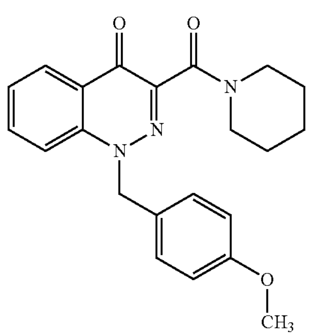 [SMILES: COc1ccc(Cn2nc(C(=O)N3CCCCC3)c(=O)c3ccccc32)cc1] | | 378.2 |
| 44 | 1-(4-methoxybenzyl)-N-(2-methoxyethyl)-4-oxo-1,4-dihydrocinnoline-3-carboxamide | 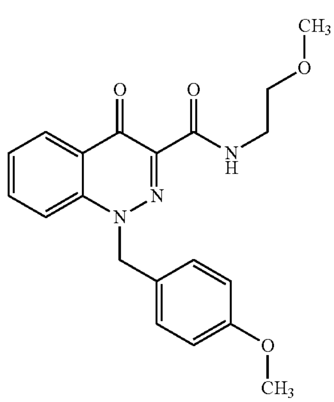 [SMILES: COCCNC(=O)c1nn(Cc2ccc(OC)cc2)c2ccccc2c1=O] | | 368.1 |

TABLE 1-continued

| Ex. No. | compound name | structure | stereo-chemistry | MS (M + H)+ |
|---|---|---|---|---|
| 45 | 1-(4-methoxybenzyl)-4-oxo-N-(piperidin-1-yl)-1,4-dihydrocinnoline-3-carboxamide | 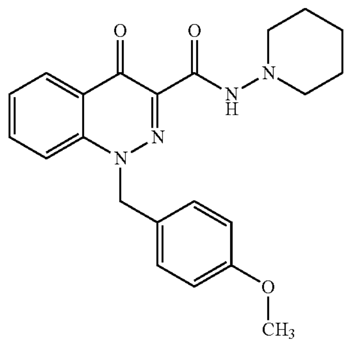 [SMILES: COc1ccc(Cn2nc(C(=O)NN3CCCCC3)c(=O)c3ccccc32)cc1] | | 393.2 |
| 46 | N-(2-hydroxy-2-phenylethyl)-1-(4-methoxybenzyl)-4-oxo-1,4-dihydrocinnoline-3-carboxamide | 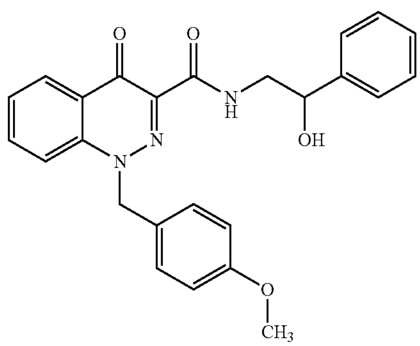 [SMILES: COc1ccc(Cn2nc(C(=O)NCC(O)c3ccccc3)c(=O)c3ccccc32)cc1] | racemate | 430.1 |
| 47 | 1-(4-methoxybenzyl)-4-oxo-N-(tetrahydrofuran-2-ylmethyl)-1,4-dihydrocinnoline-3-carboxamide | 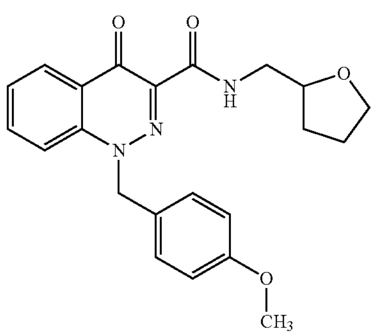 [SMILES: COc1ccc(Cn2nc(C(=O)NCC3CCCO3)c(=O)c3ccccc32)cc1] | racemate | 394.1 |
| 48 | N,N-bis(2-hydroxyethyl)-1-(4-methoxybenzyl)-4-oxo-1,4-dihydrocinnoline-3-carboxamide | 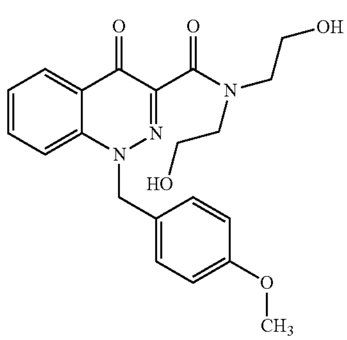 [SMILES: COc1ccc(Cn2nc(C(=O)N(CCO)CCO)c(=O)c3ccccc32)cc1] | | 398.1 |

TABLE 1-continued

| Ex. No. | compound name | structure | stereo-chemistry | MS (M + H)+ |
|---|---|---|---|---|
| 49 | N-[(1,2-trans)-2-hydroxycyclopentyl]-1-(4-methoxybenzyl)-4-oxo-1,4-dihydrocinnoline-3-carboxamide | 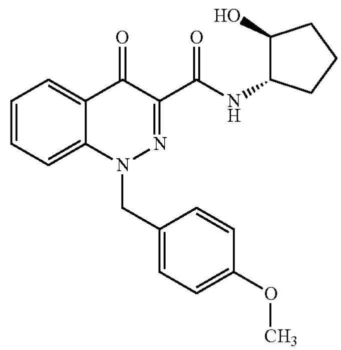 [SMILES: COc1ccc(Cn2nc(C(=O)N[C@H]3CCC[C@@H]3O)c(=O)c3ccccc32)cc1] | 1,2-trans racemate | 394.1 |
| 50 | N-(2,3-dihydroxypropyl)-1-(4-methoxybenzyl)-4-oxo-1,4-dihydrocinnoline-3-carboxamide | 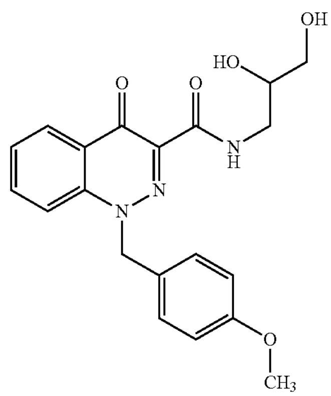 [SMILES: COc1ccc(Cn2nc(C(=O)NCC(O)CO)c(=O)c3ccccc32)cc1] | racemate | 384.1 |
| 51 | N-[(1S,2S)-2-hydroxycyclohexyl]-1-(4-methoxybenzyl)-4-oxo-1,4-dihydrocinnoline-3-carboxamide | 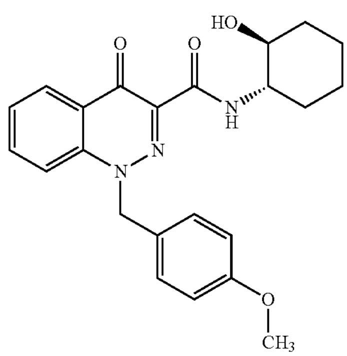 [SMILES: COc1ccc(Cn2nc(C(=O)N[C@H]3CCCC[C@@H]3O)c(=O)c3ccccc32)cc1] | 1S,2S | 408.2 |
| 52 | N-[(1R,2R)-2-hydroxycyclohexyl]-1-(4-methoxybenzyl)-4-oxo-1,4-dihydrocinnoline-3-carboxamide | 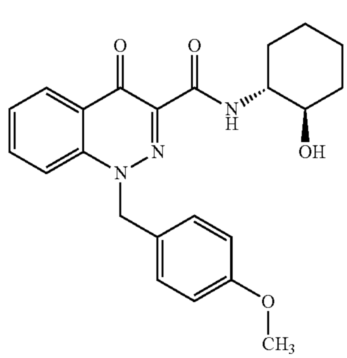 [SMILES: COc1ccc(Cn2nc(C(=O)N[C@@H]3CCCC[C@H]3O)c(=O)c3ccccc32)cc1] | 1R,2R | 408.2 |

TABLE 1-continued

| Ex. No. | compound name | structure | stereo-chemistry | MS (M + H)+ |
|---|---|---|---|---|
| 53 | N-[(2S)-2-hydroxypropyl]-1-(4-methoxybenzyl)-4-oxo-1,4-dihydrocinnoline-3-carboxamide | 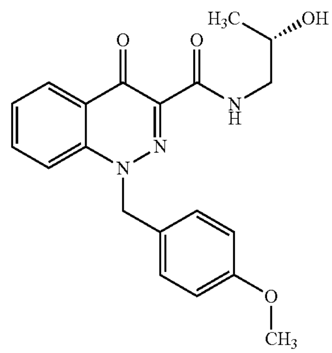 [SMILES: COc1ccc(Cn2nc(C(=O)NC[C@H](C)O)c(=O)c3ccccc32)cc1] | S | 368.1 |
| 54 | N-[(2R)-2-hydroxypropyl]-1-(4-methoxybenzyl)-4-oxo-1,4-dihydrocinnoline-3-carboxamide | 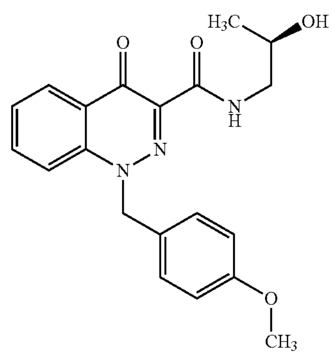 [SMILES: COc1ccc(Cn2nc(C(=O)NC[C@@H](C)O)c(=O)c3ccccc32)cc1] | R | 368.1 |
| 55 | 3-[(3-hydroxyazetidin-1-yl)carbonyl]-1-(4-methoxybenzyl)-cinnolin-4(1H)-one | 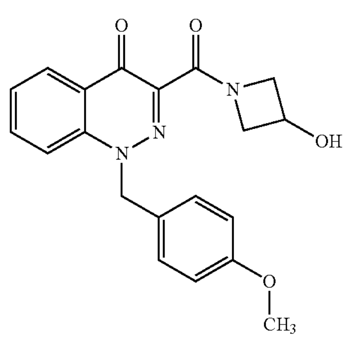 [SMILES: COc1ccc(Cn2nc(C(=O)N3CC(O)C3)c(=O)c3ccccc32)cc1] | | 336.1 |
| 56 | N-(2-hydroxy-2-methylpropyl)-1-(4-methoxybenzyl)-4-oxo-1,4-dihydrocinnoline-3-carboxamide | 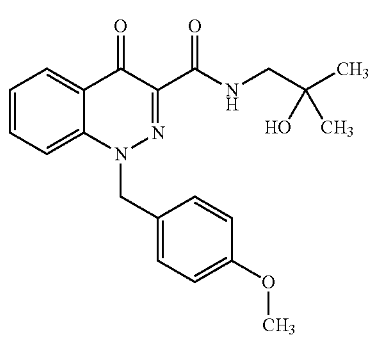 [SMILES: COc1ccc(Cn2nc(C(=O)NCC(C)(C)O)c(=O)c3ccccc32)cc1] | | 382.2 |

TABLE 1-continued

| Ex. No. | compound name | structure | stereo-chemistry | MS (M + H)+ |
|---|---|---|---|---|
| 57 | N-[(1-hydroxycyclohexyl)-methyl]-1-(4-methoxybenzyl)-4-oxo-1,4-dihydrocinnoline-3-carboxamide | 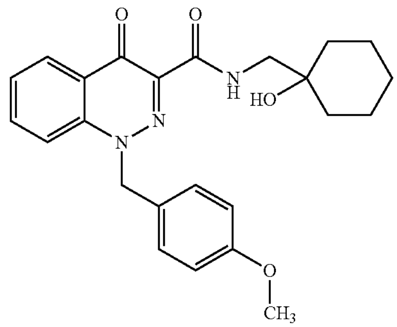 [SMILES: COc1ccc(Cn2nc(C(=O)NCC3(O)CCCCC3)c(=O)c3ccccc32)cc1] | | 422.2 |
| 58 | 1-(4-methoxybenzyl)-N-(2-methylphenyl)-4-oxo-1,4-dihydrocinnoline-3-carboxamide | 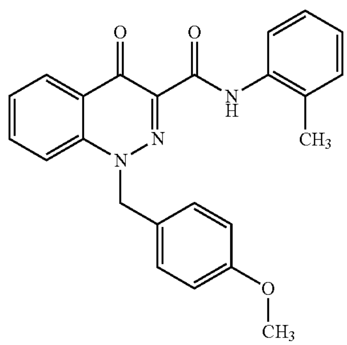 [SMILES: COc1ccc(Cn2nc(C(=O)Nc3ccccc3C)c(=O)c3ccccc32)cc1] | | 400.1 |
| 59 | N-[2-(hydroxymethyl)-phenyl]-1-(4-methoxybenzyl)-4-oxo-1,4-dihydrocinnoline-3-carboxamide | 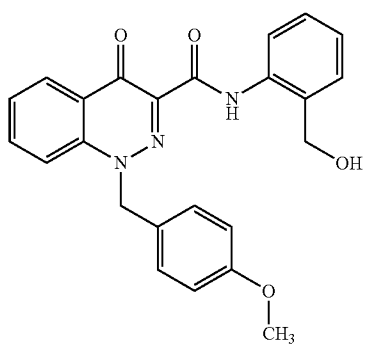 [SMILES: COc1ccc(Cn2nc(C(=O)Nc3ccccc3CO)c(=O)c3ccccc32)cc1] | | 416.1 |
| 60 | N-(3-hydroxypropyl)-1-(4-methoxybenzyl)-4-oxo-1,4-dihydrocinnoline-3-carboxamide | 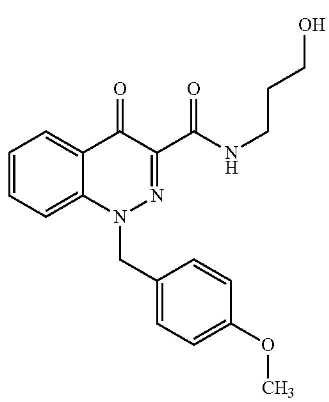 [SMILES: COc1ccc(Cn2nc(C(=O)NCCCO)c(=O)c3ccccc32)cc1] | | 368.2 |

TABLE 1-continued

| Ex. No. | compound name | structure | stereo- chemistry | MS (M + H)+ |
|---|---|---|---|---|
| 61 | N-(2-hydroxyethyl)-1-(4-methoxybenzyl)-N-methyl-4-oxo-1,4-dihydrocinnoline-3-carboxamide | 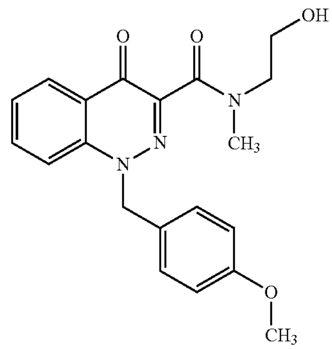 [SMILES: COc1ccc(Cn2nc(C(=O)N(C)CCO)c(=O)c3ccccc32)cc1] | | 368.2 |
| 62 | 3-{[(2R)-2-(hydroxymethyl)-pyrrolidin-1-yl]carbonyl}-1-(4-methoxybenzyl)-cinnolin-4(1H)-one | 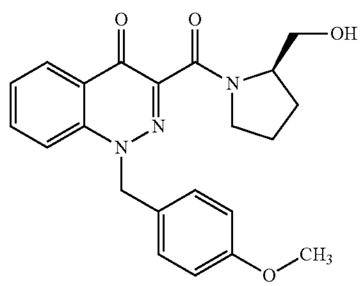 [SMILES: COc1ccc(Cn2nc(C(=O)N3CCC[C@@H]3CO)c(=O)c3ccccc32)cc1] | R | 394.1 |
| 63 | N-[(1S,2S)-2-hydroxy-2,3-dihydro-1H-inden-1-yl]-1-(4-methoxybenzyl)-4-oxo-1,4-dihydrocinnoline-3-carboxamide | 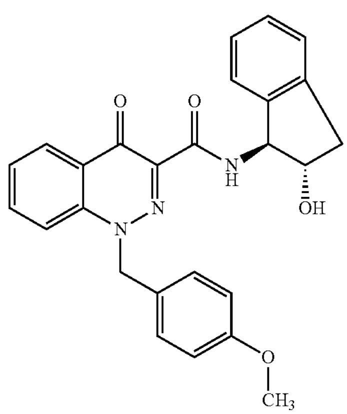 [SMILES: COc1ccc(Cn2nc(C(=O)N[C@H]3c4ccccc4C[C@@H]3O)c(=O)c3ccccc32)cc1] | 1S,2S | 442.1 |
| 64 | 1-(4-methoxybenzyl)-4-oxo-N-(1H-pyrazol-3-yl)-1,4-dihydrocinnoline-3-carboxamide | 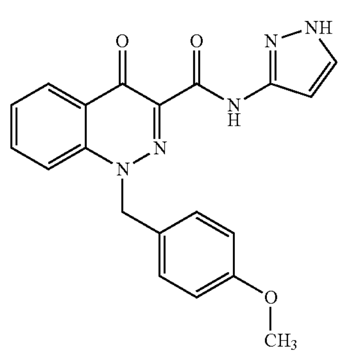 [SMILES: COc1ccc(Cn2nc(C(=O)Nc3cc[nH]n3)c(=O)c3ccccc32)cc1] | | 376.1 |

TABLE 1-continued

| Ex. No. | compound name | structure | stereo-chemistry | MS (M + H)+ |
|---|---|---|---|---|
| 65 | 5,8-difluoro-N-[(1,2-trans)-2-(hydroxymethyl)-cyclohexyl]-1-(4-methoxybenzyl)-4-oxo-1,4-dihydroquinoline-3-carboxamide | 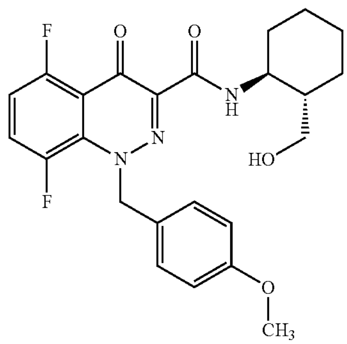 [SMILES: COc1ccc(Cn2nc(C(=O)N[C@H]3CCCC[C@@H]3CO)c(=O)c3c(F)ccc(F)c32)cc1] | 1,2-trans racemate | 457.0 |
| 66 | N-[(1,2-trans)-2-(hydroxymethyl)-cyclohexyl]-1-(4-methoxybenzyl)-4-oxo-1,4-dihydrocinnoline-3-carboxamide | 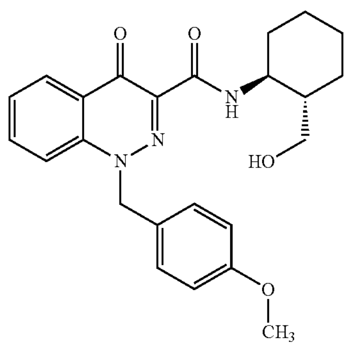 [SMILES: COc1ccc(Cn2nc(C(=O)N[C@H]3CCCC[C@@H]3CO)c(=O)c3ccccc32)cc1] | 1,2-trans racemate | 422.3 |
| 67 | 5,8-difluoro-N-(furan-2-ylmethyl)-1-(4-methoxybenzyl)-4-oxo-1,4-dihydroquinoline-3-carboxamide | 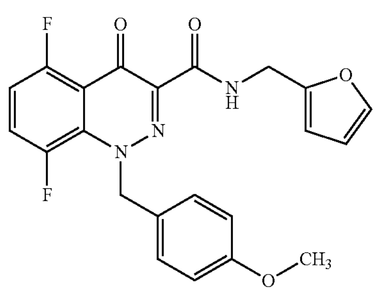 [SMILES: COc1ccc(Cn2nc(C(=O)NCc3ccco3)c(=O)c3c(F)ccc(F)c32)cc1] | | 425.2 |
| 68 | 5,8-difluoro-1-(4-methoxybenzyl)-4-oxo-N-(tetrahydrofuran-3-yl)-1,4-dihydroquinoline-3-carboxamide | 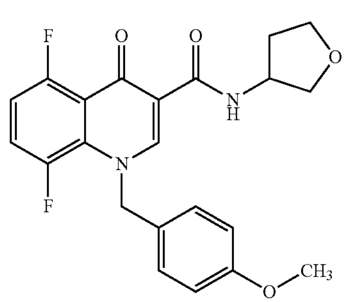 [SMILES: COc1ccc(Cn2cc(C(=O)NC3CCOC3)c(=O)c3c(F)ccc(F)c32)cc1] | racemate | 415.1 |

TABLE 1-continued

| Ex. No. | compound name | structure | stereo-chemistry | MS (M + H)+ |
|---|---|---|---|---|
| 69 | 5,8-difluoro-1-(4-methoxybenzyl)-4-oxo-N-[2-(piperidin-1-yl)ethyl]-1,4-dihydroquinoline-3-carboxamide | 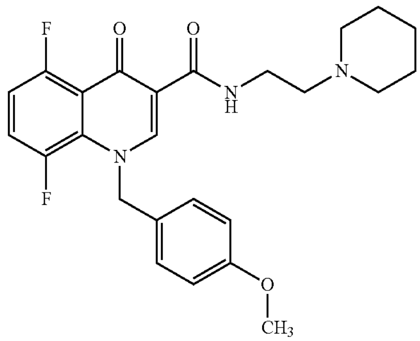 [SMILES: COc1ccc(Cn2cc(C(=O)NCCN3CCCCC3)c(=O)c3c(F)ccc(F)c32)cc1] | | 456.2 |
| 70 | 5,8-difluoro-1-(4-methoxybenzyl)-N-[2-(morpholin-4-yl)ethyl]-4-oxo-1,4-dihydroquinoline-3-carboxamide | 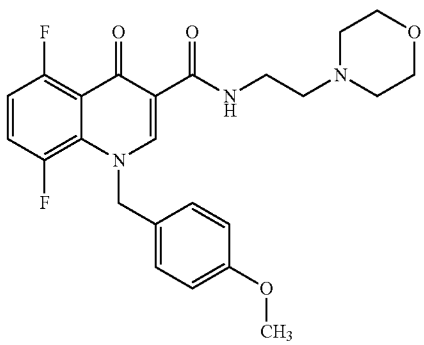 [SMILES: COc1ccc(Cn2cc(C(=O)NCCN3CCOCC3)c(=O)c3c(F)ccc(F)c32)cc1] | | 458.2 |
| 71 | 1,5-anhydro-2,3-dideoxy-3-({[1-(4-methoxybenzyl)-4-oxo-1,4-dihydrocinnolin-3-yl]carbonyl}amino)-DL-threo-pentitololin | 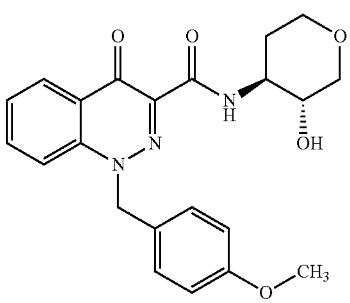 [SMILES: COc1ccc(Cn2nc(C(=O)N[C@H]3CCOC[C@@H]3O)c(=O)c3ccccc32)cc1] | racemate | 410.2 |

1H NMR (400 MHz, DMSO-d6) δ 1.52 (1H, brs), 2.09 (1H, brs), 3.12 (1H, t, J = 10.1 Hz), 3.36-3.55 (2H, m), 3.70 (3H, s), 3.74-3.95 (3H, m), 5.16 (1H, d, J = 5.6 Hz), 5.83 (2H, s), 6.90 (2H, d, J = 8.8 Hz), 7.28 (2H, d, J = 8.8 Hz), 7.54-7.67 (1H, m), 7.82-7.93 (1H, m), 7.93-8.02 (1H, m), 8.28 (1H, d, J = 8.1 Hz), 9.82 (1H, d, J = 7.3 Hz).

| 72 | 5,8-difluoro-N-(2-fluorophenyl)-1-(4-methoxybenzyl)-4-oxo-1,4-dihydroquinoline-3-carboxamide | | | 439.2 |

TABLE 1-continued

| Ex. No. | compound name | structure | stereo-chemistry | MS (M + H)+ |
|---|---|---|---|---|
| 73 | 1-(4-carbamoylbenzyl)-4-oxo-1,4-dihydrocinnoline-3-carboxamide | 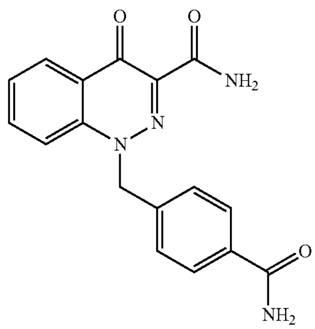 [SMILES: NC(=O)c1ccc(Cn2nc(C(N)=O)c(=O)c3ccccc32)cc1] | | 323.1 |
| 74 | 1-(4-carbamoylbenzyl)-N-[(1,2-trans)-2-hydroxycyclohexyl]-4-oxo-1,4-dihydroquinoline-3-carboxamide | 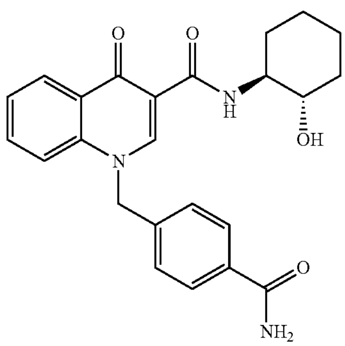 | 1,2-trans racemate | 420.2 |

1H NMR (300 MHz, DMSO-d6) δ 1.30 (4H, d, J = 8.3 Hz), 1.55-1.71 (2H, m), 1.87 (1H, d, J = 8.3 Hz), 2.03 (1H, d, J = 10.6 Hz), 3.34-3.46 (1H, m), 3.71 (1H, d, J = 8.7 Hz), 4.81 (1H, d, J = 4.9 Hz), 5.85 (2H, s), 7.28 (2H, d, J = 8.3 Hz), 7.34 (1H, brs), 7.50 (1H, t, J = 7.2 Hz), 7.65-7.77 (2H, m), 7.82 (2H, d, J = 8.3 Hz), 7.92 (1H, brs), 8.36 (1H, d, J = 7.6 Hz), 9.09 (1H, s), 10.08 (1H, d, J = 7.6 Hz).

| 75 | 1-(4-carbamoylbenzyl)-N-[(1,2-trans)-2-hydroxycyclohexyl]-4-oxo-1,4-dihydrocinnoline-3-carboxamide | 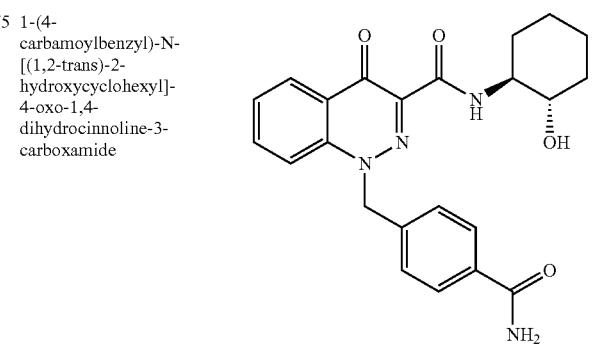 | 1,2-trans racemate | 421.2 |

1H NMR (300 MHz, DMSO-d6) δ 1.16-1.41 (4H, m), 1.55-1.71 (2H, m), 1.82-1.93 (1H, m), 1.98-2.09 (1H, m), 3.35-3.47 (1H, m), 3.63-3.76 (1H, m), 4.79 (1H, d, J = 5.3 Hz), 5.96 (2H, s), 7.35 (3H, d, J = 8.0 Hz), 7.57-7.64 (1H, m), 7.78-7.89 (4H, m), 7.93 (1H, brs), 8.29 (1H, d, J = 8.0 Hz), 9.74 (1H, d, J = 7.6 Hz).

TABLE 1-continued

| Ex. No. | compound name | structure | stereo-chemistry | MS (M + H)+ |
|---|---|---|---|---|
| 76 | 3-(1,3-dihydro-2H-isoindol-2-ylcarbonyl)-5,8-difluoro-1-(4-methoxybenzyl)-quinolin-4(1H)-one | 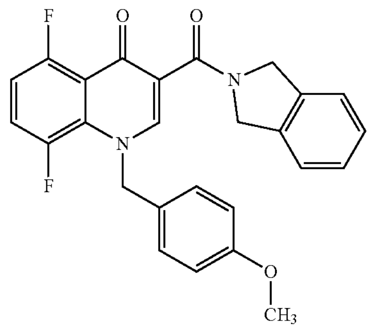 [SMILES: COc1ccc(Cn2cc(C(=O)N3Cc4ccccc4C3)c(=O)c3c(F)ccc(F)c32)cc1] | | 447.2 |
| 77 | N-[(1R,2S)-3,3-difluoro-2-hydroxycyclohexyl]-5,8-difluoro-1-(4-methoxybenzyl)-4-oxo-1,4-dihydroquinoline-3-carboxamide | 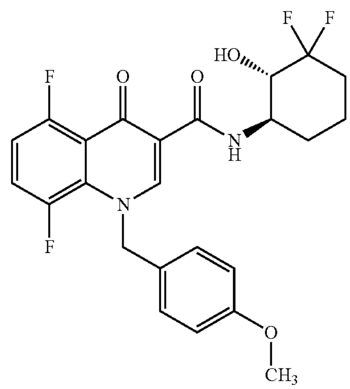 [SMILES: COc1ccc(Cn2cc(C(=O)N[C@@H]3CCCC(F)(F)[C@H]3O)c(=O)c3c(F)ccc(F)c32)cc1] | 1R,2S | 479.3 |
| 78 | 1-(4-carbamoylbenzyl)-N-[(1S,2S)-2-hydroxycyclohexyl]-4-oxo-1,4-dihydroquinoline-3-carboxamide | 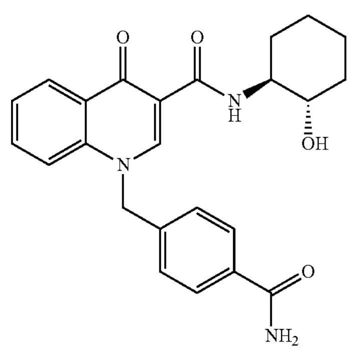 [SMILES: NC(=O)c1ccc(Cn2cc(C(=O)N[C@H]3CCCC[C@@H]3O)c(=O)c3ccccc32)cc1] | 1S,2S | 420.3 |
| 79 | 8-chloro-N-[(1,2-trans)-2-hydroxycyclohexyl]-1-(4-methoxybenzyl)-4-oxo-1,4-dihydroquinoline-3-carboxamide | 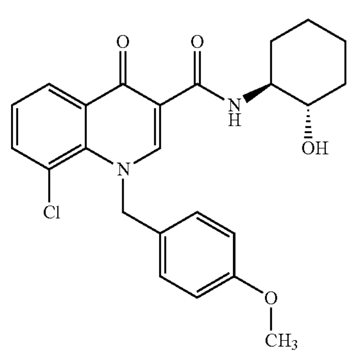 [SMILES: COc1ccc(Cn2cc(C(=O)N[C@H]3CCCC[C@@H]3O)c(=O)c3cccc(Cl)c32)cc1] | 1,2-trans racemate | 441.3 |

TABLE 1-continued

| Ex. No. | compound name | structure | stereo-chemistry | MS (M + H)+ |
|---|---|---|---|---|
| 80 | 8-fluoro-N-[(1,2-trans)-2-hydroxycyclohexyl]-4-oxo-1-[4-(1H-pyrazol-1-yl)benzyl]-1,4-dihydroquinoline-3-carboxamide | 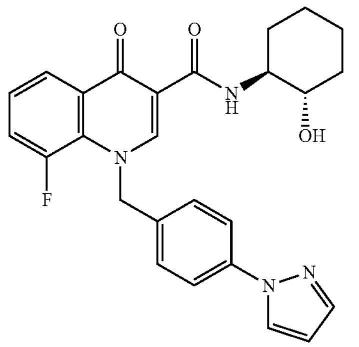 [SMILES: O=C(N[C@H]1CCCC[C@@H]1O)c1cn(Cc2ccc(-n3cccn3)cc2)c2c(F)cccc2c1=O] | 1,2-trans racemate | 461.3 |
| 81 | 1-(4-carbamoylbenzyl)-N-[(1,2-trans)-2-hydroxycyclohexyl]-4-oxo-8-(trifluoromethoxy)-1,4-dihydroquinoline-3-carboxamide | 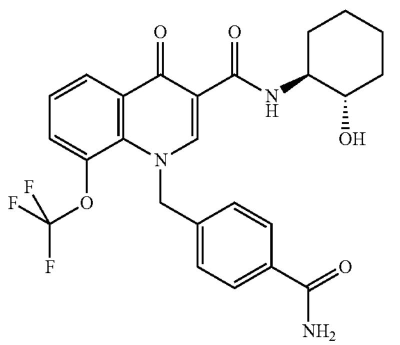 [SMILES: NC(=O)c1ccc(Cn2cc(C(=O)N[C@H]3CCCC[C@@H]3O)c(=O)c3cccc(OC(F)(F)F)c32)cc1] | 1,2-trans racemate | 504.3 |
| 82 | 1-[4-(1,1-difluoroethyl)-benzyl]-N-[(1,2-trans)-2-hydroxycyclohexyl]-4-oxo-1,4-dihydroquinoline-3-carboxamide | 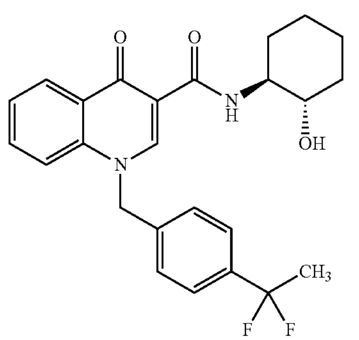 [SMILES: CC(F)(F)c1ccc(Cn2cc(C(=O)N[C@H]3CCCC[C@@H]3O)c(=O)c3ccccc32)cc1] | 1,2-trans racemate | 441.3 |
| 83 | 1,5-anhydro-2,4-dideoxy-2-({[5,8-difluoro-1-(4-methoxybenzyl)-4-oxo-1,4-dihydroquinolin-3-yl]carbonyl}amino)-DL-threo-pentitol | 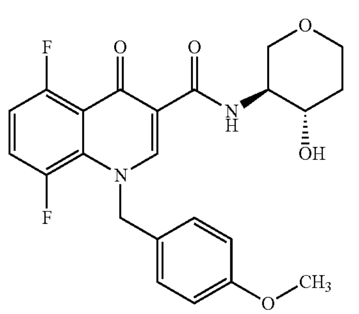 [SMILES: COc1ccc(Cn2cc(C(=O)N[C@H]3COCC[C@@H]3O)c(=O)c3c(F)ccc(F)c32)cc1] | trans racemate | 445.3 |

TABLE 1-continued

| Ex. No. | compound name | structure | stereo-chemistry | MS (M + H)+ |
|---|---|---|---|---|
| 84 | N-[(1,2-trans)-5,5-difluoro-2-hydroxycyclohexyl]-5,8-difluoro-1-(4-methoxybenzyl)-4-oxo-1,4-dihydroquinoline-3-carboxamide | 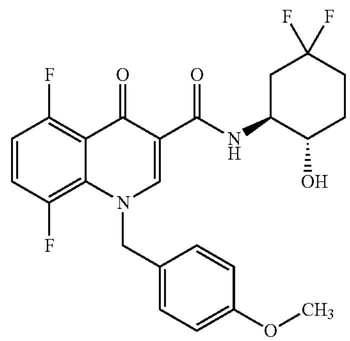 [SMILES: COc1ccc(Cn2cc(C(=O)N[C@H]3CC(F)(F)CC[C@@H]3O)c(=O)c3c(F)ccc(F)c32)cc1] | 1,2-trans racemate | 479.3 |
| 85 | N-[(1,2-trans)-2-hydroxycyclohexyl]-4-oxo-1-[4-(1H-pyrazol-5-yl)benzyl]-1,4-dihydroquinoline-3-carboxamide | 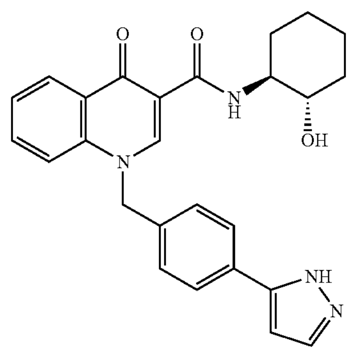 [SMILES: O=C(N[C@H]1CCCC[C@@H]1O)c1cn(Cc2ccc(-c3ccn[nH]3)cc2)c2ccccc2c1=O] | 1,2-trans racemate | 443.3 |
| 86 | 1-(4-carbamoylbenzyl)-8-chloro-N-[(1,2-trans)-2-hydroxycyclohexyl]-4-oxo-1,4-dihydroquinoline-3-carboxamide | 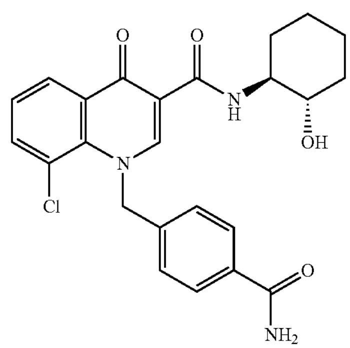 [SMILES: NC(=O)c1ccc(Cn2cc(C(=O)N[C@H]3CCCC[C@@H]3O)c(=O)c3cccc(Cl)c32)cc1] | 1,2-trans racemate | 454.3 |
| 87 | 8-chloro-N-[(1,2-trans)-2-hydroxycyclohexyl]-4-oxo-1-[4-(1H-pyrazol-1-yl)benzyl]-1,4-dihydroquinoline-3-carboxamide | 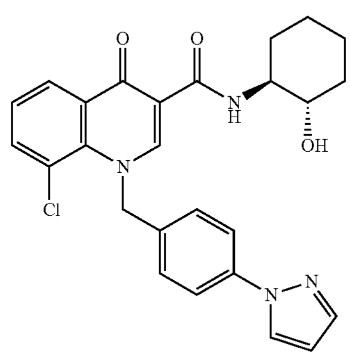 [SMILES: O=C(N[C@H]1CCCC[C@@H]1O)c1cn(Cc2ccc(-n3cccn3)cc2)c2c(Cl)cccc2c1=O] | 1,2-trans racemate | 477.1 |

TABLE 1-continued

| Ex. No. | compound name | structure | stereo-chemistry | MS (M + H)+ |
|---|---|---|---|---|
| 88 | 1-(4-carbamoylbenzyl)-N-[(1,2-trans)-2-fluorocyclohexyl]-4-oxo-1,4-dihydroquinoline-3-carboxamide | 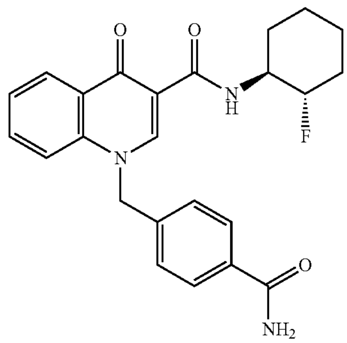 [SMILES: NC(=O)c1ccc(Cn2cc(C(=O)N[C@H]3CCCC[C@@H]3F)c(=O)c3ccccc32)cc1] | 1,2-trans racemate | 422.1 |
| 89 | 1-(4-carbamoylbenzyl)-N-(2,2-difluorocyclohexyl)-4-oxo-1,4-dihydroquinoline-3-carboxamide | 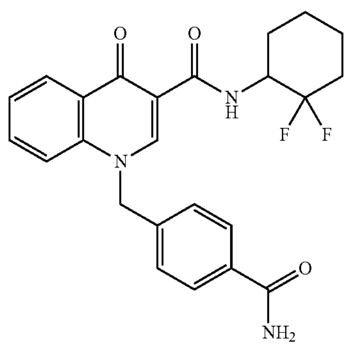 [SMILES: NC(=O)c1ccc(Cn2cc(C(=O)NC3CCCCC3(F)F)c(=O)c3ccccc32)cc1] | racemate | 440.1 |
| 90 | 5,8-difluoro-N-{[(1,2-trans)-2-hydroxycyclohexyl]-methyl}-1-(4-methoxybenzyl)-4-oxo-1,4-dihydroquinoline-3-carboxamide | 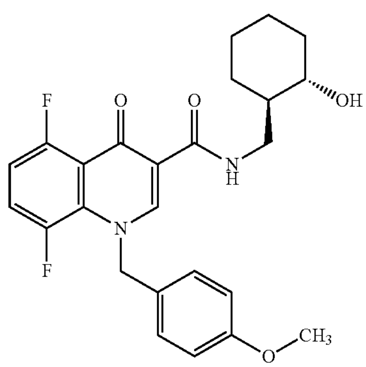 [SMILES: COc1ccc(Cn2cc(C(=O)NC[C@H]3CCCC[C@@H]3O)c(=O)c3c(F)ccc(F)c32)cc1] | 1,2-trans racemate | 457.3 |
| 91 | N-[3,5-bis(trifluoromethyl)phenyl]-5,8-difluoro-1-(4-methoxybenzyl)-4-oxo-1,4-dihydroquinoline-3-carboxamide | 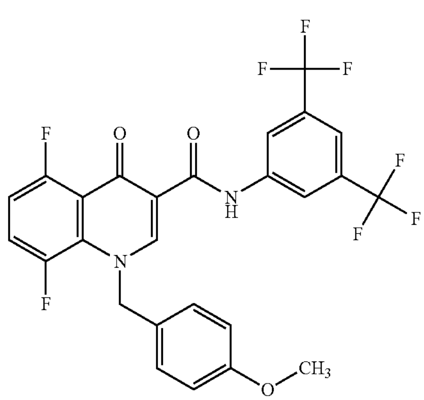 [SMILES: COc1ccc(Cn2cc(C(=O)Nc3cc(C(F)(F)F)cc(C(F)(F)F)c3)c(=O)c3c(F)ccc(F)c32)cc1] | | 557.3 |

TABLE 1-continued

| Ex. No. | compound name | structure | stereo-chemistry | MS (M + H)+ |
|---|---|---|---|---|
| 92 | 8-fluoro-N-[(1,2-trans)-2-hydroxycyclopentyl]-4-oxo-1-[4-(1H-pyrazol-1-yl)benzyl]-1,4-dihydroquinoline-3-carboxamide | 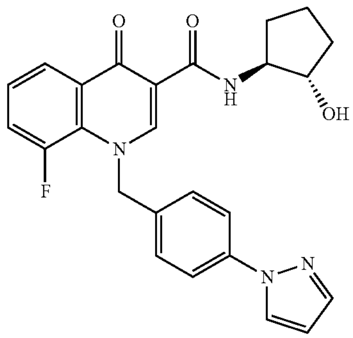 [SMILES: O=C(N[C@H]1CCC[C@@H]1O)c1cn(Cc2ccc(-n3cccn3)cc2)c2c(F)cccc2c1=O] | 1,2-trans racemate | 447.2 |
| 93 | N-[(1,2-trans)-2-hydroxycyclopentyl]-1-[4-(2-methylpyridin-4-yl)benzyl]-4-oxo-1,4-dihydroquinoline-3-carboxamide | 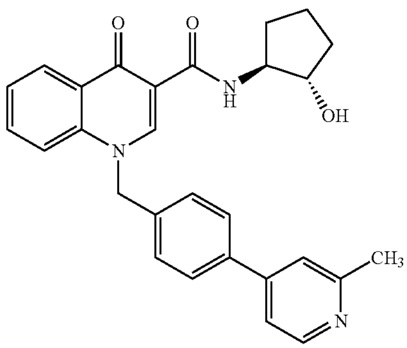 [SMILES: Cc1cc(-c2ccc(Cn3cc(C(=O)N[C@H]4CCC[C@@H]4O)c(=O)c4ccccc43)cc2)ccn1] | 1,2-trans racemate | 454.4 |
| 94 | 1-[4-(1,3-dimethyl-1H-pyrazol-4-yl)benzyl]-N-[(1,2-trans)-2-hydroxycyclopentyl]-4-oxo-1,4-dihydroquinoline-3-carboxamide | 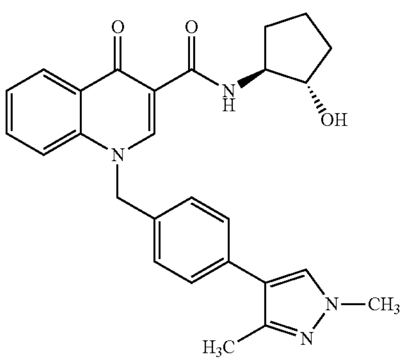 [SMILES: Cc1nn(C)cc1-c1ccc(Cn2cc(C(=O)N[C@H]3CCC[C@@H]3O)c(=O)c3ccccc32)cc1] | 1,2-trans racemate | 457.4 |

Formulation Example 1

| (1) Compound obtained in Example 1 | 10.0 g |
|---|---|
| (2) Lactose | 60.0 g |
| (3) Cornstarch | 35.0 g |
| (4) Gelatin | 3.0 g |
| (5) Magnesium stearate | 2.0 g |

A mixture of the compound (10.0 g) obtained in Example 1, lactose (60.0 g) and cornstarch (35.0 g) is passed through a 1 mm mesh sieve by using 10 wt % aqueous gelatin solution (30 mL) (3.0 g as gelatin) and the granules are dried at 40° C. and sieved again. The obtained granules are mixed with magnesium stearate (2.0 g) and the mixture is compressed. The obtained core tablets are coated with a sugar coating of an aqueous suspension of saccharose, titanium dioxide, talc and gum arabic. The coated tablets are glazed with beeswax to give 1000 coated tablets.

Formulation Example 2

| (1) Compound obtained in Example 1 | 10.0 g |
|---|---|
| (2) Lactose | 70.0 g |
| (3) Cornstarch | 50.0 g |
| (4) Soluble starch | 7.0 g |
| (5) Magnesium stearate | 3.0 g |

The compound (10.0 g) obtained in Example 1 and magnesium stearate (3.0 g) are granulated using aqueous soluble starch solution (70 mL) (7.0 g as soluble starch), dried and mixed with lactose (70.0 g) and cornstarch (50.0 g). The mixture is compressed to give 1000 tablets.

Experimental Example 1

Measurement of Cholinergic Muscarinic M1 Receptor Positive Allosteric Modulator (M1PAM) Activity The activity of a test compound in the presence of acetylcholine at EC20 concentration (final concentration 0.6 nM), which affords an action corresponding to 20% of the maximum activity, was measured as M1PAM activity. The method is as follows. CHO-K1 cells forcibly expressing a human M1 receptor (hCHRM1) were plated on a 384-well black clear bottom plate (BD Falcon) at 5,000 cells/well, and cultured in an incubator at 37° C., 5% $CO_2$ for 1 day. The medium in the cell plate was removed, and assay buffer A (Recording medium (DOJINDO LABORATORIES), 0.1% bovine serum albumin (BSA) (Wako Pure Chemical Industries, Ltd.), 2.5 µg/mL Fluo-4 AM (DOJINDO LABORATORIES), 0.08% Pluronic F127 (DOJINDO LABORATORIES), 1.25 mM probenecid (DOJINDO LABORATORIES)) containing a calcium indicator was added at 30 µL/well. The cells were left standing in the incubator at 37° C., 5% $CO_2$ for 30 min, and further left standing at room temperature for 30 min. A test compound prepared by diluting with assay buffer B (HBSS (Invitrogen), 20 mM HEPES (Invitrogen), 0.1% BSA) containing 2.4 nM acetylcholine was added at 10 µL/well, and the fluorescence was measured by FLIPRtetra (Molecular Devices) for 1 min every 1 second. With the definition that the amount of change in the fluorescence on addition of acetylcholine (final concentration 1 µM) is 100% and that on addition of DMSO instead of a test compound is 0%, the activity (%) of the test compound and the inflection point in the concentration-dependent curve of the test compound were calculated as IP values. The results are shown in Table 2.

TABLE 2

| Example No. | activity (%) at 10 µM | IP value (nM) |
| --- | --- | --- |
| 1 | 90 | 630 |
| 3 | 93 | 8.7 |
| 4 | 107 | 27 |
| 5 | 86 | 2.2 |
| 6 | 98 | 16 |
| 7 | 71 | 3500 |
| 8 | 100 | 2000 |
| 10 | 103 | 55 |
| 13 | 77 | 6100 |
| 14 | 96 | 920 |
| 17 | 69 | 5800 |
| 20 | 72 | 5000 |
| 21 | 97 | 280 |
| 25 | 98 | 190 |
| 27 | 102 | 38 |
| 51 | 97 | 68 |
| 52 | 87 | 1900 |
| 65 | 96 | 420 |
| 71 | 97 | 16 |
| 73 | 96 | 63 |
| 74 | 97 | 5.4 |
| 75 | 99 | 7.7 |
| 78 | 86 | 2.2 |
| 80 | 92 | 21 |
| 82 | 83 | 170 |
| 84 | 85 | 91 |
| 85 | 90 | 4.7 |
| 88 | 101 | 12 |
| 92 | 104 | 55 |
| 93 | 95 | 12 |
| 94 | 95 | 8.5 |

Experimental Example 2

Central Migration (Kp Value) Measurement Test

A. Compounds of Examples 6 and 10 (Intravenous Administration: i.v.)
A-1. Example 6
animal: male Jcl ICR mice 7-week-old n=3
feeding: nonfasting
administration conditions: intravenous administration 0.20 mg/l mL/kg (4 compounds/cassette administration)
administration medium: N,N-dimethylacetamide (DMA)/1,3-Butanediol (1:1)
sample: plasma, brain (homogenate was prepared by adding 4-fold amount of saline)
plasma sampling time: 0.25 hr
brain sampling time: 0.25 hr
A-2. Example 10
animal: male Jcl ICR mice 8-week-old n=3
feeding: nonfasting
administration conditions: intravenous administration 0.20 mg/l mL/kg (4 compounds/cassette administration)
administration medium: DMA/1,3-Butanediol (1:1)
sample: plasma, brain (homogenate was prepared by adding 4-fold amount of saline)
plasma sampling time: 0.5 hr
brain sampling time: 0.5 hr
HPLC Analysis Conditions
column: Shimadzu Shim-pack XR-ODS (2.2 µm, 2.0×30 mm)
mobile phase A: 10 mmol/L ammonium formate/formic acid (100:0.2, v/v)
mobile phase B: acetonitrile/formic acid (100:0.2, v/v)
flow rate: 0.7 mL/min.
column temperature: 50° C.
sample injection volume: 1 µL (Example 6), 2 µL (Example 10)
plasma pre-treatment conditions: A standard solution dissolution solvent (DMSO) or a standard solution (5 µL) was added to a sample (50 µL). Acetonitrile (150 µL) containing the internal standard substance was added, and the mixture was vigorously stirred and centrifuged at 5250 rpm. A dilution solvent (160 µL) was added to the centrifuged supernatant (60 µL). The solution (40 µL) was taken, and the dilution solvent (160 µL) was added to give a sample solution for compound plasma concentration measurement (mobile phase A:mobile phase B=7:3 (v/v) was used as the dilution solvent).
brain pre-treatment conditions: The standard solution dissolution solvent (DMSO) or standard solution (5 µL) was added to a sample (50 µL). Acetonitrile (150 µL) containing the internal standard substance was added, and the mixture was vigorously stirred, and centrifuged at 5250 rpm. A dilution solvent (160 µL) was added to the centrifuged supernatant (60 µL). The solution (40 µL) was taken, and the dilution solvent (160 µL) was added to give a sample solution for intracerebral compound concentration measurement (mobile phase A:mobile phase B=7:3 (v/v) was used as the dilution solvent).
B. Compounds of Examples 92 and 94 (Oral Administration: p.o.)
animal: male Jcl ICR mice 10-week-old n=3
feeding: nonfasting
administration conditions: oral administration 1 mg/10 mL/kg (5 compounds/cassette administration)

administration medium: 0.5% methylcellulose solution sample: plasma, brain (homogenate was prepared by adding 4-fold amount of saline)

plasma sampling time: 1 hr brain sampling time: 1 hr

HPLC Analysis Conditions column: Shimadzu Shim-pack XR-ODS (2.2 μm, 2.0×30 mm)

mobile phase A: 10 mmol/L ammonium formate/formic acid (100:0.2, v/v)

mobile phase B: acetonitrile/formic acid (100:0.2, v/v)

flow rate: 0.7 mL/min.

column temperature: 50° C.

sample injection volume: 1 μL plasma pre-treatment conditions: A standard solution dissolution solvent (DMSO/acetonitrile (2:8)) or a standard solution (5 μL) was added to a sample (50 μL). Acetonitrile (150 μL) containing the internal standard substance was added, and the mixture was vigorously stirred and centrifuged at 5250 rpm. A dilution solvent (208 μL) was added to the centrifuged supernatant (12 μL). The solution (50 μL) was taken, and the dilution solvent (150 μL) was added to give a sample solution for compound plasma concentration measurement (mobile phase A:mobile phase B=7:3 (v/v) was used as the dilution solvent).

brain pre-treatment conditions: A standard solution dissolution solvent (DMSO/acetonitrile (2:8)) or a standard solution (5 μL) was added to a sample (50 μL). Acetonitrile (150 μL) containing the internal standard substance was added, and the mixture was vigorously stirred, and centrifuged at 5250 rpm. A dilution solvent (208 μL) was added to the centrifuged supernatant (12 μL). The solution (50 μL) was taken, and the dilution solvent (150 μL) was added to give a sample solution for intracerebral compound concentration measurement (mobile phase A:mobile phase B=7:3 (v/v) was used as the dilution solvent).

TABLE 3

| Example No. | Kp value | administration method | sampling time |
|---|---|---|---|
| 6 | 0.1 | 0.2 mg/1 mL/kg, i.v. | 0.25 hr |
| 10 | 0.33 | 0.2 mg/1 mL/kg, i.v. | 0.5 hr |
| 92 | 0.16 | 1 mg/10 mL/kg, p.o. | 1 hr |
| 94 | 0.03 | 1 mg/10 mL/kg, p.o. | 1 hr |

Kp value was calculated as an average ratio of intracerebral compound concentration (μg/g) and plasma concentration (μg/mL) of each individual at the sampling time.

INDUSTRIAL APPLICABILITY

The compound of the present invention is useful as a cholinergic muscarinic M1 receptor function enhancer, or a medicament such as a prophylactic or therapeutic drug for Alzheimer's disease, schizophrenia, pain (pain), sleep disorder, and the like, and the like.

This application is based on patent application No. 2012-47320 filed in Japan, the contents of which are incorporated by reference in full herein.

The invention claimed is:

1. A compound represented by the formula (I)

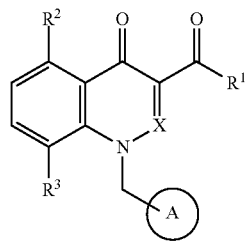

wherein
R$^1$ is
(a) an amino group optionally substituted by 1 or 2 substituents selected from
(1) an amino group,
(2) a C$_{1-6}$ alkyl group optionally substituted by 1 to 3 substituents selected from
(i) a hydroxyl group, (ii) a C$_{1-3}$ alkoxy group, (iii) a C$_{3-6}$ cycloalkyl group substituted by 1 to 3 hydroxyl groups, (iv) a phenyl group, (v) a furyl group, (vi) a tetrahydrofuranyl group, (vii) a piperidino group and (viii) a morpholino group,
(3) a C$_{3-6}$ cycloalkyl group optionally substituted by 1 to 3 substituents selected from a halogen atom, a hydroxyl group and a hydroxymethyl group,
(4) a 4- to 10-membered cyclic amino group,
(5) a phenyl group optionally substituted by 1 to 3 substituents selected from a halogen atom, a C$_{1-6}$ alkyl group optionally substituted by 1 to 3 halogen atoms and a hydroxymethyl group,
(6) a dihydroindenyl group substituted by 1 to 3 hydroxyl groups,
7) a pyrazolyl group,
(8) a tetrahydrofuranyl group, and
(9) a tetrahydropyranyl group substituted by 1 to 3 hydroxyl groups, or
(b) a 4- to 10-membered cyclic amino group optionally substituted by 1 to 3 substituents selected from a hydroxyl group and a hydroxymethyl group,
R$^2$ and R$^3$ are the same and each is a hydrogen atom or a halogen atom, or
R$^2$ is a hydrogen atom, and R$^3$ is a halogen atom, or a C$_{1-3}$ alkoxy group substituted by 1 to 3 halogen atoms,
X is —CH═ or —N═, and
ring A is a phenyl group wherein the 4-position is substituted by a substituent selected from
(i) a C$_{1-3}$ alkyl group substituted by 1 to 3 halogen atoms, (ii) a C$_{1-3}$ alkoxy group, (iii) a carbamoyl group, (iv) a pyrazolyl group optionally substituted by 1 to 3 C$_{1-3}$ alkyl groups and (v) a pyridyl group substituted by 1 to 3 C$_{1-3}$ alkyl groups,
or a salt thereof,
provided that
(1) R$^1$ is not an amino group substituted by a substituent selected from a saturated azabicyclo ring group and a tetrazolyl group;
(2) R$^1$ is not a group represented by the formula
wherein R$^a$ is a hydrogen atom; and
(3) the following compounds are excluded
(i) N-cyclohexyl-1,4-dihydro-1-[(4-methoxyphenyl)methyl]-4-oxo-3-quinolinecarboxamide, and (ii) 1,4-dihydro-1-[(4-methoxyphenyl)methyl]-N-(2-methylphenyl)-4-oxo-3-quinolinecarboxamide.

2. 1,5-Anhydro-2,3-dideoxy-3-({[5,8-difluoro-1-(4-methoxybenzyl)-4-oxo-1,4-dihydroquinolin-3-yl]carbonyl}amino)-DL-threo-pentitol, or a salt thereof.

3. 5,8-Difluoro-N-[(1,2-trans)-2-hydroxycyclohexyl]-1-(4-methoxybenzyl)-4-oxo-1,4-dihydroquinoline-3-carboxamide, or a salt thereof.

4. 8-Fluoro-N-[(1,2-trans)-2-hydroxycyclopentyl]-4-oxo-1-[4-(1H-pyrazol-1-yl)benzyl]-1,4-dihydroquinoline-3-carboxamide, or a salt thereof.

5. 1-[4-(1,3-Dimethyl-1H-pyrazol-4-yl)benzyl]-N-[(1,2-trans)-2-hydroxycyclopentyl]-4-oxo-1,4-dihydroquinoline-3-carboxamide, or a salt thereof.

6. A medicament comprising the compound according to claim 1, or a salt thereof.

7. The medicament according to claim 1, which is a therapeutic drug for Alzheimer's disease, schizophrenia, pain, a sleep disorder or Lewy body dementia.

8. The compound according to claim 1, wherein $R^1$ is an amino group optionally substituted by one substituent selected from
(1) an amino group,
(2) a $C_{1-6}$ alkyl group optionally substituted by 1 to 3 substituents selected from
(i) a hydroxyl group, (ii) a $C_{1-3}$ alkoxy group and (iii) a $C_{3-6}$ cycloalkyl group substituted by 1 to 3 hydroxyl groups,
(3) a $C_{3-6}$ cycloalkyl group optionally substituted by 1 to 3 substituents selected from a halogen atom, a hydroxyl group and a hydroxymethyl group,
(4) a piperidino group,
(5) a phenyl group optionally substituted by 1 to 3 substituents selected from a $C_{1-6}$ alkyl group optionally substituted by 1 to 3 halogen atoms, and
(6) a tetrahydropyranyl group substituted by 1 to 3 hydroxyl groups,
$R^2$ and $R^3$ are the same and each is a hydrogen atom or a halogen atom, or
$R^2$ is a hydrogen atom, and $R^3$ is a halogen atom,
X is —CH= or —N=, and
ring A is a phenyl group wherein the 4-position is substituted by a substituent selected from
(i) a $C_{1-3}$ alkyl group substituted by 1 to 3 halogen atoms,
(ii) a $C_{1-3}$ alkoxy group, (iii) a carbamoyl group, (iv) a pyrazolyl group optionally substituted by 1 to 3 $C_{1-3}$ alkyl groups and (v) a pyridyl group substituted by 1 to 3 $C_{1-3}$ alkyl groups,
or a salt thereof.

9. The compound according to claim 1, wherein $R^1$ is
an amino group substituted by one substituent selected from
(1) an amino group,
(2) a $C_{3-6}$ cycloalkyl group substituted by 1 to 3 substituents selected from a halogen atom and a hydroxyl group, and
(3) a tetrahydropyranyl group substituted by 1 to 3 hydroxyl groups,
$R^2$ and $R^3$ are the same and each is a hydrogen atom or a halogen atom, or
$R^2$ is a hydrogen atom, and $R^3$ is a halogen atom,
X is —CH= or —N=, and
ring A is a phenyl group wherein the 4-position is substituted by a substituent selected from
(i) a $C_{1-3}$ alkoxy group, (ii) a carbamoyl group, (iii) a pyrazolyl group optionally substituted by 1 to 3 $C_{1-3}$ alkyl groups and (iv) a pyridyl group substituted by 1 to 3 $C_{1-3}$ alkyl groups, or a salt thereof.

10. The medicament according to claim 6, which is a cholinergic muscarinic M1 receptor positive allosteric modulator.

11. A method for the treatment of Alzheimer's disease, schizophrenia, pain, a sleep disorder or Lewy body dementia, comprising administering an effective amount of the compound according to claim 1, or a salt thereof to a mammal.

12. The compound according to claim 1 or a salt thereof for use in cholinergic muscarinic M1 receptor positive allosteric modulation.

13. The compound according to claim 1 or a salt thereof for use in the treatment of Alzheimer's disease, schizophrenia, pain, a sleep disorder or Lewy body dementia.

14. A method of cholinergic muscarinic M1 receptor positive allosteric modulation, comprising administering an effective amount of the compound according to claim 1 or a salt thereof to a mammal.

\* \* \* \* \*